US012674131B2

(12) United States Patent
Tennant et al.

(10) Patent No.: US 12,674,131 B2
(45) Date of Patent: Jul. 7, 2026

(54) LIVE ATTENUATED NON-TRANSMISSIBLE VACCINES

(71) Applicant: University of Maryland, Baltimore, Baltimore, MD (US)

(72) Inventors: Sharon Tennant, Ellicott City, MD (US); James Eugene Galen, Eldersburg, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 1048 days.

(21) Appl. No.: 17/532,784

(22) Filed: Nov. 22, 2021

(65) Prior Publication Data

US 2022/0154135 A1     May 19, 2022

Related U.S. Application Data

(63) Continuation-in-part of application No. PCT/US2020/034596, filed on May 26, 2020.

(60) Provisional application No. 62/853,348, filed on May 28, 2019, provisional application No. 62/852,037, filed on May 23, 2019.

(51) Int. Cl.
| | |
|---|---|
| *A61K 39/12* | (2006.01) |
| *A61K 39/112* | (2006.01) |
| *A61P 31/04* | (2006.01) |
| *C12N 1/36* | (2006.01) |
| *C12N 15/74* | (2006.01) |
| *A61K 39/00* | (2006.01) |

(52) U.S. Cl.
CPC ............ *C12N 1/36* (2013.01); *A61K 39/0275* (2013.01); *A61P 31/04* (2018.01); *C12N 15/74* (2013.01); *A61K 2039/522* (2013.01); *C12N 2840/002* (2013.01)

(58) Field of Classification Search
None
See application file for complete search history.

(56) References Cited

U.S. PATENT DOCUMENTS

| | | | |
|---|---|---|---|
| 9,109,229 | B2 | 8/2015 | Ramseier et al. |
| 2015/0361436 | A1 | 12/2015 | Hitchcock et al. |
| 2016/0177274 | A1 | 6/2016 | Falb et al. |

OTHER PUBLICATIONS

Guzman et al (J Bacteriol. Jul. 1995;177(14):4121-4130).*
Zhao et al (Vaccine. 2018. 36(33): 5010-5019).*
International Search Report from Appl. No. PCT/US20/34596, mailed on Sep. 4, 2020.
Rex et al., A Genetic Analysis of the Functional Interactions within Mycobacterium tuberculosis Single-Stranded DNA Binding Protein, PLOS ONE, (2014), 9:e94669; p. 1-10.
Miyada et al., Regulation of the araC gene of *Escherichia coli*: Catabolite repression, autoregulation, and effect on araBAD expression, Proc. NNatl. Acad. Sci. USA, (1984), 81:4120-4124.

* cited by examiner

*Primary Examiner* — Jennifer E Graser
(74) *Attorney, Agent, or Firm* — Nevrivy Patent Law Group P.L.L.C.

(57) ABSTRACT

The present invention provides genetically modified microorganisms with reduced transmissibility, wherein the microorganism has been genetically modified to express a single stranded binding protein (SSB) regulated by an arabinose responsive promoter, wherein the microorganism has a reduced growth capacity in the absence of arabinose.

18 Claims, 16 Drawing Sheets

Specification includes a Sequence Listing.

A

B

| Vaccine | Host | Duration of shedding |
|---------|------|----------------------|
| *S.* Typhi Ty21a | Humans | 3 days |
| *S.* Typhimurium Δ*aroA* Δ*ssaV* | Humans | 21 days |
| *S.* Typhimurium Δ*guaBA* Δ*clpP* | Rhesus macaques | 10 days |
| *S.* Typhimurium Δ*guaBA* Δ*clpP* Δ*pipA* Δ*htrA* | Rhesus macaques | 4-7 days |

*S.* Typhimurium Δ*guaBA* Δ*clpP* Δ*pipA* Δ*htrA*

FIG. 15

| Strain | Peroral LD₅₀ in BALB/c mice |
|---|---|
| D65 | $2 \times 10^4$ CFU |
| D65 $P_{BAD}$-*ssb* | $> 10^9$ CFU (No mortality at $10^9$ CFU; n=10) |
| D65* | $7.77 \times 10^4$ CFU |
| D65* $P_{BAD}$-*ssb* | $> 10^9$ CFU (No mortality at $9 \times 10^8$ CFU; n=5) |

FIG. 16

| | Day 1 | Day 2 | Day 3 | Day 4 | Day 5 | Day 6 | Day 7 | No. of shedding days |
|---|---|---|---|---|---|---|---|---|
| D65 PBAD-ssb | 15/15 (100%) | 2/14 (14%) | 12/14 (86%) | 2/14 (14%) | 9/14 (64%) | 3/14 (21%) | 2/14 (14%) | 45/99 (45%) |
| D65* PBAD-ssb | 15/15 (100%) | 13/14 (93%) | 9/13 (69%) | 7/13 (54%) | 8/13 (62%) | 7/13 (54%) | 6/13 (46%) | 65/94 (69%) |
| CVD 1931 | 15/15 (100%) | 11/15 (73%) | 10/15 (67%) | 7/15 (47%) | 10/15 (67%) | 8/15 (53%) | 9/15 (60%) | 70/105 (67%) |

| | Day 1 | Day 2 | Day 3 | Day 4 | Day 5 | Day 6 | Day 7 | Day 9 | Day 11 | Day 14 | Day 21 | Day 28 | No. of shedding days |
|---|---|---|---|---|---|---|---|---|---|---|---|---|---|
| CVD 1931 PBAD-ssb D65 | 13/15 (87%) | 2/15 (13%) | 5/15 (33%) | 3/15 (20%) | 6/15 (40%) | 0/15 (0%) | 0/15 (0%) | 0/15 (0%) | 0/15 (0%) | 0/15 (0%) | 0/15 (0%) | 0/15 (0%) | 29/180 (16%) |
| ΔguaBA* PBAD-ssb | 15/15 (100%) | 6/15 (40%) | 8/15 (53%) | 6/15 (40%) | 5/15 (33%) | 2/15 (13%) | 0/15 (0%) | 0/15 (0%) | 0/15 (0%) | 0/15 (0%) | 0/15 (0%) | 0/15 (0%) | 42/180 (23%) |
| CVD 1931 | 15/15 (100%) | 10/15 (67%) | 9/15 (60%) | 4/15 (27%) | 12/15 (80%) | 5/15 (33%) | 3/15 (20%) | 3/15 (20%) | 3/15 (20%) | 0/15 (0%) | 0/15 (0%) | 0/15 (0%) | 64/180 (36%) |

LIVE ATTENUATED NON-TRANSMISSIBLE VACCINES

CROSS-REFERENCE TO RELATED APPLICATIONS

This application is a continuation-in-part of International Appl. No.: PCT/US2020/034596, filed May 26, 2020, which claims the benefit of U.S. Provisional Appl. No. 62/852,037, filed on May 23, 2019, and U.S. Provisional Appl. No. 62/853,348, filed May 28, 2019, the contents of which are hereby incorporated by reference in their entirety.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 36,894 Byte ASCII (Text) file named "Sequence_listing_ST25.txt," created on May 26, 2020.

FIELD OF THE INVENTION

The field of the invention relates generally to the field of medicine and infectious diseases, molecular biology, and in particular vaccine technology.

BACKGROUND OF THE INVENTION

When the recombinant microorganism is used as a vertebrate live vaccine, certain considerations must be taken into account. To provide a benefit beyond that of a nonliving vaccine, the live vaccine microorganism must attach to, invade, and survive in lymphoid tissues of the vertebrate and expose these immune effector sites to antigen for an extended period of time. Through this continual stimulation, the vertebrate's immune system becomes more highly reactive to the antigen than with a nonliving vaccine. Therefore, preferred live vaccines are attenuated pathogens of the vertebrate, particularly pathogens that colonize the gut-associated lymphoid tissue (GALT), nasopharynx-associated lymphoid tissue (NALT) or bronchial-associated lymphoid tissue (BALT). An additional advantage of these attenuated pathogens over nonliving vaccines is that these pathogens have elaborate mechanisms to gain access to lymphoid tissues, and thus efficient exposure to the vertebrate's immune system can be expected. In contrast, nonliving vaccines will only provide an immune stimulus if the vaccine is passively exposed to the immune system, or if host mechanisms bring the vaccine to the immune system.

*Salmonella enterica* is a facultative intracellular pathogen responsible for a high burden of mortality and morbidity worldwide. Human host-restricted *S. enterica* serovars Typhi, ParaTyphi A and ParaTyphi B cause enteric fever. Other *Salmonella* serovars have a broader host range and mainly cause gastroenteritis in animals and humans; they are referred to as non-typhoidal *Salmonella* (NTS). *S. enterica* is classified into serogroups based on the O antigen (LPS) and serovars based on the O and H (flagella) antigens.

Approximately 80 million human NTS infections worldwide (86%) are estimated to be foodborne (Majowicz S E, Musto J, Scallan E, Angulo F J, Kirk M, O'Brien S J, et al. The global burden of nontyphoidal *Salmonella* gastroenteritis. Clin Infect Dis. 2010; 50(6): 882-9). Moreover, multiple outbreaks related to contact with infected animals have been reported (Cavallo S J, Daly E R, Seiferth J, Nadeau A M, Mahoney J, Finnigan J, et al. Human outbreak of *Salmonella* Typhimurium associated with exposure to locally made chicken jerky pet treats, New Hampshire, 2013. Foodborne Pathog Dis. 2015; 12(5): 441-6; Behravesh C B, Brinson D, Hopkins B A, Gomez T M. Backyard poultry flocks and salmonellosis: a recurring, yet preventable public health challenge. Clin Infect Dis. 2014; 58(10): 1432-8). In 2010, the World Health Organization (WHO) estimated that NTS was the leading cause of foodborne deaths worldwide (Havelaar A H, Kirk M D, Torgerson P R, Gibb H J, Hald T, Lake R J, et al. World Health Organization Global Estimates and Regional Comparisons of the Burden of Foodborne Disease in 2010. PLoS Med. 2015; 12(12): e1001923). NTS is estimated to have caused 153 million diarrheal cases and 57,000 deaths in 2010 (Murray C J, Vos T, Lozano R, Naghavi M, Flaxman A D, Michaud C, et al. Disability-adjusted life years (DALYs) for 291 diseases and injuries in 21 regions, 1990-2010: a systematic analysis for the Global Burden of Disease Study 2010. Lancet. 2012; 380(9859): 2197-223). NTS produces vomiting, diarrhea, fever and abdominal pain 12 to 72 hours after ingestion. Symptoms last for 4 to 7 days and most people resolve the disease without any interventions but in some cases, mostly in the very young, elderly and immunocompromised, NTS can become invasive and ultimately result in death (Vugia D J, Samuel M, Farley M M, Marcus R, Shiferaw B, Shallow S, et al. Invasive *Salmonella* infections in the United States, FoodNet, 1996-1999: incidence, serotype distribution, and outcome. Clin Infect Dis. 2004; 38 Suppl 3: S149-56; Kennedy M, Villar R, Vugia D J, Rabatsky-Ehr T, Farley M M, Pass M, et al. Hospitalizations and deaths due to *Salmonella* infections, FoodNet, 1996-1999. Clin Infect Dis. 2004; 38 Suppl 3: S142-8). Interventions effective against other bacterial enteropathogens have failed to diminish Salmonellosis in the U.S., making vaccination an attractive option (Crim S M, Griffin P M, Tauxe R, Marder E P, Gilliss D, Cronquist A B, et al. Preliminary incidence and trends of infection with pathogens transmitted commonly through food—Foodborne Diseases Active Surveillance Network, 10 U.S. sites, 2006-2014. MMWR Morb Mortal Wkly Rep. 2015; 64(18): 495-9). The most recent FoodNet data indicates that there were 7,452 laboratory-confirmed infections per 100,000 population, 2,141 hospitalizations and 30 deaths due to *Salmonella* in 2014 (Crim S M, Griffin P M, Tauxe R, Marder E P, Gilliss D, Cronquist A B, et al. Preliminary incidence and trends of infection with pathogens transmitted commonly through food—Foodborne Diseases Active Surveillance Network, 10 U.S. sites, 2006-2014. MMWR Morb Mortal Wkly Rep. 2015; 64(18): 495-9). Among foodborne pathogens, NTS causes the most disability adjusted life years (32,900 DALYs annually) in the U.S. (Scallan E, Hoekstra R M, Mahon B E, Jones T F, Griffin P M. An assessment of the human health impact of seven leading foodborne pathogens in the United States using disability adjusted life years. Epidemiol Infect. 2015; 143(13): 2795-804). *Salmonella* is one of the leading causes of death in the U.S. due to foodborne bacterial pathogens. (Crim S M, Griffin P M, Tauxe R, Marder E P, Gilliss D, Cronquist A B, et al. Preliminary incidence and trends of infection with pathogens transmitted commonly through food—Foodborne Diseases Active Surveillance Network, 10 U.S. sites, 2006-2014. MMWR Morb Mortal Wkly Rep. 2015; 64(18): 495-9; Barton Behravesh C, Jones T F, Vugia D J, Long C, Marcus R, Smith K, et al. Deaths associated with bacterial pathogens transmitted commonly through food: foodborne diseases active surveillance network (FoodNet), 1996-2005. J Infect Dis. 2011; 204(2): 263-7). The Healthy People 2020 objective target is 11.4 laboratory-confirmed *Salmonella* infections per 100,000. In industrialized countries like the USA, the mass production food industry creates opportunities for NTS to be widely disseminated if a breakdown in food hygiene or some other form of contamination occurs, leading to amplification of transmission and large multi-state outbreaks. At least one large multi-state outbreak of NTS gastroenteritis occurs virtually every year in the USA. The majority of NTS infections are due to serogroups B (O:4; mostly Typhimurium), $C_1$ (O:6,7), $C_{2-3}$ (O:6,8) and D (O:9; mostly Enteritidis), where they constitute ~90% of NTS infections (Fuche F J, Sow O, Simon R, Tennant S M. *Salmonella* serogroup C: Current status of vaccines and why they are needed. Clin Vaccine Immunol. 2016).

An unexpected consequence of systematic blood and body fluid (cerebrospinal fluid, etc) culture-based surveillance for invasive bacterial infections in sub-Saharan Africa was the discovery that in infants and toddlers in multiple geographic sites, NTS rivaled *Haemophilus influenzae* type b (Hib) and *Streptococcus pneumoniae* infections in their frequency and severity. (Berkley J A, Lowe B S, Mwangi 1, Williams T, Bauni E, Mwarumba S, et al. Bacteremia among children admitted to a rural hospital in Kenya. N Engl J Med. 2005; 352(1): 39-47; Brent A J, Oundo J O, Mwangi 1, Ochola L, Lowe B, Berkley J A. *Salmonella* bacteremia in Kenyan children. Pediatr Infect Dis J. 2006; 25(3): 230-6; Graham S M, Walsh A L, Molyneux E M, Phiri A J, Molyneux M E. Clinical presentation of non-typhoidal *Salmonella* bacteraemia in Malawian children. Trans R Soc Trap Med Hyg. 2000; 94(3); 310-4; Ikumapayi U N, Antonio M, Sonne-Hansen J, Biney E, Enwere G, Okoko B, et al. Molecular epidemiology of community-acquired invasive non-typhoidal *Salmonella* among children aged 2 29 months in rural Gambia and discovery of a new serovar. *Salmonella enterica* Dingiri. J Med Microbiol. 2007; 56(Pt II): 1479-84; Kariuki S, Revathi G, Kariuki N, Kiiru J, Mwituria J, Hart C A. Characterisation of community acquired nontyphoidal *Salmonella* from bacteraemia and diarrhoeal infections in children admitted to hospital in Nairobi, Kenya. BMC Microbiol. 2006; 6:101; Lepage P, Bogaerts J, Van Goethem C, Ntahorutaba M, Nsengumuremyi F, Hitimana D G, et al. Community-acquired bacteraemia in African children. Lancet. 1987; 1(8548): 1458-61; Mandomando 1, Macete E, Sigauque B, Morais L, Quinto L, Sacarlal J, et al. Invasive non-typhoidal *Salmonella* in Mozambican children. Trap Med Int Health. 2009; 14(12): 1467-74; O' Dempsey T J, McArdle T F, Lloyd-Evans N, Baldeh I, Laurence B E, Secka 0, et al. Importance of enteric bacteria as a cause of pneumonia, meningitis and septicemia among children in a rural community in The Gambia, West Africa. Pediatr Infect Dis J. 1994; 13(2): 122-8; Sigauque B, Roca A, Mandomando 1, Morais L, Q. uinto L, Sacarlal J, et al. Community-acquired bacteremia among children admitted to a rural hospital in Mozambique. Pediatr Infect Dis J. 2009; 28(2): 108-13; Walsh A L, Phiri A J, Graham S M, Molyneux E M, Molyneux M E. Bacteremia in febrile Malawian children: clinical and microbiologic features. Pediatr Infect DisJ. 2000; 19(4): 312-8). The incidence of invasive non-typhoidal *Salmonella* NTS (iNTS) disease has been reported to be up to 237 cases per 100,000 population at certain sites. (Marks F, van Kalckreuth V, Aaby P, Adu-Sarkodie Y, El Tayeb M A, Ali M, et al. Incidence of invasive *salmonella* disease in sub-Saharan Africa: a multicentre population-based surveillance study. Lancet Glob Health. 2017; 5(3): e310-e23; Ao T T, Feasey N A, Gordon M A, Keddy K H, Angulo F J, Crump J A. Global burden of invasive nontyphoidal *Salmonella* disease, 2010(1). Emerg Infect Dis.

2015; 21(6)). Ao et al., estimated the global burden of iNTS disease to be 3.4 million cases and 681,316 deaths annually. Case fatality rates are typically between 20 and 30%. (Brent A J, Oundo J O, Mwangi 1, Ochola L, Lowe B, Berkley J A. *Salmonella* bacteremia in Kenyan children. Pediatr Infect Dis J. 2006; 25(3): 230-6; Graham S M, Walsh A L, Molyneux E M, Phiri A J, Molyneux M E. Clinical presentation of non-typhoidal *Salmonella* bacteraemia in Malawian children. Trans R Soc Trap Med Hyg. 2000; 94(3); 310-4; Kariuki S, Revathi G, Kariuki N, Kiiru J, Mwituria J, Hart C A. Characterisation of community acquired non-typhoidal *Salmonella* from bacteraemia and diarrhoeal infections in children admitted to hospital in Nairobi, Kenya. BMC Microbiol. 2006; 6:101; Mandomando 1, Macete E, Sigauque B, Morais L, Quinto L, Sacarlal J, et al. Invasive non-typhoidal *Salmonella* in Mozambican children. Trap Med Int Health. 2009; 14(12): 1467-74) Interestingly, two-thirds of the African iNTS cases neither present with gastroenteritis nor even have a history of gastroenteritis (Enwere G, Biney E, Cheung Y B, Zaman S M, Okoko B, Oluwalana C, et al. Epidemiologic and clinical characteristics of community-acquired invasive bacterial infections in children aged 2-29 months in The Gambia. Pediatr Infect Dis J. 2006; 25(8): 700-5). While severe malaria anemia and HIV are important risk factors, iNTS disease is also a major health problem in low HIV prevalence areas in Africa. (Enwere G, Biney E, Cheung Y B, Zaman S M, Okoko B, Oluwalana C, et al. Epidemiologic and clinical characteristics of community-acquired invasive bacterial infections in children aged 2-29 months in The Gambia. Pediatr Infect Dis J. 2006; 25(8): 700-5; Gordon M A. *Salmonella* infections in immunocompromised adults. J Infect. 2008; 56(6): 413-22; Park S E, Pak G D, Aaby P, Adu-Sarkodie Y, Ali M, Aseffa A, et al. The Relationship Between Invasive Nontyphoidal almonella Disease, Other Bacterial Bloodstream Infections, and Malaria in Sub-Saharan Africa. Clin Infect Dis. 2016; 62; Suppl 1: S23-31; Tennant S M, Diallo S, Levy H, Livio S, Sow S O, Tapia M, et al. Identification by PCR of non-typhoidal *Salmonella enterica* serovars associated with invasive infections among febrile patients in Mali. PLoS NeglTrop Dis. 2010; 4(3): e621). In Africa, children are particularly susceptible to invasive infections due to iNTS. In sub-Saharan Africa, iNTS mainly infects children <2 years of age (FIG. 7), whereas typhoidal *Salmonella* serovars are more common in school-age children. ((Tapia M D, Tennant S M, Bornstein K, Onwuchekwa U, Tamboura B, Maiga A, et al. Invasive nontyphoidal *Salmonella* infections among children in Mali, 2002-2014: Microbiological and epidemiologic features guide vaccine development. Clin Infect Dis. 2015; 61 Suppl 4: S332-8; MacLennan C A, Gondwe E N, Msefula C L, Kingsley R A, Thomson N R, White S A, et al. The neglected role of antibody in protection against bacteremia caused by nontyphoidal strains of *Salmonella* in African children. J Clin Invest. 2008; 118(4): 1553-62; The global burden of typhoid and paratyphoid fevers: a systematic analysis for the Global Burden of Disease Study 2017. Lancet Infect Dis. 2019; 19(4): 369-81).

Surveys from multiple sites in sub-Saharan Africa reveal that ~80-90% of NTS from cases of invasive disease are *Salmonella enterica* serovar Typhimurium and monophasic *S. Typhimurium* variants, serovars that fall into *Salmonella* group B, or S. Enteritidis, a group D *Salmonella* serovar (FIG. 8). (Tapia M D, Tennant S M, Bornstein K, Onwuchekwa U, Tamboura B, Maiga A, et al. Invasive nontyphoidal *Salmonella* infections among children in Mali, 2002-2014: Microbiological and epidemiologic features guide vaccine development. Clin Infect Dis. 2015; 61 Suppl 4: S332-8; Berkley J A, Lowe B S, Mwangi 1, Williams T, Bauni E, Mwarumba S, et al. Bacteremia among children admitted to a rural hospital in Kenya. N Engl J Med. 2005; 352(1): 39-47; Brent A J, Oundo J O, Mwangi 1, Ochola L, Lowe B, Berkley J A. *Salmonella* bacteremia in Kenyan children. Pediatr Infect Dis J. 2006; 25(3): 230-6; Graham S M, Walsh A L, Molyneux E M, Phiri A J, Molyneux M E. Clinical presentation of non-typhoidal *Salmonella* bacteraemia in Malawian children. Trans R Soc Trap Med Hyg. 2000; 94(3); 310-4; Ikumapayi U N, Antonio M, Sonne-Hansen J, Biney E, Enwere G, Okoko B, et al. Molecular epidemiology of community-acquired invasive non-typhoidal *Salmonella* among children aged 2 29 months in rural Gambia and discovery of a new serovar. *Salmonella enterica* Dingiri. J Med Microbiol. 2007; 56(Pt II): 1479-84; Kariuki S, Revathi G, Kariuki N, Kiiru J, Mwituria J, Hart C A. Characterisation of community acquired nontyphoidal *Salmonella* from bacteraemia and diarrhoeal infections in children admitted to hospital in Nairobi, Kenya. BMC Microbiol. 2006; 6:101; Lepage P, Bogaerts J, Van Goethem C, Ntahorutaba M, Nsengumuremyi F, Hitimana D G, et al. Community-acquired bacteraemia in African children. Lancet. 1987; 1(8548): 1458-61; Mandomando 1, Macete E, Sigauque B, Morais L, Quinto L, Sacarlal J, et al. Invasive non-typhoidal *Salmonella* in Mozambican children. Trap Med Int Health. 2009; 14(12): 1467-74; O'Dempsey T J, McArdle T F, Lloyd-Evans N, Baldeh I, Laurence B E, Secka 0, et al. Importance of enteric bacteria as a cause of pneumonia, meningitis and septicemia among children in a rural community in The Gambia, West Africa. Pediatr Infect Dis J. 1994; 13(2): 122-8; Walsh A L, Phiri A J, Graham S M, Molyneux E M, Molyneux M E. Bacteremia in febrile Malawian children: clinical and microbiologic features. Pediatr Infect DisJ. 2000; 19(4): 312-8; The global burden of typhoid and paratyphoid fevers: a systematic analysis for the Global Burden of Disease Study 2017. Lancet Infect Dis. 2019; 19(4): 369-81; Mandomando I, Bassat Q, Sigauque B, Massora S, Quinto L, Acacio S, et al. Invasive *Salmonella* Infections Among Children From Rural Mozambique, 2001-2014. Clin Infect Dis. 2015; 61 Suppl 4: S339-45; Feasey N A, Dougan G, Kingsley R A, Heyderman R S, Gordon M A. Invasive non-typhoidal *Salmonella* disease: an emerging and neglected tropical disease in Africa. Lancet. 2012; 379(9835): 2489-99; Dekker D, Krumkamp R, Eibach D, Sarpong N, Boahen K G, Frimpong M, et al. Characterization of *Salmonella enterica* from invasive bloodstream infections and water sources in rural Ghana. BMC Infect Dis. 2018; 18(1): 47; In Mali, S. Dublin and S. stanleyville are also isolated at a high frequency. (Tapia M D, Tennant S M, Bornstein K, Onwuchekwa U, Tamboura B, Maiga A, et al. Invasive nontyphoidal *Salmonella* infections among children in Mali, 2002-2014: Microbiological and epidemiologic features guide vaccine development. Clin Infect Dis. 2015; 61 Suppl 4: S332-8). Genomics analyses have shown that there are novel strains of S. Typhimurium and S. Enteritidis that are circulating in Africa and which differ from global NTS strains. (Okoro C K, Kingsley R A, Connor T R, Harris S R, Parry C M, Al-Mashhadani M N, et al. Intracontinental spread of human invasive *Salmonella* Typhimurium pathovariants in sub-Saharan Africa. Nat Genet. 2012; 44(11); 1215-21; Feasey N A, Hadfield J, Keddy K H, Dallman T J, Jacobs J, Deng X, et al. Distinct *Salmonella* Enteritidis lineages associated with enterocolitis in high-income settings and invasive disease in low-income settings. Nat Genet. 2016; 48(10): 1211-7. In particular, there is a multi-locus sequence type of S. Typhimurium called ST313 that is predominant in Africa (Kingsley R A, Msefula C L, Thomson N R, Kariuki S, Holt K E, Gordon M A, et al. Epidemic multiple drug resistant *Salmonella* Typhimurium causing invasive disease in sub-Saharan Africa have a distinct genotype. Genome Res. 2009; 19(12): 2279-87). iNTS strains are also phenotypically different from gastroenteritis-associated genotypes (Feasey N A, Hadfield J, Keddy K H, Dallman T J, Jacobs J, Deng X, et al. Distinct *Salmonella* Enteritidis lineages associated with enterocolitis in high-income settings and invasive disease in low-income settings. Nat Genet. 2016; 48(10): 1211-7; Ramachandran G, Panda A, Higginson E E, Ateh E, Lipsky M M, Sen S, et al. Virulence of invasive *Salmonella* Typhimurium ST313 in animal models of infection. PLoS Negl Trap Dis. 2017; 11(8): e0005697; Ramachandran G, Aheto K, Shirtliff M E, Tennant S M. Poor biofilm-forming ability and long-term survival of invasive *Salmonella* Typhimurium ST313. Pathog Dis. 2016; 74(5)).

The growing resistance of NTS strains to multiple antibiotics makes NTS disease difficult to treat. (Sigauque B, Roca A, Mandomando 1, Morais L, Q. uinto L, Sacarlal J, et al. Community-acquired bacteremia among children admitted to a rural hospital in Mozambique. Pediatr Infect Dis J. 2009; 28(2): 108-13; Walsh A L, Phiri A J, Graham S M, Molyneux E M, Molyneux M E. Bacteremia in febrile Malawian children: clinical and microbiologic features. Pediatr Infect DisJ. 2000; 19(4): 312-8). In the most recent CDC antimicrobial resistance report released in 2019, multidrug resistant NTS were classified as a Serious Threat ($2^{nd}$ highest threat level after "Urgent Threat"). In 2017, the WHO classified fluroquinolone-resistant *Salmonella* in their Priority 2 (High) list of antibiotic-resistant bacteria to guide research, discovery and development of new antibiotics. Further, patients with antimicrobial resistant NTS are more likely to have bloodstream infection and to be hospitalized than patients with pansusceptible NTS. (Sigauque B, Roca A, Mandomando 1, Morais L, Q. uinto L, Sacarlal J, et al. Community-acquired bacteremia among children admitted to a rural hospital in Mozambique. Pediatr Infect Dis J. 2009; 28(2): 108-13).

A multivalent formulation of live attenuated S. Typhimurium (serogroup B), S. Enteritidis (serogroup D), S. Virchow (serogroup $C_1$) and S. Newport (serogroup $C_{2-3}$) vaccines is being developed to prevent the majority of NTS gastroenteritis infections in the U.S. as well as globally. ((Marks F, van Kalckreuth V, Aaby P, Adu-Sarkodie Y, El Tayeb M A, Ali M, et al. Incidence of invasive *salmonella* disease in sub-Saharan Africa: a multicentre population-based surveillance study. Lancet Glob Health. 2017; 5(3): e310-e23; Ao T T, Feasey N A, Gordon M A, Keddy K H, Angulo F J, Crump J A. Global burden of invasive nontyphoidal *Salmonella* disease, 2010(1). Emerg Infect Dis. 2015; 21(6); Enwere G, Biney E, Cheung Y B, Zaman S M, Okoko B, Oluwalana C, et al. Epidemiologic and clinical characteristics of community-acquired invasive bacterial infections in children aged 2-29 months in The Gambia. Pediatr Infect Dis J. 2006; 25(8): 700-5). Based on immune responses generated against the O polysaccharide, 90% coverage in the U.S. can be theoretically achieved. The vaccine would target infants, elderly and travelers.

There are no licensed iNTS vaccines. However, several groups are developing vaccines to combat these pathogens (Gil-Cruz C, Bobat S, Marshall J L, Kingsley R A, Ross E A, Henderson I R, et al. The porin OmpD from nontyphoidal *Salmonella* is a key target for a protective B1b cell antibody response. Proc Natl Acad Sci USA. 2009; 106(24): 9803-8).

A variety of parenteral vaccines are being developed. The University of Birmingham is developing an OmpD porin subunit vaccine. (Gil-Cruz C, Bobat S, Marshall J L, Kingsley R A, Ross E A, Henderson I R, et al. The porin OmpD from nontyphoidal *Salmonella* is a key target for a protective B1b cell antibody response. Proc Natl Acad Sci USA. 2009; 106(24): 9803-8; Zhang Y, Dominguez-Medina C, Cumley N J, Heath J N, Essex S J, Bobat S, et al. IgG1 Is Required for Optimal Protection after Immunization with the Purified Porin OmpD from *Salmonella* Typhimurium. J Immunol. 2017; 199(12): 4103-9. NIH was the first to develop a S. Typhimurium conjugate vaccine in which O polysaccharide from S. Typhimurium was conjugated to tetanus toxoid. (Watson D C, Robbins J B, Szu S C. Protection of mice against *Salmonella* typhimurium with an O-specific polysaccharide-protein conjugate vaccine. Infect Immun. 1992; 60(11): 4679-86). GSK Global Vaccines for Global Health are pursuing two approaches. They are developing a bivalent (S. Typhimurium and S. Enteritidis) O polysaccharide (OPS):CRM197 conjugate vaccine and also a bivalent outer membrane vesicle-based vaccine called GMMA (Generalized Modules for Membrane Antigens). (Micoli F, Rondini S, Alfini R, Lanzilao L, Necchi F, Negrea A, et al. Comparative immunogenicity and efficacy of equivalent outer membrane vesicle and glycoconjugate vaccines against nontyphoidal *Salmonella*. Proc Natl Acad Sci USA. 2018; 115(41); 10428-33; De Benedetto G, Alfini R, Cescutti P, Caboni M, Lanzilao L, Necchi F, et al. Characterization of O-antigen delivered by Generalized Modules for Membrane Antigens (GMMA) vaccine candidates against nontyphoidal *Salmonella*. Vaccine. 2017; 35(3): 419-26). University of Maryland Baltimore has developed a bivalent S. Typhimurium and S. Enteritidis conjugate using core and O polysaccharide (COPS) and FliC purified from NTS strains genetically engineered to produce these components efficiently (Tennant S M, Wang J Y, Galen J E, Simon R, Pasetti M F, Gat 0, et al. Engineering and preclinical evaluation of attenuated nontyphoidal *Salmonella* strains serving as live oral vaccines and as reagent strains. Infect Immun. 2011; 79(10): 4175-85; Hegerle N, Bose J, Ramachandran G, Galen J E, Levine M M, Simon R, et al. Overexpression of O-polysaccharide chain length regulators in Gram-negative bacteria using the Wzx-/Wzy-dependent pathway enhances production of defined modal length O-polysaccharide polymers for use as haptens in glycoconjugate vaccines. J Appl Microbiol. 2018; 125(2): 575-85). Here COPS is chemically linked to FliC (encodes Phase I flagellin) from the same serovar (Tennant S M, Wang J Y, Galen J E, Simon R, Pasetti M F, et al. Engineering and preclinical evaluation of attenuated nontyphoidal *Salmonella* strains serving as live oral vaccines and as reagent strains. Infect Immun. 2011; 79(10): 4175-85; Baliban S M, Yang M, Ramachandran G, Curtis B, Shridhar S, Laufer R S, et al. Development of a glycoconjugate vaccine to prevent invasive *Salmonella* Typhimurium infections in sub-Saharan Africa. PLoS Negl Trop Dis. 2017; 11(4): e0005493; Simon R, Tennant S M, Wang J Y, Schmidlein P J, Lees A, Ernst R K, et al. *Salmonella enterica* serovar enteritidis core O polysaccharide conjugated to H:g,m flagellin as a candidate vaccine for protection against invasive infection with S. *enteritidis*. Infect Immun. 2011; 79(10); 4240-9; Simon R, Wang J Y, Boyd M A, Tulapurkar M E, Ramachandran G, Tennant S M, et al. Sustained protection in mice immunized with fractional doses of *Salmonella* Enteritidis core and O polysaccharide-flagellin glycoconjugates. PLoS One. 2013; 8(5): e64680. These conjugates are immunogenic and can protect mice against lethal challenge and were shown to be well tolerated in a Phase I Clinical trial.

Several groups have performed Phase I clinical trials using attenuated strains of S. Typhimurium derived from classic human gastroenteritis strains (Angelakopoulos H, Hohmann E L. Pilot study of phoP/phoQ-deleted *Salmonella enterica* serovar typhimurium expressing *Helicobacter pylori* urease in adult volunteers. Infect Immun. 2000; 68(4): 2135-41; Hindle Z, Chatfield S N, Phillimore J, Bentley M, Johnson J, Cosgrove C A, et al. Characterization of *Salmonella enterica* derivatives harboring defined aroC and *Salmonella* pathogenicity island 2 type III secretion system (ssaV) mutations by immunization of healthy volunteers. Infect Immun. 2002; 70(7): 3457-67). These have been used both as live oral vaccines or as live vector vaccines expressing foreign antigens. A ΔphoP ΔphoQ, mutant caused gastroenteritis and fever at high dosage levels but was quite immunogenic (Angelakopoulos H, Hohmann E L. Pilot study of phoP/phoQ-deleted *Salmonella enterica* serovar typhimurium expressing *Helicobacter pylori* urease in adult volunteers. Infect Immun. 2000; 68(4): 2135-41). A ΔaroC ΔssaV mutant was well tolerated but immune responses were inconsistent and often modest (Hindle Z, Chatfield S N, Phillimore J, Bentley M, Johnson J, Cosgrove C A, et al. Characterization of *Salmonella enterica* derivatives harboring defined aroC and *Salmonella* pathogenicity island 2 type III secretion system (ssaV) mutations by immunization of healthy volunteers. Infect Immun. 2002; 70(7): 3457-67). Neither of these vaccine strains has advanced to further clinical development.

The present inventors have developed and evaluated a variety of *Salmonella* live attenuated vaccines. It is believed that live attenuated iNTS vaccines have many advantages: 1) they can induce local immune responses at mucosal surfaces; 2) they are economical to produce (in terms of production, all that is required is fermentation to grow a large culture, lyophilize and then fill vials); 3) they induce long-lived *Salmonella*-specific B and T cell immunity; 4) they are practical to administer to a large population, and 5) they do not generate hazardous waste (e.g., needles and syringes) that needs to be discarded appropriately. (Mestecky J, Nguyen H, Czerkinsky C, Kiyono H. Oral immunization: an update. Curr Opin Gastroenterol. 2008; 24(6):713-9; Pasetti M F, Simon J K, Sztein M B, Levine M M. Immunology of gut mucosal vaccines. Immunol Rev. 2011: 239m: 125-48). However, there are several limitations to live attenuated vaccines. First, one needs to balance immunity and reactogenicity. (Galen J E, Curtiss R, 3rd. The delicate balance in genetically engineering live vaccines. Vaccine. 2014; 32(35): 4376-85). The vaccine may also need to be formulated differently for infants (Cryz S J, Jr Vanprapar N, Thisyakorn U, Olanratmanee T, Losonsky G, Levine M M, et al. Safety and immunogenicity of *Salmonella* Typhi Ty21a vaccine in young Thai children. Infect Immun. 1993; 61(3): 1149-51; Levine M M, Ferreccio C, Cryz S, Ortiz E. Comparison of enteric-coated capsules and liquid formulation of Ty21a typhoid vaccine in randomised controlled field trial. Lancet. 1990; 336(8720): 891-4; Olanratmanee T, Levine M, Losonsky G, Thisyakorn V, Cryz S J, Jr. Safety and immunogenicity of *Salmonella* Typhi Ty21a liquid formulation vaccine in 4- to 6-year-old Thai children. J Infect Dis. 1992; 166(2): 451-2). Finally, safety of live attenuated vaccines needs to be determined in immunocompromised subjects, and also the very young, prior to widespread use.

Use of a guaBA mutation as the primary attenuating mutation in a live *Shigella* vaccine has been shown to be safe in volunteers (Kotloff K L, Pasetti M F, Barry E M, Nataro J P, Wasserman S S, Sztein M B, et al. Deletion in the *Shigella* enterotoxin genes further attenuates *Shigella flexneri* 2a bearing guanine auxotrophy in a phase 1 trial of CVD 1204 and CVD 1208. J Infect Dis. 2004; 190(10): 1745-54; Kotloff K L, Simon J K, Pasetti M F, Sztein M B, Wooden S L, Livio S, et al. Safety and immunogenicity of CVD 1208S, a live, oral DeltaguaBA Deltasen Deltaset *Shigella flexneri* 2a vaccine grown on animal-free media. Hum Vaccin. 2007: 3(6); 268-75) A phase I clinical trial has shown that S. Paratyphi A CVD 1902 (which possesses deletions in guaBA and clpX was safe and well-tolerated in human volunteers (Levine M M, Galen J, Tennant S, Pasetti M F, Shirley D, Kotloff K, et al. Live oral vaccines to prevent typhoid and paratyphoid fever. 8th International conference on typhoid fever and other invasive Salmonelloses. Dhaka, Baneladesh: 2013).

Although live attenuated S. Typhimurium vaccines have previously been evaluated in clinical studies, they have not progressed further due to the extended shedding of the bacteria in stool in the absence of overt clinical symptoms. Prolonged shedding is a concern for regulatory authorities, due to potential persistence in the environment and the possibility of spreading the vaccine to contraindicated individuals. A candidate S. Typhimurium ΔaroA ΔssaV vaccine called WT05 was shed from the stool of volunteers for up to 21 days (Gordon M A. *Salmonella* infections in immunocompromised adults. J Infect. 2008; 56(6): 413-22). In contrast, *S. Typhi* with the same deletions was only shed for approximately 5 days. The licensed live attenuated bacterial typhoid vaccine, Ty21a, was shed in stools of volunteers for up to 3 days with the majority of isolations occurring 1 day post-vaccination (Graham S M. Salmonellosis in children in developing and developed countries and populations. Curr Opin Infect Dis. 2002; 15(5): 507-12).

A biocontainment system called "delayed lysis" has previously been developed to enhance bacterial lysis and antigen delivery of S. Typhimurium live vector vaccines (Park S E, Pak G D, Aaby P, Adu-Sarkodie Y, Ali M, Aseffa A, et al. The Relationship Between Invasive Nontyphoidal almonella Disease, Other Bacterial Bloodstream Infections, and Malaria in Sub-Saharan Africa. Clin Infect Dis. 2016; 62, Suppl 1: S23-31; Tennant S M, Diallo S, Levy H, Livio S, Sow S O, Tapia M, et al. Identification by PCR of non-typhoidal *Salmonella enterica* serovars associated with invasive infections among febrile patients in Mali. PLoS NeglTrop Dis. 2010; 4(3): e621. Bacteria undergo arabinose-regulated cell lysis after colonization of lymphoid tissue resulting in enhanced delivery of foreign antigens and reduced shedding into the environment. This system comprises 1) an asdA deletion and arabinose-regulated expression of murA to prevent peptidoglycan synthesis, 2) a Δ(gmd-fel) deletion to prevent the formation of a colonic acid capsule, which protects bacteria from lysis from cell wall damage, 3) a ΔrelA deletion which blocks induction of the stringent stress response and subsequent reduction of protein synthesis, 4) plasmid-encoded, arabinose-inducible murA and asdA, and 5) ΔaraBAD and ΔaraE mutations which lead to arabinose accumulation in the cell and an inability to use arabinose which prolongs the time to lysis in vivo. In practice, the bacteria are grown in the presence of arabinose to enable cell wall synthesis and once ingested, the genetically engineered S. Typhimurium invade tissue, where arabinose is absent, murA and asdA expression is switched off, peptidoglycan synthesis ceases, and bacteria lyse. Therefore, it takes multiples mutations and very complex genetic engineering to achieve the "delayed lysis" phenotype.

What is needed are simplified yet highly efficient biocontainment strategies to enable safe and effective use of live attenuated vaccines, including NTS vaccines.

SUMMARY OF THE INVENTION

It is to be understood that both the foregoing general description of the embodiments and the following detailed description are exemplary, and thus do not restrict the scope of the embodiments.

It is an object of the present invention to engineer a biocontainment strategy that efficiently blocks fecal shedding and post-vaccination transmission of live vaccines.

In one aspect, the invention provides a genetically modified microorganism with reduced transmissibility, wherein the microorganism has been genetically modified to express a single stranded binding protein (SSB) regulated by an arabinose responsive promoter, wherein the microorganism has a tightly restricted growth capacity in the absence of arabinose.

In some embodiments, the arabinose responsive promoter is a $P_{BAD}$ promoter.

In some embodiments, the microorganism has been modified to express AraC.

In some embodiments, the $P_{BAD}$ promoter replaces the wild-type $P_{ssb}$ promoter.

In some embodiments, the microorganism has been further modified to reduce expression of endogenous AraB, AraA, and/or AraD.

In some embodiments, the endogenous araBAD operon is deleted in the microorganism.

In some embodiments, the microorganism is modified with a synthetic cassette comprising the $P_{BAD}$ promoter and encoding AraC.

In some embodiments, the synthetic cassette further encodes a gene that confers resistance to an antibiotic. In some embodiments, the gene confers resistance to kanamycin. In some embodiments, the gene is aph. In some embodiments, the sequence of the antibiotic resistance gene is flanked by FRT recombination sites. In some embodiments, the antibiotic resistance gene is removed by a FLP recombinase.

In some embodiments, the microorganism is a pathogenic microorganism. In some embodiments, the microorganism is *Salmonella enterica*. In some embodiments, the *Salmonella enterica* is a typhoidal *Salmonella* strain. In some embodiments, the *Salmonella enterica* is S. Typhi. In some embodiments, the *Salmonella enterica* is a non-typhoidal *Salmonella* (iNTS) strain. In some embodiments, the non-typhoidal *Salmonella* is selected from S. Typhimurium and S. Enteritidis.

In some embodiments, the microorganism further comprises one or more attenuating mutations. In some embodiments, the microorganism comprises a mutation at a locus selected from the group consisting of guaBA, aroC, aroD, clpP, clpX, htrA, pipA one or more capsular biosynthesis machinery genes, and combinations thereof.

In some embodiments, the genetically modified microorganism is used as a live vaccine. In some embodiments, the genetically modified microorganism expresses one or more heterologous antigens. In some embodiments, the heterologous antigen is from a pathogen.

In another aspect, the invention provides a pharmaceutical composition comprising a genetically modified microorganism of the disclosure and a pharmaceutically acceptable carrier.

In another aspect, the invention provides a method of inducing an immune response in a subject, comprising administering to the subject an immunologically-effective amount of a genetically modified microorganism of the disclosure.

In some embodiments, pharmaceutical composition is orally administered.

In some embodiments, pharmaceutical composition is intranasally administered.

In some embodiments, the genetic modification reduces fecal-oral transmission of the genetically modified microorganism.

In some embodiments, the method comprises administering a combination of genetically modified microorganisms.

In some embodiments, the combination comprises a plurality of non-typhoidal *Salmonella* (iNTS) strains. In some embodiments, the combination comprises S. Typhimurium and S. Enteritidis.

In some embodiments, the subject is first administered the genetically modified microorganism as a prime and is subsequently administered an immunologically-effective amount of the genetically modified microorganism as a boost.

In some embodiments, the genetically modified microorganism expresses a heterologous antigen. In some embodiments, the subject is further administered an immunologically-effective amount of a pharmaceutical composition comprising the heterologous antigen.

In some embodiments, the subject is administered the genetically modified microorganism as a prime and is subsequently administered an immunologically-effective amount of the composition comprising the heterologous antigen as a boost.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The skilled artisan will understand that the drawings, described below, are for illustration purposes only. The drawings are not intended to limit the scope of the present teachings in any way.

FIG. 15. S. Typhimurium D65 with $P_{BAD}$-ssb insertion is highly attenuated.

FIG. 16. Percent of mouse shedders.

DETAILED DESCRIPTION

Figure 1:
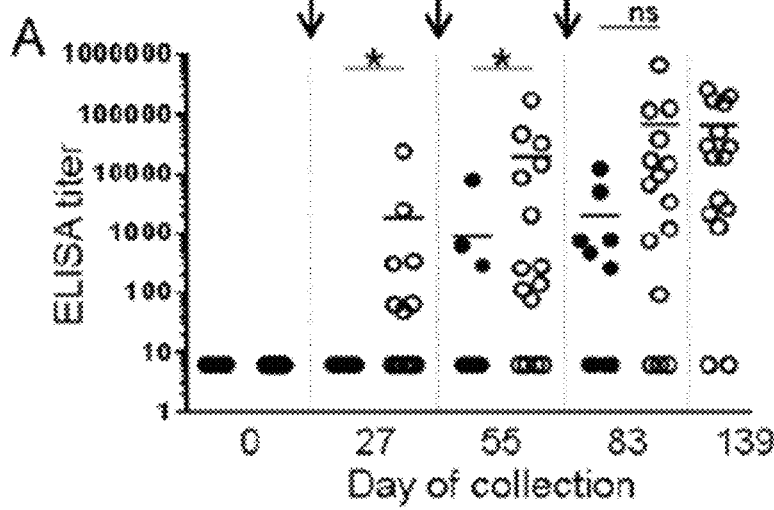
FIG. 1. (A) Anti-LPS serum IgG titers in mice vaccinated with S. Typhimurium CVD 1921 ΔpipA (closed circles) and S. Typhimurium CVD 1926 (open circles). Bar, GMT. Cumulative mortality for (B) mice immunized with CVD 1926 and challenged with 700×LD$_{50}$ at 4 weeks post-vaccination.
Figure 1:
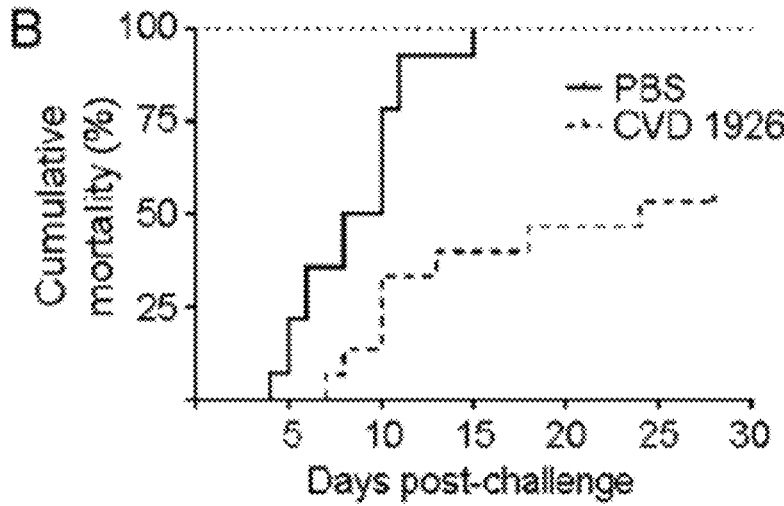

Provided herein is a novel and much simplified alternative to the "delayed lysis" approach described above for biocontainment of live attenuated *Salmonella* vaccines, which is referred to herein as Live Attenuated Non-Transmissible (LANT) vaccines. The present strategy for engineering LANT vaccines focuses on tightly regulated arabinose-controlled synthesis of a single chromosomal gene, ssb, encoding the Single-Stranded Binding protein (SSB) that is essential for DNA replication, recombination, and repair in *Salmonella* (Chase J W, Williams K R. Single-stranded DNA binding proteins required for DNA replication. Annu Rev Biochem. 1986; 55: 103-36; Lohman T M, Ferrari M E. *Escherichia coli* single-stranded DNA-binding protein: multiple DNA-binding modes and cooperativities. Annu Rev Biochem. 1994; 63: 527-70). Despite the simplified strategy, arabinose-regulated LANT strains are still expected to behave similarly to delayed lysis vaccines, undergoing 5-10 rounds of replication in vivo (Curtiss R, 3rd, Wanda S Y, Gunn B M, Zhang X, Tinge S A, Ananthnarayan V, et al. *Salmonella enterica* serovar Typhimurium strains with regulated delayed attenuation in vivo. Infect Immun. 2009; 77(3): 1071-82) following oral administration, thereby allowing sufficient presentation of these vaccine strains to immune inductive sites to elicit pathogen-specific protective immunity. It is noted that arabinose-regulated attenuation of live *Salmonella* vaccines was proven to be safe and immunogenic in a Phase 1 clinical trial, with no vaccine being recovered from stool (Frey S E, Lottenbach K R, Hill H, Blevins T P, Yu Y, Zhang Y, et al. A Phase I, dose-escalation trial in adults of three recombinant attenuated *Salmonella* Typhi vaccine vectors producing *Streptococcus pneumoniae* surface protein antigen PspA. Vaccine. 2013; 31(42): 4874-80).

LANT technology as described herein has several advantages over the delayed lysis approach for biocontainment. First, a non-catalytic structural protein is mutated instead of multiple enzymes. This means that as soon as expression is switched off, bacteria are expected to stop replicating at a rate directly dependent on the half-life of SSB alone. Secondly, since LANT vaccines stop replicating but do not lyse, this allows for protective O polysaccharide and outer membrane proteins to remain intact and properly folded on the outer surface of the vaccine; at this stage, these bacteria resemble intact, inactivated bacterial vaccines (e.g., formalin-inactivated vaccines or bacterial ghost vaccines) (Langemann T, Koller V J, Muhammad A, Kudela P, Mayr U B, Lubitz W. The Bacterial Ghost platform system: production and applications. Bioeng Bugs. 2010; 1(5): 326-36). And finally, although specifically applied in the current disclosure for the creation of either an S. Typhimurium or an S. Enteritidis live attenuated mucosal vaccine, the simplified LANT strategy is expected to be quickly and efficiently applied to the engineering of *Salmonella* vaccines from other serogroups to achieve a multivalent formulation with broad coverage against gastrointestinal disease due to NTS, and would also be applicable to any bacterium amenable to genetic engineering.

Reference will now be made in detail to the presently preferred embodiments of the invention which, together with the drawings and the following examples, serve to explain the principles of the invention. These embodiments are described in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

The practice of the present invention employs, unless otherwise indicated, conventional techniques of molecular biology (including recombinant techniques), microbiology, cell biology, biochemistry and immunology, which are within the skill of the art. Such techniques are explained fully in the literature. See, e.g., Sambrook et al. *Molecular Cloning: A Laboratory Manual, 2nd edition* (1989); *Current Protocols in Molecular Biology* (F. M. Ausubel et al. eds. (1987)); the series *Methods in Enzymology* (Academic Press, Inc); PCR: A Practical Approach (M. MacPherson et al. IRL Press at Oxford University Press (1991)); PCR 2: *A Practical Approach* (M. J. MacPherson, B. D. Hames and G. R. Taylor eds. (1995)); *Antibodies, A Laboratory Manual* (Harlow and Lane eds. (1988)); *Using Antibodies, A Laboratory Manual* (Harlow and Lane eds. (1999)); and *Animal Cell Culture* (R. I. Freshney ed. (1987)).

Definitions of common terms in molecular biology may be found, for example, in Benjamin Lewin, *Genes VII*, published by Oxford University Press, 2000 (ISBN 019879276X); Kendrew et al. (eds); *The Encyclopedia of Molecular Biology*, published by Blackwell Publishers, 1994 (ISBN 0632021829); and Robert A. Meyers (ed), *Molecular Biology and Biotechnology: a Comprehensive Desk Reference*, published by Wiley, John & Sons, Inc., 1995 (ISBN 0471186341).

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. As used in the specification and claims, the singular form "a," "an" and "the" include plural references unless the context clearly dictates otherwise. For example, the term "a cell" includes a plurality of cells, including mixtures thereof. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of." As used herein, the term "about" means plus or minus 10% of the numerical value of the number with which it is being used.

In one embodiment, the invention provides a genetically modified microorganism with reduced transmissibility, wherein the microorganism has been genetically modified to express a single stranded binding protein (SSB) regulated by an arabinose responsive promoter, wherein the microorganism has a highly restricted growth capacity in the absence of arabinose.

In some embodiments, the genetically modified microorganism is used as a live vaccine.

As provided herein, the genetically modified microorganisms have a highly restricted growth capacity when they are placed into an environment that lacks arabinose. In some embodiments, the genetically modified microorganisms remain viable but do not further multiply. In some embodiments, the growth capacity is reduced by at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% in the absence of arabinose. Methods for assaying the growth characteristics of microorganisms are known in the art, and can include, e.g., measuring the optical density of a culture at 600 nm or directly assessing viable counts as provided herein.

In some embodiments, the genetically modified microorganism is a pathogenic microorganism.

In some embodiments, the genetically modified microorganism typically belongs to the Enterobaceteriaceae. The Enterobacteria family comprises species from the following genera: *Alterococcus, Aquamonas, Aranicola, Arsenophonus, Brenneria, Budvicia, Buttiauxella, Candidatus Phlomobacter, Cedeceae, Citrobacter, Edwardsiella, Enterobacter, Erwinia, Escherichia, Ewingella, Hafnia, Klebsiella, Kluyvera, Leclercia, Leminorella, Moellerella, Morganella, Obesumbacterium, Pantoea, Pectobacterium, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhbdus, Yersinia*, and *Yokenella*. In certain embodiments, the genetically modified microorganism is typically a pathogenic species of the Enterobaceteriaceae. Due to their clinical significance, *Escherichia coli, Shigella, Edwardsiella, Salmonella, Citrobacter, Klebsiella, Enterobacter, Serratia, Proteus, Morganella, Providencia* and *Yersinia* are considered to be particularly useful. In other embodiments, the genetically modified microorganism may be a species or strain commonly used for a vaccine.

Some embodiments of the instant invention comprise a species or subspecies of the *Salmonella* genera. For instance, the genetically modified microorganism may be a *Salmonella enterica* serovar.

Figure 8:
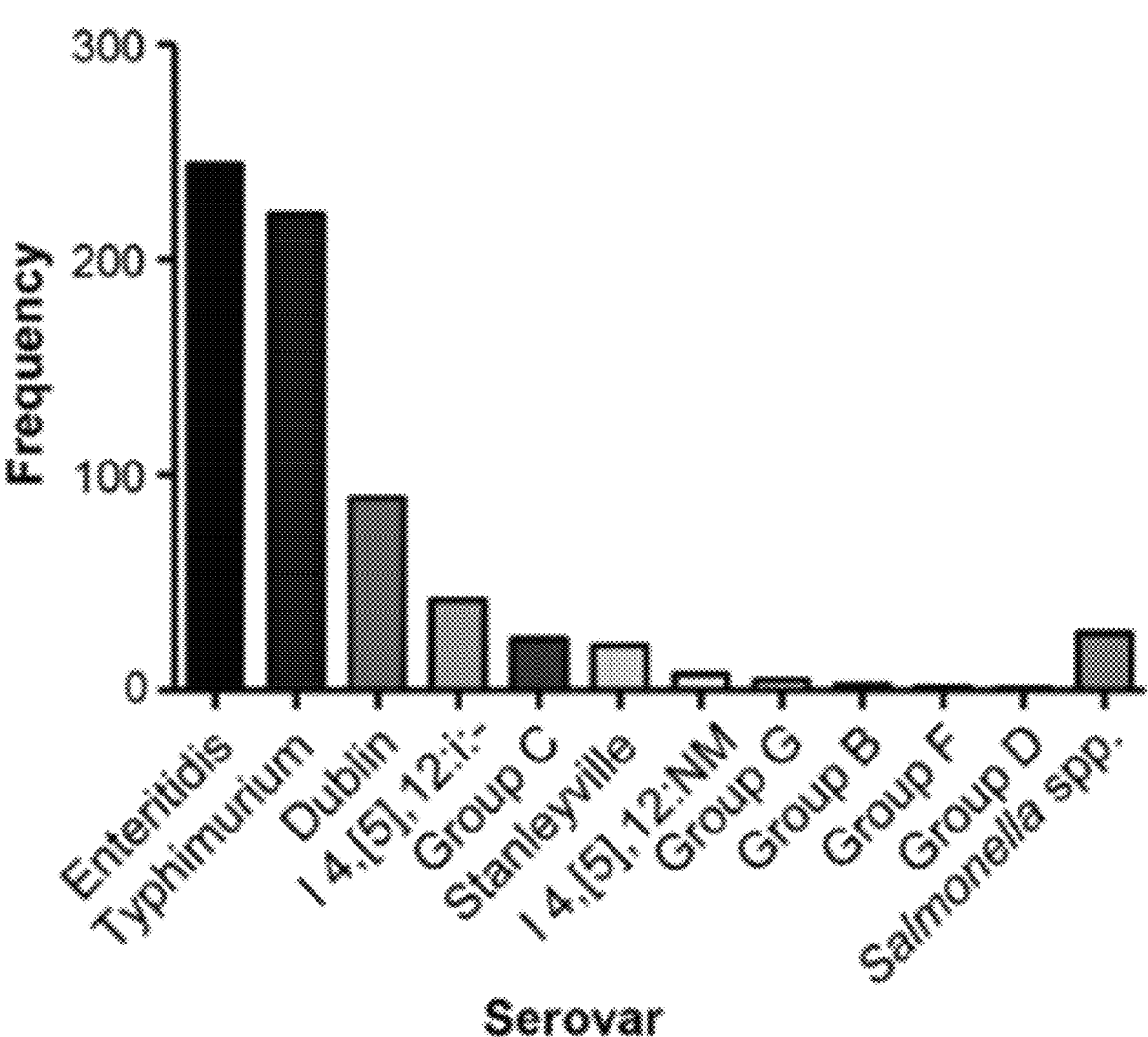
FIG. 8. Serovar distribution of iNTS isolates in Mali.[3]

In some embodiments, the *Salmonella enterica* is a non-typhoidal *Salmonella* (iNTS) strain. In some embodiments, the genetically modified microorganism is selected from S. Typhimurium and S. Enteritidis. In some embodiments, the genetically modified microorganism is selected from one of the strains as shown in FIG. 8.

In some embodiments, the genetically modified microorganism of the invention may be derived from S. Typhimurium, *S. Typhi, S. Paratyphi A, S. Paratyphi B, S. Paratyphi C, S. Gallinarum, S. Enteritidis, S. Choleraesius, S. Arizona, S. Newport, S. Virchow, S. Muenchen* or *S. Dublin*.

Combinations of genetically modified *Salmonella* serovars can also be employed, e.g., to make multivalent vaccines. For example, the combination can include a plurality of iNTS strains, such as S. Typhimurium, S. Enteritidis and any of the strains listed in FIG. 8.

In some embodiments, the genetically modified *Salmonella* can be derived from S. Typhimurium CVD 1921 and/or S. Enteritidis CVD 1941, derived from wild type strains 177 and R11 respectively, isolated from toddlers in Mali with bacteraemia. These strains were constructed by deleting chromosomal guaBA (controlling guanine nucleotide biosynthesis) and clpPX (encoding a regulatory protease) (Tennant S M, Wang J Y, Galen J E, Simon R, Pasetti M F, Gat 0, et al. Engineering and preclinical evaluation of attenuated nontyphoidal *Salmonella* strains serving as live oral vaccines and as reagent strains. Infect Immun. 2011; 79(10): 4175-85).

In some embodiments, a *Salmonella enterica* serovar Typhi strain is used and is genetically modified as described herein. The *Salmonella* Typhi strain that can be used in the present invention is not limiting. For example, it can include any particular strain that has been genetically attenuated from the original clinical isolate Ty2 or other clinical isolates. Any attenuated *Salmonella* Typhi strain can be used as a live vector in accordance with the invention. "Live vector" as used herein refers to attenuated vaccine strains which encode and express sufficient amounts of foreign proteins, from unrelated human pathogens, for efficient delivery and induction of relevant immunity against the unrelated human pathogen. Non-limiting, exemplary attenuated *Salmonella* Typhi strains include S. Typhi Ty21a, CVD 908, S. Typhi CVD 909, CVD 908-htrA, CVD 915, and CVD 910. In some embodiments, the S. Typhi strain can carry one or more additional chromosomal mutations in an essential gene that is expressed on a plasmid. In some embodiments, the plasmid also encodes a heterologous protein that can be an antigen in accordance with the invention, enabling selection and genetic stabilization of the plasmid and preventing loss in S. Typhi.

A genetically modified microorganism of the invention derived from *Salmonella* may be particularly suited to use as a vaccine. Infection of a host with a *Salmonella* strain typically leads to colonization of the gut-associated lymphoid tissue (GALT) or Peyer's patches, which leads to the induction of a generalized mucosal immune response to the recombinant bacterium. Further penetration of the bacterium into the mesenteric lymph nodes, liver and spleen may augment the induction of systemic and cellular immune responses directed against the bacterium. Thus the use of recombinant *Salmonella* for oral immunization stimulates all three compartments of the immune system, which is particularly important for immunizing against infectious disease agents that colonize on and/or invade through mucosal surfaces.

The present disclosure encompasses a genetically modified microorganism with a reduced growth capacity in the absence of arabinose and in some embodiments the microorganism is further attenuated. "Attenuated," as used herein, refers to the state of the microbe wherein the microbe has been weakened from its wild-type fitness by some form of recombinant or physical manipulation. This includes altering the genotype of the microbe to reduce its ability to cause disease.

Methods of attenuation are known in the art. For instance, attenuation may be accomplished by altering (e.g., deleting) native nucleic acid sequences found in the wild type microbe. For instance, if the microbe is *Salmonella*, non-limiting examples of nucleic acid sequences which may be used for attenuation include: pab, pur, aro, asd, nadA, pncB, galE, pmi, fur, rpsL, ompR, htrA, hemA, cdt, cya, crp, dam, phoP, phoQ, rfc, poxA, galU, mviA, sodC, recA, ssrA, sirA, inv, hilA, rpoE, flgM, tonB, slyA, and any combination thereof. Exemplary attenuating mutations may be aroA, aroC, aroD, cdt, cya, crp, guaBA, phoP, phoQ, ompR, galE, ssaV, clpP, clpX pipA, and htrA.

In some embodiments, the microorganism comprises a mutation at a locus selected from the group consisting of guaBA, aroC, aroD, clpP, clpX, htrA, pipA, one or more capsular biosynthesis machinery genes and combinations thereof.

The genetically modified microorganism expresses a single stranded binding protein (SSB) regulated by an arabinose responsive promoter. In some embodiments, the microorganism's endogenous ssb gene has been inactivated or deleted, and a new ssb gene has been inserted into a plasmid. The ssb gene that is inserted is preferably from the same species of microorganism, but can include variant nucleic acid sequences as well as ssb nucleic acid sequences from other organisms. In some embodiments, the promoter of the endogenous ssb gene is inactivated or replaced with a promoter that is responsive to arabinose. In this embodiment, all of the native ssb coding sequence can be left intact. In some embodiments, the promoter of the plasmid-encoded ssb gene is replaced with a promoter that is responsive to arabinose. In this embodiment, all of the native ssb coding sequence is deleted.

The biochemistry and metabolic roles of the *E. coli* SSB protein have been extensively reviewed in Lohman et al., *Annual Reviews in Biochemistry* 63:527, 1994 and Chase et al., *Annual Reviews in Biochemistry* 55:103, 1986 (the disclosures of which are incorporated herein by reference).

SSB (from *E. coli*) is a non-catalytic 177 amino acid protein, with a relative molecular weight of 19 kDa, that binds with high affinity to single-stranded DNA (ssDNA), and plays an essential role as an accessory protein in DNA replication, recombination, and repair. The biologically relevant form of SSB involved in binding to ssDNA is a tetramer, which binds in two modes to ssDNA, intimately associating with an average of either 35 ($SSB_{35}$-binding mode) or 65 bases ($SSB_{65}$-binding mode). The specific conditions controlling the preferred mode of binding are complex and depend on the surrounding concentration of monovalent and divalent salts, pH, and temperature, as well as the amount of SSB protein present. Under given conditions, high concentrations of SSB favor the $SSB_{35}$-binding mode, with lower SSB concentrations favoring the $SSB_{65}$-mode. However, it must be emphasized that in both binding modes, the required conformation of SSB is a tetramer.

In some embodiments, the ssb gene is from S. Typhimurium. In some embodiments, the coding sequence comprises SEQ ID NO:1 and the amino acid sequence comprises SEQ ID NO:2.

As provided herein, expression of the SSB is regulated by an arabinose responsive promoter. The term "promoter," as used herein, may mean a synthetic or naturally-derived DNA sequence which is capable of conferring, activating or enhancing expression of a nucleic acid in a cell. A promoter may comprise one or more specific transcriptional regulatory sequences to further enhance expression and/or to alter the spatial expression and/or temporal expression of same.

Generally speaking, arabinose may be present during the in vitro growth of the genetically modified microorganism, while typically absent in host tissue. In one embodiment, the promoter is derived from an araC-$P_{BAD}$ system. The araC-$P_{BAD}$ system is a tightly regulated expression system which has been shown to work as a strong promoter induced by the addition of low levels of arabinose. See., e.g., Guzman L M, Belin D, Carson M J, & Beckwith J (1995) Tight regulation, modulation, and high-level expression by vectors containing the arabinose PBAD promoter. *J Bacteriol* 177: 4121-4130. The araC-araBAD promoter is a bidirectional promoter controlling expression of the araBAD nucleic acid sequences in one direction, and the araC nucleic acid sequence in the other direction. For convenience, the portion of the araC-araBAD promoter that mediates expression of the araBAD nucleic acid sequences, and which is controlled by the araC nucleic acid sequence product, is referred to herein as $P_{BAD}$. For use as described herein, in some embodiments, a cassette with the araC nucleic acid sequence and the araC-araBAD promoter may be used. This cassette is referred to herein as the araC-P BAD promoter. The AraC protein is both a positive and negative regulator of $P_{BAD}$. In the presence of arabinose, the AraC protein is a positive regulatory element that allows expression from $P_{BAD}$. In the absence of arabinose, the AraC protein represses expression from $P_{BAD}$. This can lead to a 1,200-fold difference in the level of expression from $P_{BAD}$.

Other enteric bacteria contain arabinose regulatory systems homologous to the araCaraBAD system from *E. coli*. For example, there is homology at the amino acid sequence level between the *E. coli* and the S. Typhimurium AraC proteins, and less homology at the DNA level. However, there is high specificity in the activity of the AraC proteins. For example, the *E. coli* AraC protein activates only *E. coli* $P_{BAD}$ (in the presence of arabinose) and not S. Typhimurium $P_{BAD}$. Thus, an arabinose regulated promoter may be used in a recombinant bacterium that possesses a similar arabinose operon, without substantial interference between the two, if the promoter and the operon are derived from two different species of bacteria.

In some embodiments, the arabinose responsive promoter (e.g., $P_{BAD}$) is useful for regulating expression of the ssb gene in *Salmonella*. In some embodiments, the *Salmonella* is a nontyphoidal *Salmonella*, such as S. Typhimurium and/or S. Enteritidis.

In some embodiments, the nucleotide sequence of the araC-$P_{BAD}$ system for use in the present invention comprises SEQ ID NO:3.

In some embodiments, AraC protein is from S. Typhimurium. In some embodiments, the amino acid sequence of AraC is SEQ ID NO:4.

In some embodiments, the genetically modified microorganism is modified with a synthetic cassette comprising the $P_{BAD}$ promoter and encoding AraC.

In some embodiments, the endogenous $P_{ssb}$ promoter is deleted and is replaced by the araC-$P_{BAD}$ promoter. In some embodiments the endogenous $P_{ssb}$ promoter is inactivated by one or more deletions and/or point mutations, and the araC-$P_{BAD}$ promoter is inserted adjacent to the ssb gene. In some embodiments, a cassette comprising the ssb gene and arabinose responsive promoter (e.g., araC-$P_{BAD}$ promoter) is provided on a plasmid. In some embodiments, a cassette comprising the ssb gene and arabinose responsive promoter (e.g., $P_{BAD}$ promoter) is integrated into the genome of the microorganism. In some embodiments, the genetically modified microorganism has been further modified to reduce or eliminate expression of its endogenous AraB, AraA, and/or AraD proteins. In some embodiments, the endogenous araBAD operon is deleted in the microorganism.

In some embodiments, the synthetic cassette comprising the arabinose responsive promoter further encodes a gene that confers resistance to an antibiotic. In some embodiments, the gene confers resistance to kanamycin. In some embodiments, the gene is aph. In some embodiments, the sequence of the antibiotic resistance gene is flanked by FRT recombination sites. In some embodiments, the antibiotic resistance gene is removed by a FLP recombinase.

In some embodiments, the synthetic cassette comprises SEQ ID NO:5.

In some embodiments, the concentration of arabinose necessary to induce expression is typically less than about 2%. In some embodiments, the concentration is less than about 1.5%, 1%, 0.5%, 0.2%, 0.1%, or 0.05%. In other embodiments, the concentration is 0.05% or below, e.g. about 0.04%, 0.03%, 0.02%, or 0.01%. In an exemplary embodiment, the concentration is about 0.05%.

In some embodiments, the genetically modified microorganism expresses one or more antigens. In some embodiments, the antigen can be native to the genetically modified microorganism. In some embodiments, the antigen is over-expressed in the microorganism in order to improve immunogenicity. In some embodiments, the antigen is heterologous and is not native to the microorganism.

As used herein, "antigen" refers to a biomolecule capable of eliciting an immune response in a host. In some embodiments, an antigen may be a protein, or fragment of a protein. In an exemplary embodiment, the antigen elicits a protective immune response. As used herein, "protective" means that the immune response contributes to the lessening of any symptoms associated with infection of a host with the pathogen the antigen was derived from or designed to elicit a response against. For example, a protective antigen from a pathogen, such as *Salmonella*, may induce an immune response that helps to ameliorate symptoms associated with *Salmonella* infection or reduce the morbidity and mortality associated with infection with the pathogen. The use of the term "protective" in this invention does not necessarily require that the host is completely protected from the effects of the pathogen.

In some embodiments, the heterologous antigen is from a pathogen. Antigens may be from bacterial, viral, mycotic and parasitic pathogens, and may be designed to protect against bacterial, viral, mycotic, and parasitic infections, respectively.

In another alternative, antigens may be tumor antigens, and may be designed to decrease tumor growth. It is specifically contemplated that antigens from organisms newly identified or newly associated with a disease or pathogenic condition, or new or emerging pathogens of animals or humans, including those now known or identified in the future, may be expressed by a microorganism detailed herein. Furthermore, antigens for use in the invention are not limited to those from pathogenic organisms. Immunogenicity of the microorganism may be augmented and/or modulated by constructing strains that also express sequences for cytokines, adjuvants, and other immunomodulators.

In some embodiments, the antigen is from the pathogen *Acinetobacter baumannii*. In some embodiments, the pathogen is from *Klebsiella pneumoniae*. In some embodiments, the pathogen is a bacterial or viral pathogen. In some embodiments, the pathogen is selected from the group consisting of *Streptococcus pneumonia, Neisseria meningitidis, Haemophilus influenzae, Klebsiella* spp., *Pseudomonas* spp., *Salmonella* spp., *Shigella* spp., Group B streptococci, *Bacillus anthracis* adenoviruses; *Bordetella pertussus; Clostridium* spp; bovine rhinotracheitis; *Brucella* spp; *Branhamella catarrhalis*; canine hepatitis; canine distemper; Chlamydiae; coccidiomycosis; cowpox; tularemia; filoviruses; arenaviruses; bunyaviruses; cytomegalovirus; cytomegalovirus; Dengue fever; dengue toxoplasmosis; Diphtheria; encephalitis; Enterotoxigenic *Escherichia coli*;

Epstein Barr virus; equine encephalitis; equine infectious anemia; equine influenza; equine pneumonia; equine rhinovirus; feline leukemia; flavivirus; *Burkholderia mallei*; Globulin; *Haemophilus influenzae* type b; *Haemophilus influenzae; Haemophilus pertussis; Helicobacter pylori*; Hemophilus spp; hepatitis; hepatitis A; hepatitis B; Hepatitis C; herpes viruses; HIV; HIV-1 viruses; HIV-2 viruses; HTLV; Influenza; Japanese encephalitis; *Klebsiella* spp. *Legionella pneumophila; leishmania; leprosy*; lyme disease; malaria immunogen; measles; meningitis; meningococcal; Meningococcal Polysaccharide Group A, Meningococcal Polysaccharide Group C; mumps; Mumps Virus; mycobacteria; Mycobacterium tuberculosis; *Neisseria* spp; *Neisseria gonorrhoeae*; ovine blue tongue; ovine encephalitis; papilloma; SARS and associated coronaviruses such as SARS-CoV-2; parainfluenza; paramyxovirus; paramyxoviruses; *Bordetella* spp; *Yersinia* spp; *Coxiella bumetti; Pneumococcus* spp; *Pneumocystis carinii*; Pneumonia; Poliovirus; *Proteus* species; *Pseudomonas aeruginosa*; rabies; respiratory syncytial virus; rotavirus; Rubella; Salmonellae; schistosomiasis; Shigellae spp; simian immunodeficiency virus; Smallpox; *Staphylococcus aureus; Staphylococcus* spp; *Streptococcus pyogenes; Streptococcus* spp; swine influenza; tetanus; *Treponema pallidum*; Vaccinia; varicella-zoster virus; and *Vibrio cholerae* and combinations thereof.

In some embodiments, the antigen is the spike protein or an antigenic fragment or variant thereof from Severe Acute Respiratory Syndrome Coronavirus 2 (SARS-CoV-2). In some embodiments, the spike protein has the sequence found in GenBank accession no.: QIC53213.1. In some embodiments, the amino acid sequence is SEQ ID NO:6 and the nucleotide sequence is SEQ ID NO:7.

Certain embodiments encompass an allergen as an antigen. Allergens are substances that cause allergic reactions in a host that is exposed to them. Allergic reactions, also known as Type I hypersensitivity or immediate hypersensitivity, are vertebrate immune responses characterized by IgE production in conjunction with certain cellular immune reactions. Many different materials may be allergens, such as animal dander and pollen, and the allergic reaction of individual hosts will vary for any particular allergen. It is possible to induce tolerance to an allergen in a host that normally shows an allergic response. The methods of inducing tolerance are well-known and generally comprise administering the allergen to the host in increasing dosages.

In some embodiments, the antigen to be expressed can be integrated into the chromosome of the genetically modified microorganism. In some embodiments, the antigen can be expressed on a plasmid.

In some embodiments, the genetically modified microorganism such as S. Typhi, can have a disruption in one or more loci that causes an attenuated phenotype, and the antigen to be expressed can be inserted into said loci. In some embodiments, the loci is selected from the guaBA locus, the htrA locus, the rpoS locus, and the ssb locus. See, e.g., U.S. Pat. No. 10,010,596, which is incorporated herein by reference. In a particular embodiments, the antigen of interest is one or more of the cell binding domain of C. *difficile* toxin A (CBD/A), the cell binding domain of C. *difficile* toxin B (CBD/B), the cell binding domain of C. *difficile* binary toxin (BT), the LcrV antigen of *Yersinia pestis* and the capsular F1 antigen of *Yersinia pestis*. In a further aspect, each chromosomal-based expression system comprises an antigen expression cassette encoding a different antigen of interest. In another aspect of this embodiment, the antigen-encoding attenuated strain of S. Typhi is the strain CVD 910 which has disruptions of the guaBA locus, the htrA locus, and the rpoS locus, and which has a chromosomal-based expression system integrated into each site of disruption that encodes one or more antigens of interest. In a particular aspect, the antigen-encoding attenuated strain of S. Typhi is the strain CVD 910-3A which has disruptions of the guaBA locus, the htrA locus, and the rpoS locus, and which comprises antigen expression cassettes integrated into the locations of chromosomal disruption, wherein each antigen expression cassette encodes the cell binding domain of *C. difficile* toxin A.

If heterologous antigens or other proteins are overexpressed using plasmids, plasmid stability can be a key factor in the development of high quality attenuated vaccines. Plasmidless bacterial cells tend to accumulate more rapidly than plasmid-bearing cells. One reason for this increased rate of accumulation is that the transcription and translation of plasmid genes imposes a metabolic burden which slows cell growth and gives plasmidless cells a competitive advantage. Furthermore, foreign plasmid gene products are sometimes toxic to the host cell. Thus, it is advantageous for the plasmid to be under some form of selective pressure, in order to ensure that the encoded antigens are properly and efficiently expressed, so that a robust and effective immune response can be achieved.

In some embodiments, the plasmid is selected using a non-antibiotic selection system. For example, the plasmid can encode an essential gene that complements an otherwise lethal deletion/mutation of this locus from the live vector chromosome. It is not necessary that the genetically modified microorganism comprise the complete nucleic acid sequence of the antigen. It is only necessary that the antigen sequence used be capable of eliciting an immune response. The antigen may be one that was not found in that exact form in the parent organism. For example, a sequence coding for an antigen comprising 100 amino acid residues may be transferred in part into a genetically modified microorganism herein so that a peptide comprising only 75, 65, 55, 45, 35, 25, 15, or even 10, amino acid residues is produced by the genetically modified microorganism. Alternatively, if the amino acid sequence of a particular antigen or fragment thereof is known, it may be possible to chemically synthesize the nucleic acid fragment or analog thereof by means of automated nucleic acid sequence synthesizers, PCR, or the like and introduce said nucleic acid sequence into the appropriate copy number vector.

In some embodiments, the antigen is a polypeptide. In some embodiments, the antigen is a fragment or variant sequence. The antigenic fragment can be "free-standing," or comprised within a larger polypeptide of which they form a part or region, most preferably as a single continuous region.

In some embodiments, the antigenic fragment can include, for example, truncation polypeptides having the amino acid sequence of a polypeptide, except for deletion of a continuous series of residues that includes the amino terminus, or a continuous series of residues that includes the carboxyl terminus or deletion of two continuous series of residues, one including the amino terminus and one including the carboxyl terminus. In some embodiments, fragments are characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, and high antigenic index regions.

The fragment can be of any size. An antigenic fragment is capable of inducing an immune response in a subject or be recognized by a specific antibody. In some embodiments, the fragment corresponds to an amino-terminal truncation mutant. In some embodiments, the number of amino terminal amino acids missing from the fragment ranges from 1-100 amino acids. In some embodiments, it ranges from 1-75 amino acids, 1-50 amino acids, 1-40 amino acids, 1-30 amino acids, 1-25 amino acids, 1-20 amino acids, 1-15 amino acids, 1-10 amino acids and 1-5 amino acids.

In some embodiments, the fragment corresponds to carboxyl-terminal truncation mutant. In some embodiments, the number of carboxyl terminal amino acids missing from the fragment ranges from 1-100 amino acids. In some embodiments, it ranges from 1-75 amino acids, 1-50 amino acids, 1-40 amino acids, 1-30 amino acids, 1-25 amino acids, 1-20 amino acids, 1-15 amino acids, 1-10 amino acids and 1-5 amino acids.

In some embodiments, the fragment corresponds to an internal fragment that lacks both the amino and carboxyl terminal amino acids. In some embodiments, the fragment is 7-200 amino acid residues in length. In some embodiments, the fragment is 10-100 amino acid residues, 15-85 amino acid residues, 25-65 amino acid residues or 30-50 amino acid residues in length. In some embodiments, the fragment is 7 amino acids, 10 amino acids, 12 amino acids, 15 amino acids, 20 amino acids, 25 amino acids, 30 amino acids, 35 amino acids, 40 amino acids, 45 amino acids, 50 amino acids 55 amino acids, 60 amino acids, 80 amino acids or 100 amino acids in length.

In some embodiments, the fragment is at least 50 amino acids, 100 amino acids, 150 amino acids, 200 amino acids or at least 250 amino acids in length. Of course, larger antigenic fragments are also useful according to the present invention, as are fragments corresponding to most, if not all, of the amino acid sequence of a polypeptide from which it is derived.

In some embodiments, the polypeptides have an amino acid sequence at least 80, 85%, 90%, 91%, 92%, 93%, 94%, 95%, 96%, 97%, 98%, 99%, or 100% identical to the polypeptides described herein or antigenic or biologically active fragments thereof. In some embodiments, the variants are those that vary from the reference by conservative amino acid substitutions, i.e., those that substitute a residue with another of like characteristics. Typical substitutions are among Ala, Val, Leu and Ile; among Ser and Thr; among the acidic residues Asp and Glu; among Asn and Gln; and among the basic residues Lys and Arg, or aromatic residues Phe and Tyr. In some embodiments, the polypeptides are variants in which several, 5 to 10, 1 to 5, or 1 to 2 amino acids are substituted, deleted, or added in any combination.

In some embodiments, the polypeptides are encoded by polynucleotides that are optimized for high level expression in the microorganism, such as *Salmonella*, using codons that are preferred in the microorganism. As used herein, a codon that is "optimized for high level expression refers to a codon that is relatively more abundant in the microorganism in comparison with all other codons corresponding to the same amino acid. In some embodiments, at least 10% of the codons are optimized for high level expression. In some embodiments, at least 25%, at least 50%, at least 75%, at least 80%, at least 85%, at least 90%, at least 95%, or at least 99% of the codons are optimized for high level expression.

In some embodiments, the genetically modified microorganism comprises a system for exporting a protein of interest, such as an antigen. In some aspects, the system comprises an expression vector comprising an expression cassette, wherein the expression cassette comprises an export protein coding sequence genetically fused to a protein of interest coding sequence, a host cell transformed with the expression vector, and a culturing environment for the transformed host cell, wherein the expression cassette expresses an export protein::protein of interest fusion protein, which is exported out of the transformed host cell. In some embodiments the export protein is a *Salmonella enterica* serovar Typhi cytolysin A (ClyA) protein having substantially reduced hemolytic activity. See, e.g., U.S. Pat. No. 9,051,574, which is incorporated by reference.

In some embodiments, the microorganism that can be modified is as described in WO 2018/213242 A1 (incorporated by reference herein), corresponding to *Salmonella* that has been engineered to express a heterologous antigen from a pathogen, wherein the heterologous antigen comprises an outer membrane protein, an antigenic fragment thereof or a variant thereof, wherein the antigen is delivered to a mucosal tissue of the subject by an outer membrane vesicle. In some embodiments, the heterologous antigen comprises an antigen useful for protection against pneumonic and systemic infections caused by *Acinetobacter baumannii* or *Klebsiella pneumoniae*. Isolated recombinant outer membrane vesicles from the *Salmonella* Typhi vectors as described by WO 2018/213242 A1 can also be used in conjunction with the genetically modified microorganisms as described herein in vaccination methods, e.g., in prime/boost vaccination strategies.

In some embodiments, the invention provides a live *Salmonella* Typhi vector modified as described herein, wherein the *Salmonella* Typhi vector expresses OmpA, an antigenic fragment thereof or a variant thereof from *Acinetobacter baumannii*; and/or OmpW, an antigenic fragment thereof or a variant thereof from *Acinetobacter baumannii*. In some embodiments, the invention provides a live *Salmonella* Typhi vector modified as described herein, wherein the *Salmonella* Typhi vector expresses OmpA, an antigenic fragment thereof or a variant thereof from *Klebsiella pneumoniae*; and/or OmpW, an antigenic fragment thereof or a variant thereof from *Klebsiella pneumoniae*.

In some embodiments, the antigen is OmpW from *Acinetobacter baumannii*. In some embodiments the nucleotide and amino acid sequence of OmpW from *Acinetobacter baumannii* corresponds to SEQ ID NOS:12 and 13, respectively. In some embodiments, the outer membrane protein is OmpW from *Klebsiella pneumoniae*. In some embodiments the nucleotide and amino acid sequence of OmpW from *Klebsiella pneumoniae* corresponds to SEQ ID NOS:14 and 15, respectively.

In some embodiments, the antigen is OmpA from *Acinetobacter baumannii*. In some embodiments the nucleotide and amino acid sequence of OmpA from *Acinetobacter baumannii* corresponds to SEQ ID NOS:8 and 9, respectively In some embodiments, the outer membrane protein is OmpA from *Klebsiella pneumoniae*. In some embodiments the nucleotide and amino acid sequence of OmpA from *Klebsiella pneumoniae* corresponds to SEQ ID NOS:10 and 11, respectively.

In some embodiments, the *Salmonella* Typhi vector comprises both OmpW and OmpA from *Acinetobacter baumannii* or *Klebsiella pneumoniae*.

In some embodiments, a combination of *Salmonella* Typhi vectors expressing antigens from *Acinetobacter baumannii* and *Klebsiella pneumoniae* can be employed.

In some embodiments, the invention provides a composition comprising a combination of isolated recombinant outer membrane vesicles from the engineered *Salmonella* Typhi vectors as described herein. In some embodiments, the combination comprises a first isolated recombinant outer membrane vesicle comprising i) OmpA, an antigenic fragment thereof or a variant thereof from *Acinetobacter baumannii*; and ii) OmpW, an antigenic fragment thereof or a variant thereof from *Acinetobacter baumannii*; and a second isolated recombinant outer membrane vesicle comprising i) OmpA, an antigenic fragment thereof or a variant thereof from *Klebsiella pneumoniae*; and ii) OmpW, an antigenic fragment thereof or a variant thereof from *Klebsiella pneumoniae*, wherein the *Salmonella* Typhi vectors have been engineered to express the antigens.

In some embodiments, the genetically modified microorganism comprises a *Salmonella* Typhi live vector comprising the cell binding domain of TcdA toxin (CBD/A) of *Clostridium difficile* or an antigenic fragment thereof and the cell binding domain of TcdB toxin (CBD/B) of *Clostridium difficile* or an antigenic fragment thereof and optionally the cell-binding subunit component (CdtB) of binary toxin of *Clostridium difficile* or an antigenic fragment thereof. See, e.g., U.S. Pat. No. 10,046,040, which is incorporated by reference herein.

Therapeutic Methods

In another embodiment, the invention provides a method of inducing an immune response in a subject, comprising administering to the subject an immunologically-effective amount of a genetically modified microorganism as provided herein.

In some embodiments, the genetically modified microorganism expresses a heterologous antigen. In some embodiments, the subject is further administered an immunologically-effective amount of a pharmaceutical composition comprising an antigen expressed by the genetically modified microorganism, e.g., a heterologous antigen.

In some embodiments, a combination of genetically modified microorganisms is administered to the subject. In some embodiments, the combination comprises a plurality of non-typhoidal *Salmonella* (NTS) strains. In some embodiments, the combination comprises S. Typhimurium, *S. Enteritidis* and any of the strains listed in FIG. 8.

In some embodiments, the subject is administered genetically modified S. Typhimurium and S. Enteritidis as provided herein, in combination with conjugate vaccines derived from S. Typhimurium and S. Enteritidis, wherein the conjugate comprises an O polysaccharide covalently linked to a flagellin protein. See, e.g., U.S. Pat. No. 9,050,283, which is incorporated by reference.

In some embodiments, the subject is administered a combination of genetically modified microorganisms that are *Salmonella enterica* serovars, such as S. Typhimurium (serogroup B), S. Enteritidis (serogroup D), S. Choleraesuis (serogroup C), S. Typhi (serogroup D) and S. Paratyphi A (serogroup A). In some embodiments, the subject is subsequently administered a multivalent *Salmonella enterica* serovar vaccine capable of inducing an immune response comprising a combination of conjugates selected from S. Typhimurium (serogroup B), S. Enteritidis (serogroup D), S. Choleraesuis (serogroup C), S. Typhi (serogroup D) S. Paratyphi A (serogroup A), wherein the conjugates comprise a hapten antigen and a carrier antigen, wherein at least one of the hapten antigens or carrier antigens is from the *Salmonella enterica* serovar. In some embodiments, the multivalent vaccine further comprises a conjugate from *Salmonella enterica* serovar S. Paratyphi B (serogroup B). In some embodiments, the hapten of the serovar conjugate comprises one or more polysaccharides that are characteristic or isolated from the *Salmonella enterica* serovar. In some embodiments, the hapten for one or more of the conjugates of the multivalent vaccine comprises core-O- polysaccharide (COPS). As used herein, "core-O-polysaccharide" or "COPS," is a polysaccharide in which the lipid A moiety from lipopolysaccharide (LPS) has been removed. In some embodiments, a S. Typhi conjugate comprises Vi capsular polysaccharide as the hapten. The Vi capsular polysaccharide of S. Typhi is a linear homopolymer of poly-alpha(1-4)GalNAcp variably O acetylated at the C-3 position. See, e.g., Tacket et al., J. Infect. Diseases, 190: 565-70 (2004); Szu et al., Infect Immun. 59(12): 4555-4561 (1991). In some embodiments, the antigenic carrier of the serovar conjugate is non-limiting and can comprise, for example, an antigen that is characteristic or isolated from the same *Salmonella enterica* serovar from which the hapten is derived. In some embodiments, the carrier is a phase 1 flagella protein (FliC) that is characteristic of the *Salmonella enterica* serovar. As used herein, the term "phase 1 flagella" and FliC protein are used interchangeably. "Phase 1 flagella" encompasses: 1] phase 1 flagella expressed from biphasic serovars such as S. Typhimurium, where both a phase 1 (FliC) and an additional phase 2 flagella (FljB) are expressed, 2] flagella expressed by monophasic *Salmonella* serovars such as S. Enteritidis, which express only one type of flagella (FliC) and 3] fragments or derivatives of FliC. In some embodiments, the carrier is a mutant of FliC with diminished or no capability to activate host inflammatory responses through its interaction with Toll-like receptor 5 (TLR5). In some embodiments, the carrier is the mutant FliC$^{74114}$, or antigenic fragments thereof which retain the diminished capability to activate host inflammatory responses through TLR5. See, e.g., U.S. Pat. No. 9,011,871, which is incorporated by reference herein.

In some embodiments, the carrier of the conjugate vaccine is not from a *Salmonella enterica* serovar, and includes antigenic carriers typically used in conjugate vaccines. Non-limiting examples of a carrier for one or more conjugates include tetanus toxin/toxoid, NTHi high molecular weight protein, diphtheria toxin/toxoid, detoxified *Pseudomonas aeruginosa* toxin A, cholera toxin/toxoid, pertussis toxin/toxoid, *Clostridium perfringens* exotoxins/toxoid, hepatitis B surface antigen, hepatitis B core antigen, rotavirus VP 7 protein, respiratory syncytial virus F and G protein, detoxified ETEC LT and genetically engineered mutant derivatives, detoxified *Shigella* Stx1/2 and genetically engineered mutants thereof.

In some embodiments, the subject is first administered the genetically modified microorganism as a prime and is subsequently administered an immunologically-effective amount of the genetically modified microorganism and/or a composition comprising the antigen as a boost.

In other aspects of the invention, the genetically modified microorganism is administered as a component of a heterologous prime/boost regimen. "Heterologous prime/boost" strategies are 2-phase immunization regimes involving sequential administration (in a priming phase and a boosting phase) of the same antigen in two different vaccine formulations by the same or different route. In particular aspects of the invention drawn to heterologous prime/boost regimens, a mucosal prime/parenteral boost immunization strategy is used. For example, one or more genetically modified microorganism vaccines as taught herein is administered orally or via some other mucosal route and subsequently boosted parentally with a vaccine composition comprising an antigen expressed by the genetically modified microorganism. In some embodiments, the vaccine composition comprising the antigen comprises isolated recombinant outer membrane vesicles from a *Salmonella* vector (e.g., Typhi) comprising the antigen. Subunit or conjugate vaccine compositions are also contemplated as vaccine compositions comprising the antigen which can be used in heterologous prime/boost strategies.

In some embodiments, the subject is administered the genetically modified microorganism as a prime and is subsequently administered an immunologically-effective amount of the composition comprising the antigen as a boost.

In some embodiments, the invention provides a method of inducing an immune response in a subject in need thereof, comprising administering to the subject an immunologically-effective amount of the genetically modified microorganism as described herein that expresses an antigen of interest, in combination with isolated recombinant outer membrane vesicles from *Salmonella* comprising the antigen of interest (see, e.g., WO 2018/213242 A1), wherein the *Salmonella* has been engineered to express the antigen, wherein the outer membrane vesicle is delivered to a mucosal tissue of the subject.

Vaccine strategies are well known in the art and therefore the vaccination strategy encompassed by the invention does not limit the invention in any manner. In certain aspects of the invention, the genetically modified microorganism vaccine is administered alone in a single application or administered in sequential applications, spaced out over time.

In another aspect, the present invention is directed to methods of inducing an immune response against an antigen in a subject in need thereof, comprising administering to the subject an immunologically-effective amount of a genetically modified microorganism of the invention as a prime, and subsequently administering a boost comprising a composition of isolated recombinant outer membrane vesicles from a *Salmonella* vector (e.g., Typhi) presenting one or more of the antigens.

In some embodiments, a genetically modified S. Typhi live vector vaccine is administered as a prime and is boosted with isolated recombinant outer membrane vesicles from a S. Typhi that expresses the antigen. In some embodiments, isolated recombinant outer membrane vesicles comprising the antigen are administered as a prime and is boosted with a genetically modified microorganism (e.g., S. Typhi) of the invention that expresses the antigen. In some embodiments, the boost is administered mucosally, e.g., orally, or parenterally.

As used herein, an "immune response" is the physiological response of the subject's immune system to an immunizing composition. An immune response may include an innate immune response, an adaptive immune response, or both. In one embodiment of the present invention, the immune response is a protective immune response. A protective immune response confers immunological cellular memory upon the subject, with the effect that a secondary exposure to the same or a similar antigen is characterized by one or more of the following characteristics: shorter lag phase than the lag phase resulting from exposure to the selected antigen in the absence of prior exposure to the immunizing composition; production of antibody which continues for a longer period than production of antibody resulting from exposure to the selected antigen in the absence of prior exposure to the immunizing composition; a change in the type and quality of antibody produced in comparison to the type and quality of antibody produced upon exposure to the selected antigen in the absence of prior exposure to the immunizing composition; a shift in class response, with IgG antibodies appearing in higher concentrations and with greater persistence than IgM, than occurs in response to exposure to the selected antigen in the absence of prior exposure to the immunizing composition; an increased average affinity (binding constant) of the antibodies for the antigen in comparison with the average affinity of antibodies for the antigen resulting from exposure to the selected antigen in the absence of prior exposure to the immunizing composition; and/or other characteristics known in the art to characterize a secondary immune response.

In some embodiments, the immune response is sufficient to confer protective immunity upon the subject against a later infection by the pathogen. In some embodiments, the compositions are administered intranasally.

In some embodiments, one or more genetically modified microorganisms or a composition comprising the antigen (e.g., isolated recombinant outer membrane vesicles harboring the antigen) are mucosally administered in a first priming administration, followed, optionally, by a second (or third, fourth, fifth, etc. . . . ) priming administration of the genetically modified microorganisms or composition comprising the antigen (e.g., isolated recombinant outer membrane vesicles harboring the antigen) from about 2 to about 10 weeks later. In some embodiments, a boosting composition is administered from about 3 to about 12 weeks after the priming administration. In some embodiments, the boosting composition is administered from about 3 to about 6 weeks after the priming administration. In some embodiments, the boosting composition is substantially the same type of composition administered as the priming composition (e.g., a homologous prime/boost regimen).

In practicing immunization protocols for treatment and/or prevention, an immunologically-effective amount of a genetically modified microorganism or composition comprising the antigen is administered to a subject. As used herein, the term "immunologically-effective amount" means the total amount that is sufficient to show an enhanced immune response in the subject. When "immunologically-effective amount" is applied to an individual therapeutic agent administered alone, the term refers to that therapeutic agent alone. When applied to a combination, the term refers to combined amounts of the ingredients that result in the therapeutic effect, whether administered in combination, serially or simultaneously.

The term "subject" as used herein, refers to animals, such as mammals. For example, mammals contemplated include humans, primates, dogs, cats, sheep, cattle, goats, pigs, horses, mice, rats, rabbits, guinea pigs, and the like. The terms "subject," "patient," and "host" are used interchangeably.

In some embodiments, the genetically modified microorganism or compositions herein are administered to one or more subjects in long-term care facilities where vaccination would supplement rigorous antimicrobial stewardship to reduce the incidence of infections both prior to and upon transfer of patients to acute-care hospitals. In some embodiments, subjects can be administered the genetically modified microorganism or compositions prior to discharge from hospitals after treatment for bacterial sepsis, pneumonia, or urinary tract infections, to prevent recurrence due to treatment failure or re-infection with more resistant pathogenic strains. In some embodiments, the subjects are military personnel at risk for skin and soft tissue infections with *A. baumannii* arising from severe trauma or burn injuries sustained on the battlefield.

The genetically modified microorganism or compositions herein may be administered to warm-blooded mammals of any age. The genetically modified microorganism or compositions can be administered as a single dose or multiple priming doses, followed by one or more boosters. For example, a subject can receive a single dose, then be administered a booster dose up to 1 month, 2 months, 3 months, 4 months, 5 months, 6 months, 9 months, 1 year, 2 years, 3 years, 4 years, 5 years, 6 years, 7 years, 8 years, 9 years, or 10 or more years later.

Pharmaceutical Compositions

In another embodiment, the invention provides a pharmaceutical composition comprising the genetically modified microorganism as provided herein and a pharmaceutically acceptable carrier.

A pharmaceutical composition comprising a genetically modified microorganism may optionally comprise one or more possible additives, such as carriers, preservatives, stabilizers, adjuvants, and other substances.

In some embodiments, care should be taken when using additives so that the live genetically modified microorganism is not killed, or have its ability to effectively colonize the host compromised by the use of additives. Stabilizers, such as sucrose, maltose, trehalose, lactose, inositol or monosodium glutamate (MSG), may be added to stabilize the formulation against a variety of conditions, such as temperature variations or a freeze-drying process.

The dosages of a pharmaceutical composition of the invention can and will vary depending on the genetically modified microorganism, the antigen, and the intended host, as will be appreciated by one of skill in the art. Generally speaking, the dosage need only be sufficient to elicit a protective immune response in a majority of hosts. Routine experimentation may readily establish the required dosage. Typical initial dosages of vaccine for oral administration could be about $1\times10^7$ to $1\times10^{10}$ CFU depending upon the age of the host to be immunized. Administering multiple dosages may also be used as needed to provide the desired level of protective immunity.

The carrier or carriers must be pharmaceutically acceptable in the sense that they are compatible with the therapeutic ingredients and are not unduly deleterious to the recipient thereof. The therapeutic ingredient or ingredients are provided in an amount and frequency necessary to achieve the desired immunological effect.

The mode of administration and dosage forms will affect the therapeutic amounts of the genetically modified microorganism which is desirable and efficacious for the vaccination application. The current application is not limited specifically to oral administration of the vaccine, but can also include parenteral or other mucosal routes including sublingual administration as desired. The genetically modified microorganism is delivered in an amount capable of eliciting an immune reaction in which it is effective to increase the patient's immune response to the expressed antigen.

The genetically modified microorganism of the present invention may be usefully administered to the host animal with any other suitable pharmacologically or physiologically active agents, e.g., antigenic and/or other biologically active substances.

The genetically modified microorganism described herein can be prepared and/or formulated without undue experimentation for administration to a mammal, including humans, as appropriate for the particular application. The pharmaceutical compositions may be manufactured without undue experimentation in a manner that is itself known, e.g., by means of conventional mixing, dissolving, dragee-making, levitating, emulsifying, encapsulating, entrapping, spray-drying, or lyophilizing processes, or any combination thereof.

In one embodiment, the genetically modified microorganism is administered mucosally. Suitable routes of administration may include, for example, oral, lingual, sublingual, rectal, transmucosal, nasal, buccal, intrabuccal, intravaginal, or intestinal administration; intravesicular; intraurethral; administration by inhalation; intranasal, or intraocular injections, and optionally in a depot or sustained release formulation. Furthermore, one may administer the compound in a targeted drug delivery system. Combinations of administrative routes are possible.

The dose rate and suitable dosage forms for the genetically modified microorganism of the present invention may be readily determined by those of ordinary skill in the art without undue experimentation, by use of conventional antibody titer determination techniques and conventional bioefficacy/biocompatibility protocols. Among other things, the dose rate and suitable dosage forms depend on the particular antigen employed, the desired therapeutic effect, and the desired time span of bioactivity.

In some embodiments, the genetically modified microorganism can also be prepared for nasal administration. As used herein, nasal administration includes administering the compound to the mucous membranes of the nasal passage or nasal cavity of the subject. Pharmaceutical compositions for nasal administration of the genetically modified microorganism include therapeutically effective amounts of the genetically modified microorganism prepared by well-known methods to be administered, for example, as a nasal spray, nasal drop, suspension, gel, ointment, cream or powder. Administration of the genetically modified microorganism may also take place using a nasal tampon or nasal sponge.

The compositions may also suitably include one or more preservatives, anti-oxidants, or the like. Some examples of techniques for the formulation and administration of the genetically modified microorganism may be found in *Remington: The Science and Practice of Pharmacy*, Lippincott Williams & Wilkins Publishing Co., 21$^{st}$ addition, incorporated herein by reference.

In one embodiment, the pharmaceutical compositions contain the genetically modified microorganism in an effective amount to achieve their intended purpose. In one embodiment, an effective amount means an amount sufficient to prevent or treat an infection. In one embodiment, to treat means to reduce the development of, inhibit the progression of, or ameliorate the symptoms of a disease in the subject being treated. In one embodiment, to prevent means to administer prophylactically, e.g., in the case wherein in the opinion of the attending physician the subject's background, heredity, environment, occupational history, or the like, give rise to an expectation or increased probability that that subject is at risk of having the disease, even though at the time of diagnosis or administration that subject either does not yet have the disease or is asymptomatic of the disease.

A pharmaceutical composition of the invention may be administered via any suitable route, such as by oral administration or gastric intubation. Additionally, other methods of administering the genetically modified microorganism, such as intravenous, intramuscular, subcutaneous injection, intranasal administration or other parenteral routes, are possible.

In some embodiments, these compositions are formulated for oral administration. Accordingly, these compositions are preferably combined with pharmaceutically acceptable vehicles such as saline, Ringer's solution, dextrose solution, and the like.

Embodiments also encompass kits comprising any one of the compositions above in a suitable aliquot for vaccinating a host in need thereof. In one embodiment, the kit further comprises instructions for use. In other embodiments, the composition is lyophilized such that addition of a hydrating agent (e.g., buffered saline) reconstitutes the composition to generate a vaccine composition ready to administer, preferably orally or intranasally.

Application of the teachings of the present invention to a specific problem is within the capabilities of one having ordinary skill in the art in light of the teaching contained herein. Examples of the compositions and methods of the invention appear in the following non-limiting Examples.

EXAMPLES

Example 1. Live Attenuated S. Typhimurium Vaccines

We have created live attenuated vaccines with mutations in the guaBA, clpPX, htrA, and/or pipA genes (Tennant S M, Schmidlein P, Simon R, Pasetti M F, Galen J E, Levine M M. Refined live attenuated *Salmonella enterica* serovar Typhimurium and Enteritidis vaccines mediate homologous and heterologous serogroup protection in mice. Infect Immun. 2015; 83(12): 4504-12; Tennant S M, Wang J Y, Galen J E, Simon R, Pasetti M F, Gat O, et al. Engineering and preclinical evaluation of attenuated nontyphoidal *Salmonella* strains serving as live oral vaccines and as reagent strains. Infect Immun. 2011; 79(10): 4175-85). Each of these vaccines have at least two independently attenuating mutations in strains that are completely susceptible to antibiotics to facilitate regulatory approval. The genetic identity of all live vaccine strains constructed thus far has been confirmed by DNA sequencing of all chromosomal mutations; confirmation of the serovar Typhimurium has been carried out with LPS-specific antisera in agglutination tests, as well as by PCR and whole genome sequencing. Protection studies have shown that a candidate live attenuated S. Typhimurium vaccine can protect mice against lethal challenge with either the homologous parent or another serogroup B (e.g., S. Stanleyville) challenge strain (Tennant S M, Schmidlein P, Simon R, Pasetti M F, Galen J E, Levine M M. Refined live attenuated *Salmonella enterica* serovar Typhimurium and Enteritidis vaccines mediate homologous and heterologous serogroup protection in mice. Infect Immun. 2015; 83(12): 4504-12).

1. CVD 1921. The live attenuated vaccine strain CVD 1921 (S. Typhimurium 177 ΔguaBA ΔclpP) was demonstrated to be attenuated and immunogenic in BALB/c mice.[15] Oral immunization with $10^9$ colony forming units (CFU) of CVD 1921 protected mice against oral lethal challenge ($100 \times LD_{50}$) with wild-type (WT) S. Typhimurium 177 and elicited robust anti-LPS and anti-FliC serum IgG titers (Tennant S M, Wang J Y, Galen J E, Simon R, Pasetti M F, Gat O, et al. Engineering and preclinical evaluation of attenuated nontyphoidal *Salmonella* strains serving as live oral vaccines and as reagent strains. Infect Immun. 2011; 79(10): 4175-85). In collaboration with the Vaccine Research Center at NIH, we examined the tolerability of S. Typhimurium CVD 1921 (177 ΔguaBA ΔclpP) in an established chronic simian immunodeficiency virus (SIV)-infected rhesus macaque model.[26] Compared to the WT S. Typhimurium strain 177, in both SIV-infected and SIV-uninfected hosts, this live-attenuated vaccine showed reduced shedding and systemic spread, exhibited limited pathological disease manifestations in the digestive tract and induced low levels of cellular infiltration in tissues (data not shown); CVD 1921 therefore proved to be well tolerated in these highly immunocompromised animals. The vaccine was shed in stool for up to 10 days in non-SIV infected animals. Although less than the 21 days that was observed for a previous S. Typhimurium live vaccine evaluated in a Phase 1 clinical study, this level of shedding still exceeds our goal of <3 days shedding seen with licensed Ty21a in humans. (Hindle Z, Chatfield S N, Phillimore J, Bentley M, Johnson J, Cosgrove C A, et al. Characterization of *Salmonella enterica* derivatives harboring defined aroC and *Salmonella* pathogenicity island 2 type III secretion system (ssaV) mutations by immunization of healthy volunteers. Infect Immun. 2002; 70(7): 3457-67) We therefore added a pipA deletion to CVD 1921 to decrease fecal shedding and demonstrated that deletion of pipA from S. Typhimurium resulted in reduced fluid secretion in rabbit ileal loops compared to the WT strain as has been previously reported for *S. Dublin* in bovine intestinal loops (p=0.0082). (Wood M W, Jones M A, Watson P R, Hedges S, Wallis T S, Galyov E E. Identification of a pathogenicity island required for *Salmonella* enteropathogenicity. Mol Microbiol. 1998; 29(3): 883-91)

2. CVD 1926. We observed low level vaccinemia following immunization of mice with CVD 1921 and CVD 1921ΔpipA. Therefore, to further improve tolerability of the vaccine, we added a ΔhtrA mutation, creating CVD 1926 (177 ΔguaBA ΔclpP ΔpipA ΔhtrA). Mice were immunized perorally with 3 doses of $10^9$ CFU of CVD 1921ΔpipA or CVD 1926 4 weeks apart. CVD 1921 ΔpipA was well tolerated and no deaths were observed following vaccination. Anti-LPS serum IgG titers were significantly higher in mice immunized with CVD 1926 compared to mice that received CVD 1921 ΔpipA after 1 or 2 doses. Both CVD1921ΔpipA and CVD 1926-immunized animals were protected against low dose ($100 \times LD_{50}$) challenge with WT S. Typhimurium 177 (not shown) and CVD 1926 animals were also significantly protected against a high challenge dose ($700 \times LD_{50}$), with a vaccine efficacy of 47% (p=0.006) (FIG. 1).

Figure 2:
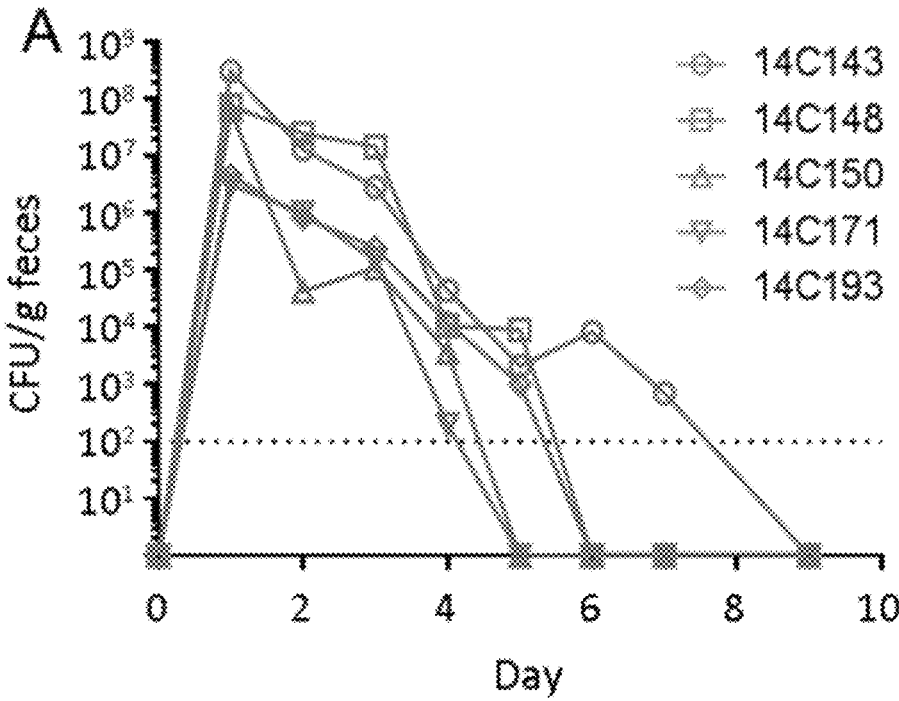
FIG. 2. Evaluation of CVD 1926 vaccine in rhesus macaques. A) Shedding of the vaccine strain CVD 1926 in stool. Dotted line=limit of detection. B) Anti-LPS serum IgG titers. Arrow=immunization.
Figure 2:
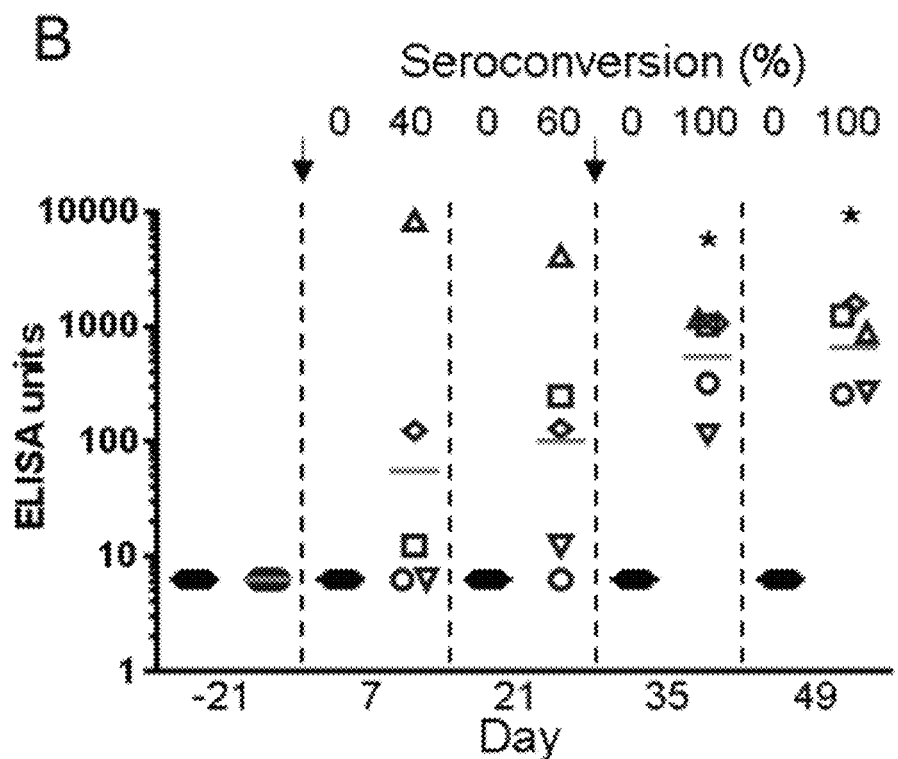

We subsequently evaluated CVD 1926 for its ability to protect rhesus macaques against gastroenteritis using a model that was first used in the 1970's and that we recently established at the CVD (Rout W R, Formal S B, Dammin G J, Giannella R A. Pathophysiology of *Salmonella* diarrhea in the Rhesus monkey: Intestinal transport, morphological and bacteriological studies. Gastroenterology. 1974; 67(1): 59-70; Kent T H, Formal S B, Labrec E H. *Salmonella* gastroenteritis in rhesus monkeys. Arch Pathol. 1966; 82(3): 272-9; Higginson E E, Simon R, Tennant S M. Animal models for Salmonellosis—applications in vaccine research. Clin Vaccine Immunol. 2016; Ramachandran G, Panda A, Higginson E E, Ateh E, Lipsky M M, Sen S, et al. Virulence of invasive *Salmonella* Typhimurium ST313 in animal models of infection. PLoS Negl Trop Dis. 2017; 11(8): e0005697). This model replicates well what is observed in human clinical infection (similar incubation time and symptoms). Indian rhesus macaques (n=5) were immunized intragastrically (i.g) with either saline or CVD 1926 (S. Typhimurium 177 ΔguaBA ΔclpP ΔpipA ΔhtrA). Two doses of vaccine ($6 \times 10^9$ CFU) were given, 4 weeks apart. Immunization was well tolerated, with no animals showing signs of illness or dehydration. Vaccine was shed in feces for 4 to 7 days post immunization (FIG. 2A). In contrast, S. Typhimurium 177 was shed for up to 18 days in a previous experiment[31] and shed for 13 days from naive animals in our vaccination experiment (data not shown). After the second dose, all 5 CVD 1926-immunized monkeys had seroconverted for anti-O-polysaccharide serum IgG (FIG. 2B) and sera was able to significantly increase uptake of S. Typhimurium by J774 macrophages over unvaccinated animals. Immunized monkeys were challenged i.g. with S. Typhimurium 177 on day 57 of the study. Using area under the curve analysis, animals vaccinated with CVD 1926 shed less bacteria than unvaccinated animals (p=0.029, one-tailed; not shown). Collectively, unvaccinated animals had a significantly greater number of days with diarrhea when compared to unvaccinated animals (p=0.05). Overall vaccine efficacy for CVD 1926 was calculated using moderate to severe diarrhea (MSD) as an endpoint. All 5 animals given saline had MSD whereas only one of the vaccinated animals exhibited MSD. The efficacy of the vaccine in the rhesus macaque gastroenteritis model was determined to be 80% (p=0.024, Fisher's exact test).

Although our lead serogroup B vaccine candidate CVD 1926 is well tolerated, immunogenic, and confers protection in both mice and rhesus macaques against WT S. Typhimurium, our goal is to increase the clinical acceptability of our vaccine by reducing the duration of fecal shedding from 7 days (as was observed in the rhesus macaque experiment), to <3 days as has been shown for the licensed S. Typhi Ty21a vaccine.

Experimental Design:

Aim 1. To genetically engineer our leading candidate live attenuated S. Typhimurium vaccine, CVD 1926, such that ssb encoding the essential single stranded DNA-binding protein, SSB, will be transcriptionally regulated by a tightly controlled arabinose-inducible promoter.

We will use an arabinose-regulated transcriptional control system to regulate expression of SSB and verify that the resulting strains are no longer capable of replicating in the absence of arabinose.

All chromosomal manipulations will be carried out using the lambda Red chromosomal mutagenesis system (Feasey N A, Cain A K, Msefula C L, Pickard D, Alaerts M, Aslett M, et al. Drug resistance in *Salmonella enterica* ser. Typhimurium bloodstream infection, Malawi. Emerg Infect Dis. 2014; 20(11): 1957-9), which we have used successfully in the engineering of attenuated *Salmonella* vaccines for over a decade (Tennant S M, Schmidlein P, Simon R, Pasetti M F, Galen J E, Levine M M. Refined live attenuated *Salmonella enterica* serovar Typhimurium and Enteritidis vaccines mediate homologous and heterologous serogroup protection in mice. Infect Immun. 2015; 83(12): 4504-12; Tennant S M, Wang J Y, Galen J E, Simon R, Pasetti M F, Gat O, et al. Engineering and preclinical evaluation of attenuated nontyphoidal *Salmonella* strains serving as live oral vaccines and as reagent strains. Infect Immun. 2011; 79(10): 4175-85; Gat O, Galen J E, Tennant S, Simon R, Blackwelder W C, Silverman D J, et al. Cell-associated flagella enhance the protection conferred by mucosally-administered attenuated *Salmonella* ParaTyphi A vaccines. PLoS Negl Trop Dis. 2011; 5(11): e1373; Wang J Y, Harley R H, Galen J E. Novel methods for expression of foreign antigens in live vector vaccines. Hum Vaccin Immunother. 2013; 9(7): 1558-64.Galen J E, Wang J Y, Carrasco J A, Lloyd S A, Mellado-Sanchez G, Diaz-McNair J, et al. A bivalent typhoid live vector vaccine expressing both chromosome- and plasmid-encoded *Yersinia pestis* antigens fully protects against murine lethal pulmonary plague infection. Infect Immun. 2015; 83(1): 161-72; Galen J E, Wang J Y, Chinchilla M, Vindurampulle C, Vogel J E, Levy H, et al. A new generation of stable, nonantibiotic, low-copy-number plasmids improves immune responses to foreign antigens in *Salmonella enterica* serovar Typhi live vectors. Infect Immun. 2010; 78(1): 337-47).

Figure 3:
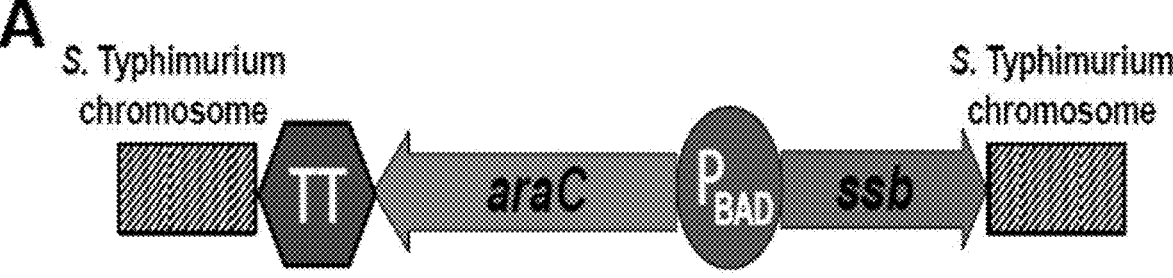
FIG. 3. Strategy for engineering arabinose-regulated transcription of GFPuv. A) A synthetic cassette was constructed which preserves the natural arabinose-regulated synthesis of the DNA-binding regulatory protein AraC, which positively regulates transcription from the P$_{BAD}$ promoter in the presence of arabinose. A transcriptional terminator (TT) is included at the 3' terminus of araC to prevent strong transcription of araC from interfering with proper regulation of the downstream chromosomal genes. This araC-P$_{BAD}$ cassette will be integrated into the S. Typhimurium chromosome at the ssb locus by homologous recombination. B) Induction of a synthetic araC-P$_{BAD}$-gfpuv test cassette encoded by a high copy number pUC57 plasmid in *E. coli* plated onto solid medium containing various concentrations of arabinose.
Figure 3:
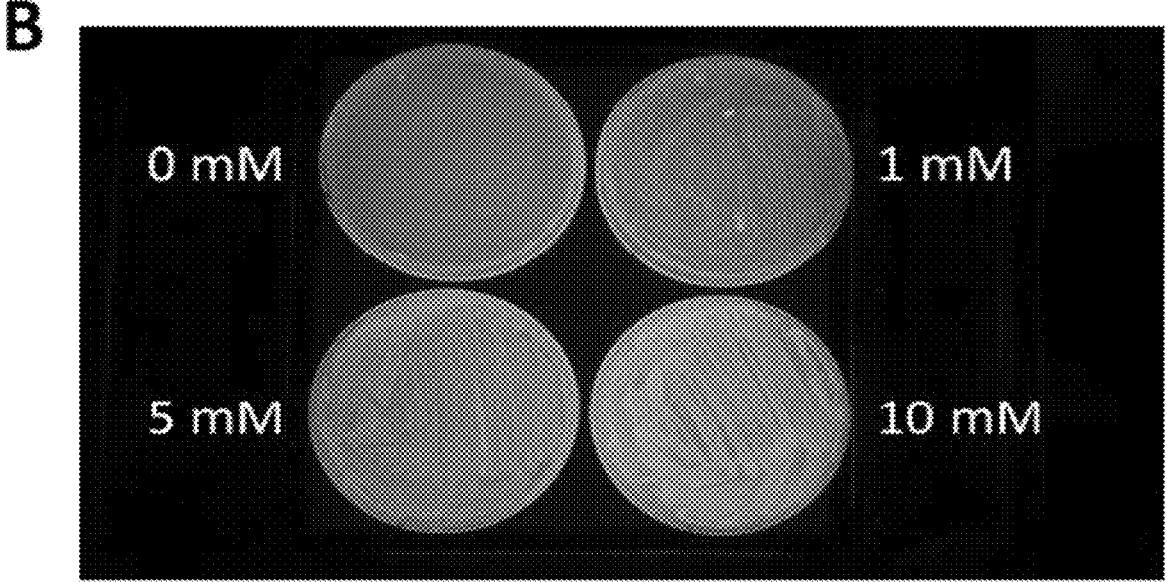

A synthetic TT-araC-$P_{BAD}$ transcription cassette will be constructed and chromosomally integrated into CVD 1926 upstream of ssb, replacing only the ssb promoter ($P_{ssb}$) as shown in FIG. 3A, creating the attenuated strain CVD 1926 $P_{BAD}$-ssb. To determine the effect that this recombination has on the parental S. Typhimurium WT strain alone, we will also integrate the TT-araC-PBAD transcription cassette into S. Typhimurium I77 to create 177 PBAD-ssb. As suggested by Guzman et al. (Guzman L M, Belin D, Carson M J, Beckwith J. Tight regulation, modulation, and high-level expression by vectors containing the arabinose PBAD promoter. J Bacteriol. 1995; 177(14): 4121-30) and successfully tested by Curtiss et al., we will also delete the arabinose catalytic enzymes ribulokinase (araB), isomerase (araC), and epimerase (araD). (Curtiss R, 3rd, Wanda S Y, Gunn B M, Zhang X, Tinge S A, Ananthnarayan V, et al. *Salmonella enterica* serovar Typhimurium strains with regulated delayed attenuation in vivo. Infect Immun. 2009; 77(3): 1071-82; Curtiss R, 3rd, Xin W, Li Y, Kong W, Wanda S Y, Gunn B, et al. New technologies in using recombinant attenuated *Salmonella* vaccine vectors. Crit Rev Immunol. 2010; 30(3): 255-70; Schleif R. AraC protein, regulation of the 1-arabinose operon in *Escherichia coli*, and the light switch mechanism of AraC action. FEMS Microbiol Rev. 2010; 34(5): 779-96). Deletion of araBAD is expected to prevent intracellular catabolism of imported arabinose, prolonging retention of intracellular arabinose and preventing cessation of replication too abruptly. The chromosomal araBAD locus will be deleted from CVD 1926 $P_{BAD}$-ssb creating CVD 1926 $P_{BAD}$-ssb ΔaraBAD. For comparison, we will also delete the araBAD locus from 177 $P_{BAD}$-ssb creating 177 $P_{BAD}$-ssb ΔaraBAD. The strains to be constructed are shown in Table 1. Upon completion of these candidate LANT strains, we will conduct growth kinetic studies (measuring $OD_{600}$ and performing viable counts; ≥3 independent experiments) in Hy Soy broth medium (similar to Luria Bertani but with animal product-free components, as encouraged by the FDA for vaccines intended for oral vaccination of humans) and minimal medium with or without 0.2% arabinose to confirm arrest of viability in the absence of arabinose. We will also examine replication (in duplicate wells) in cultured cells including human U937 and/or THP-1 and murine J774 macrophages to confirm arrest of replication intracellularly in the absence of arabinose, on at least 3 separate occasions.

LANT strains that stop replicating in the absence of arabinose.

Aim 2. To determine the in vivo persistence, immunogenicity, and protective efficacy of S. Typhimurium candidate LANT vaccines in mice.

We hypothesize that mice orally administered attenuated S. Typhimurium LANT vaccines will shed bacteria in their stool for significantly fewer days than their isogenic counterparts expressing SSB. We also hypothesize that optimized LANT strains will maintain immunogenicity versus unmodified parent vaccines and will be able to protect mice against lethal challenge with wild-type S. Typhimurium.

Approach. Aim 2A. To determine the level of attenuation and fecal shedding of arabinose-controlled CVD 1926 LANT vaccines in BALB/c mice.

Figure 5:
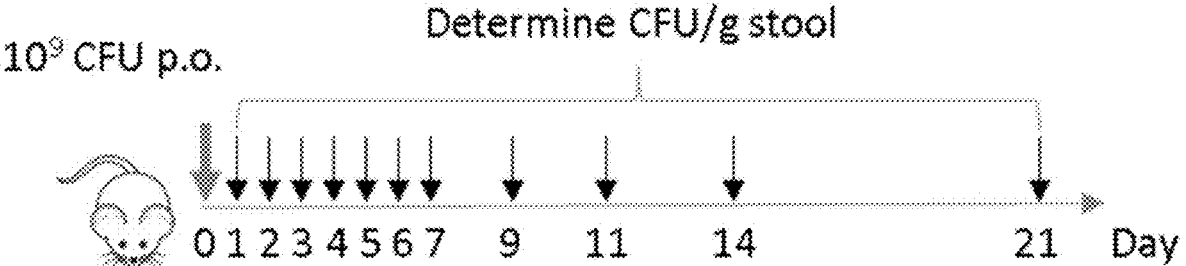
FIG. 5. Determination of fecal shedding of the live attenuated non-transmissible (LANT) strains.

First, we will determine the contribution that the $P_{BAD}$-ssb insertion has on attenuation of the WT I77 strain. We will perform a 50% lethal dose experiment in which we will infect 6- to 8-week-old BALB/c mice (n=5; male and female) perorally with 10-fold dilutions of bacteria (e.g., $10^4$-$10^9$ CFU; i.e., 6 doses will be tested). We will infect mice with the following groups: 1) I77, 2) I77 $P_{BAD}$-ssb, 3) 177 ΔaraBAD, and 4) 177 $P_{BAD}$-ssb ΔaraBAD. We will monitor mice for 28 days for morbidity and mortality and will determine the $LD_{50}$ by linear regression. This experiment will establish the level of attenuation resulting from integration of the $P_{BAD}$-ssb cassette alone with/or without the araBAD deletion in wild-type 177. We will not determine the $LD_{50}$ of CVD 1926 $P_{BAD}$-ssb and CVD 1926 $P_{BAD}$-ssb ΔaraBAD as the $LD_{50}$ of the parental strain (CVD 1926) is already >$10^9$ CFU. Second, we will examine in vivo replication kinetics of our recombinant strains. We will inoculate 6- to 8-week-old BALB/c mice perorally (n=10; 5 male and 5 female) with $10^9$ CFU of CVD 1926 $P_{BAD}$-ssb and CVD 1926 $P_{BAD}$-ssb ΔaraBAD and compare in vivo growth kinetics with unmodified CVD 1926. We will assess fecal shedding of the bacteria by performing viable counts daily on days 1 to 7 post-infection (p.i) and then on days, 9, 11, 14 and 21 (FIG. 5). We will determine the CFU/g stool by suspending stool in PBS and spread plating on *Salmonella-Shigella* (SS) agar.

Aim 2B. To show that arabinose-controlled CVD 1926 LANT vaccines are immunogenic and can protect mice against lethal challenge with wild-type S. Typhimurium.

We will immunize 6-to-8-week-old male and female BALB/c mice perorally (by gavage), three times with $10^9$ CFU of CVD 1926 $P_{BAD}$-ssb ΔaraBAD, CVD 1926 $P_{BAD}$-

TABLE 1

| Strains used in this study | | |
| --- | --- | --- |
| Name of strain | Characteristics | Reference |
| I77 | None (WT) | [41,42] |
| I77 $P_{BAD}$-ssb | $P_{BAD}$-ssb | This study |
| I77 $P_{BAD}$-ssb ΔaraBAD | $P_{BAD}$-ssb ΔaraBAD | This study |
| CVD 1926 | ΔguaBA ΔclpP ΔpipA ΔhtrA | Unpublished data |
| CVD 1926 $P_{BAD}$-ssb | ΔguaBA ΔclpP ΔpipA ΔhtrA $P_{BAD}$-ssb | This study |
| CND 1926 $P_{BAD}$-ssb ΔaraBAD | ΔguaBA ΔclpP ΔpipA ΔhtrA $P_{BAD}$-ssb ΔaraBAD | This study |

Figure 6:
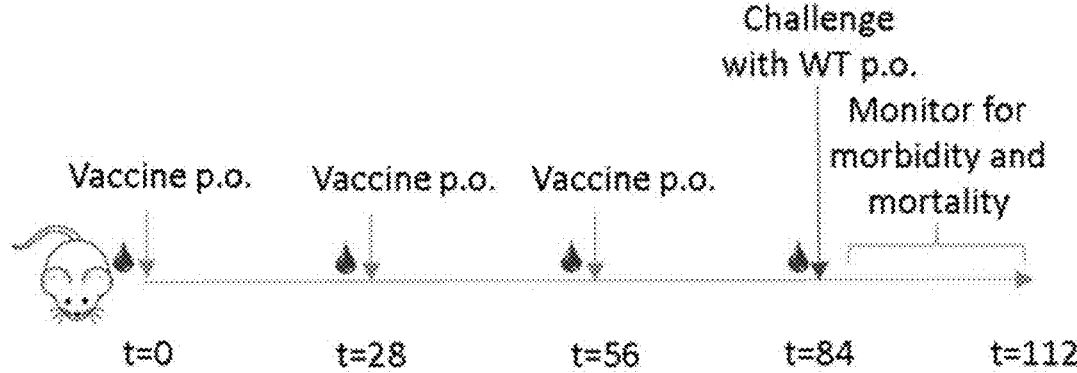
FIG. 6. Timeline for immunization experiment.
Figure 7:
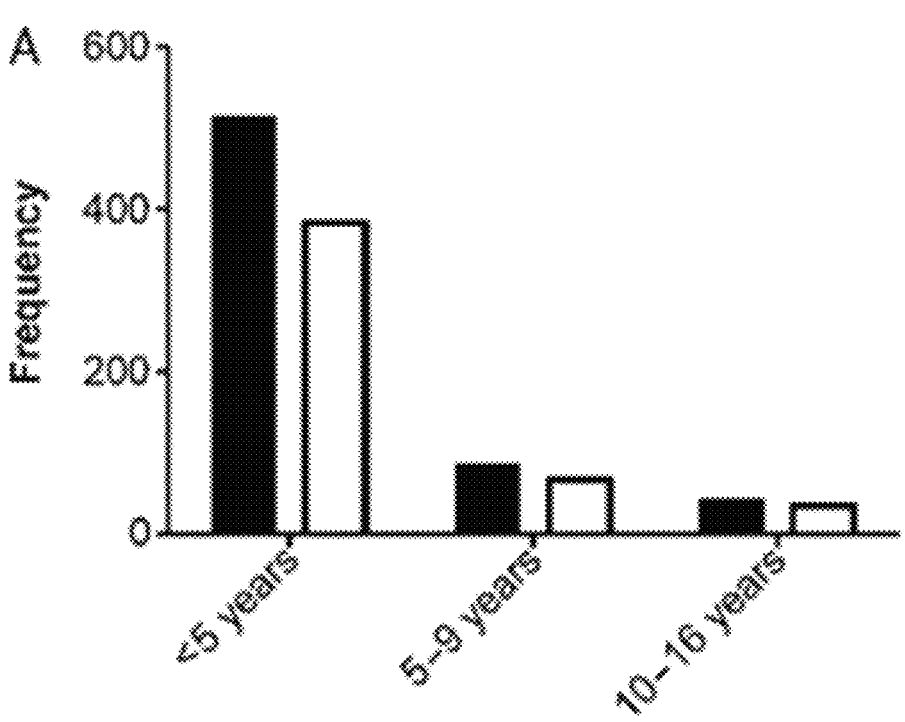
FIG. 7. Age distribution of pediatric patients in Mali with iNTS. A) 5-16 years, B) 0-59 months. Black=all NTS. White=Typhimurium and Enteritidis.[3]
Figure 7:
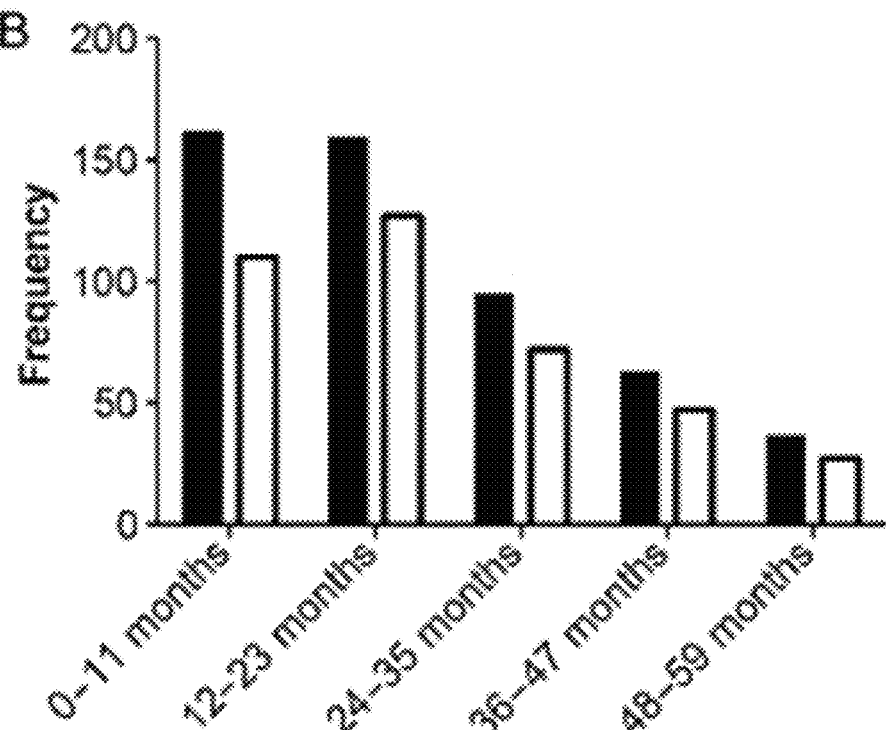

We hypothesize that the arabinose-controlled CVD 1926 $P_{BAD}$-ssb and 177 $P_{BAD}$-ssb strains will stop replicating in the absence of arabinose in bacteriological medium as well as in cultured mammalian cells. Deletion of the araBAD operon from these strains should result in a slight delay in replication arrest. We anticipate development of candidate ssb, CVD 1926, or PBS, with one month between each immunization (Table 2 and FIG. 6). We will obtain blood and feces prior to each immunization and one month after the last immunization to measure anti-LPS and anti-FliC serum IgG and fecal IgA responses. We will subsequently challenge mice perorally with a lethal challenge dose (100×

$LD_{50}$) of wild-type S. Typhimurium 177, one month after the last vaccination and determine vaccine efficacy.

TABLE 2

Immunization groups to be tested for vaccine efficacy.

| Gp | Immunogen | Challenge | N | Males/ females |
|----|-----------|-----------|---|---------|
| 1 | CVD 1926 $P_{BAD}$-ssb | S. Typhimurium WT | 15 | 7/8 |
| 2 | CVD 1926 $P_{BAD}$-ssb araBAD | S. Typhimurium WT | 15 | 8/7 |
| 3 | CVD 1926 | S. Typhimurium WT | 15 | 7/8 |
| 4 | PBS | S. Typhimurium WT | 15 | 8/7 |

We will determine 50% lethal dose by linear regression. We have found that n=5 and 6 doses (10-fold dilutions) produce robust $LD_{50}$ data. We expect that 177 $P_{BAD}$-ssb and 177 $P_{BAD}$-ssb $\Delta$araBAD will be attenuated ($LD_{50}$>$10^9$ CFU). We expect conditional expression of SSB through arabinose regulation to tightly control the number of generations of a candidate LANT strain after immunization. We expect that mice will shed CVD 1926 for >7 days (based on the rhesus macaque data) and that mice will shed CVD 1926 $P_{BAD}$-ssb or CVD 1926 $P_{BAD}$-ssb $\Delta$araBAD for ≤3 days. If we assume that the duration of shedding is normally distributed with a standard deviation of 3 days and n=10 animals, if the true difference in the CVD 1926 and CVD 1926 PBAD-ssb or CVD 1926 $P_{BAD}$-ssb $\Delta$araBAD means is 4 days, we will be able to reject the null hypothesis that the means of the experimental and control groups are equal with probability (power) 0.805 (2-sided test, $\alpha$=0.05). We also expect to show that appropriately attenuated arabinose-controlled CVD 1926 vaccine is able to protect mice against lethal challenge with wild-type S. Typhimurium 177. For 15 mice receiving CVD 1926 $P_{BAD}$-ssb $\Delta$araBAD and 15 receiving PBS, and true attack rates of 20% (or lower) with vaccine and 75% with PBS, the power to show a significant difference in attack rates with a Fisher's exact test at a two-sided 0.05 significance level is 80%. Although we will measure anti-LPS and anti-FliC serum IgG and fecal IgA responses, we will not use titers/seroconversion to determine success of our approach. We anticipate demonstrating that an appropriately attenuated LANT vaccine is shed for significantly less time than the parental vaccine strain while still conferring protection against lethal challenge with wild-type S. Typhimurium.

The guaBA and clpP mutations that we have used each raise the $LD_{50}$ by >5 $log_{10}$ (the $LD_{50}$ of WT I77 is ~2×$10^4$ CFU). (Tennant S M, Wang J Y, Galen J E, Simon R, Pasetti M F, Gat O, et al. Engineering and preclinical evaluation of attenuated nontyphoidal *Salmonella* strains serving as live oral vaccines and as reagent strains. Infect Immun. 2011; 79(10): 4175-85). Miller et al. showed that deletion of htrA from S. Typhimurium raises the intravenous (i.v) $LD_{50}$ by ~5 $log_{10}$. (Miller I, Maskell D, Hormaeche C, Johnson K, Pickard D, Dougan G. Isolation of orally attenuated *Salmonella* Typhimurium following TnphoA mutagenesis. Infect Immun. 1989; 57(9): 2758-63; Johnson K, Charles I, Dougan G, Pickard D, O'Gaora P, Costa G, et al. The role of a stress-response protein in *Salmonella* Typhimurium virulence. Mol Microbiol. 1991; 5(2): 401-7). Likewise, we found that CVD 1921 and CVD 1926 had $LD_{50}$s>$10^9$ CFU. Despite having multiple attenuating mutations, our candidate vaccine CVD 1926 grows well, is immunogenic, and can protect mice and rhesus macaques against wild-type challenge. However, it is possible that introduction of $P_{BAD}$- ssb into our optimized CVD 1926 vaccine will result in an over-attenuated strain (which is non-transmissible but poorly immunogenic). Since previous work has clearly shown that over-attenuated S. Typhimurium strains are not immunogenic in BALB/c mice, we would need to re-engineer our LANT strains to achieve a balance between attenuation and immunogenicity. (O'Callaghan D, Maskell D, Liew F Y, Easmon C S, Dougan G. Characterization of aromatic- and purine-dependent *Salmonella* Typhimurium: attention, persistence, and ability to induce protective immunity in BALB/c mice. Infect Immun. 1988; 56(2): 419-23) If we observe that the $P_{BAD}$-ssb integration results in over-attenuation of CVD1926, we will integrate these arabinose cassettes into 177 $\Delta$guaBA instead of CVD 1926 to again maintain at least two independently attenuating mutations in a clinically acceptable live attenuated vaccine, as recommended by the FDA. We would then test the following groups for immunogenicity and protection against challenge: 1) 177 $\Delta$guaBA $P_{BAD}$-ssb, 2) 177 $\Delta$guaBA $P_{BAD}$-ssb $\Delta$araBAD, 3) 177 $\Delta$guaBA and 4) PBS. Our proposed alternative strategy emphasizes here that the efficient engineering of immunogenic LANT strains can utilize any combination of independently attenuating mutations to optimize both metabolic fitness and immunogenicity while minimizing clinically unacceptable reactogenicity and transmissibility. (Galen J E, Curtiss R, 3rd. The delicate balance in genetically engineering live vaccines. Vaccine. 2014; 32(35): 4376-85).

Example 2. Live Attenuated Non-Transmissible (LANT) *Salmonella* Vaccine NTS Surveillance and Source of Strains Our blood culture-based surveillance for blood-borne pathogens in febrile children in Bamako, Mali during the past 17 years has yielded ~~700 NTS strains, including S. Typhimurium, S. Enteritidis, S. I 4,[5], 12:i:- and S. Dublin. (Tapia M D, Tennant S M, Bornstein K, Onwuchekwa U, Tamboura B, Maiga A, et al. Invasive nontyphoidal *Salmonella* infections among children in Mali, 2002-2014: Microbiological and epidemiologic features guide vaccine development. Clin Infect Dis. 2015; 61 Suppl 4: S332-8; Tennant S M, Diallo S, Levy H, Livio S, Sow S O, Tapia M, et al. Identification by PCR of non-typhoidal *Salmonella enterica* serovars associated with invasive infections among febrile patients in Mali. PLoS NeglTrop Dis. 2010; 4(3): e621; Fuche F J, Sen S, Jones J A, Nkeze J, Permala-Booth J, Tapia M D, et al. Characterization of Invasive *Salmonella* Serogroup C1 Infections in Mali. Am J Trap Med Hyg. 2018; 98(2): 589-94). Our invasive S. Typhimurium and S. Enteritidis strains from Mali are genetically similar to other iNTS strains circulating in sub-Saharan Africa (Okoro C K, Kingsley R A, Connor T R, Harris S R, Parry C M, Al-Mashhadani M N, et al. Intracontinental spread of human invasive *Salmonella* Typhimurium pathovariants in sub-Saharan Africa. Nat Genet. 2012; 44(11); 1215-21; Feasey N A, Hadfield J, Keddy K H, Dallman T J, Jacobs J, Deng X, et al. Distinct *Salmonella* Enteritidis lineages associated with enterocolitis in high-income settings and invasive disease in low-income settings. Nat Genet. 2016; 48(10): 1211-7).

Live attenuated NTS vaccines. We have created a variety of live attenuated S. Typhimurium and S. Enteritidis vaccines with mutations in the guaBA, clpPX, htrA, and/or pipA genes (Tennant S M, Schmidlein P, Simon R, Pasetti M F, Galen J E, Levine M M. Refined live attenuated *Salmonella enterica* serovar Typhimurium and Enteritidis vaccines mediate homologous and heterologous serogroup protection in mice. Infect Immun. 2015; 83(12): 4504-12; Tennant S M, Wang J Y, Galen J E, Simon R, Pasetti M F, Gat 0, et al. Engineering and preclinical evaluation of attenuated nontyphoidal *Salmonella* strains serving as live oral vaccines and as reagent strains. Infect Immun. 2011; 79(10): 4175-85; Higginson E E, Ramachandran G, Panda A, Shipley S T, Kriel E H, DeTolla U, et al. Improved Tolerability of a *Salmonella enterica* Serovar Typhimurium Live-Attenuated Vaccine Strain Achieved by Balancing Inflammatory Potential with Immunogenicity. Infect Immun. 2018; 86(12)). Each of these vaccines have at least two independently attenuating mutations in strains that are completely susceptible to antibiotics to facilitate regulatory approval.

Prototypic live NTS vaccines. Prototype attenuated vaccine strains S. Typhimurium CVD 1921 and S. Enteritidis CVD 1941, derived from wild type strains 177 and R11 respectively, isolated from toddlers in Mali with bacteraemia, were constructed by deleting chromosomal guaBA (controlling guanine nucleotide biosynthesis) and clpPX (encoding a regulatory protease). (Tennant S M, Wang J Y, Galen J E, Simon R, Pasetti M F, Gat 0, et al. Engineering and preclinical evaluation of attenuated nontyphoidal *Salmonella* strains serving as live oral vaccines and as reagent strains. Infect Immun. 2011; 79(10): 4175-85) Both strains are highly attenuated in BALB/c mice, with an oral $LD_{20} > 10^9$ CFU (>5 logs above that of each wild type parent). Following oral immunization of BALB/c mice with $10^9$ CFU (3 times at 4 week intervals), CVD 1921 and CVD 1941 induced strong immune responses and significantly protected the animals against oral challenge one month later with $100 \times LD_{50}$ of 177 and R11, respectively.

Figure 9:
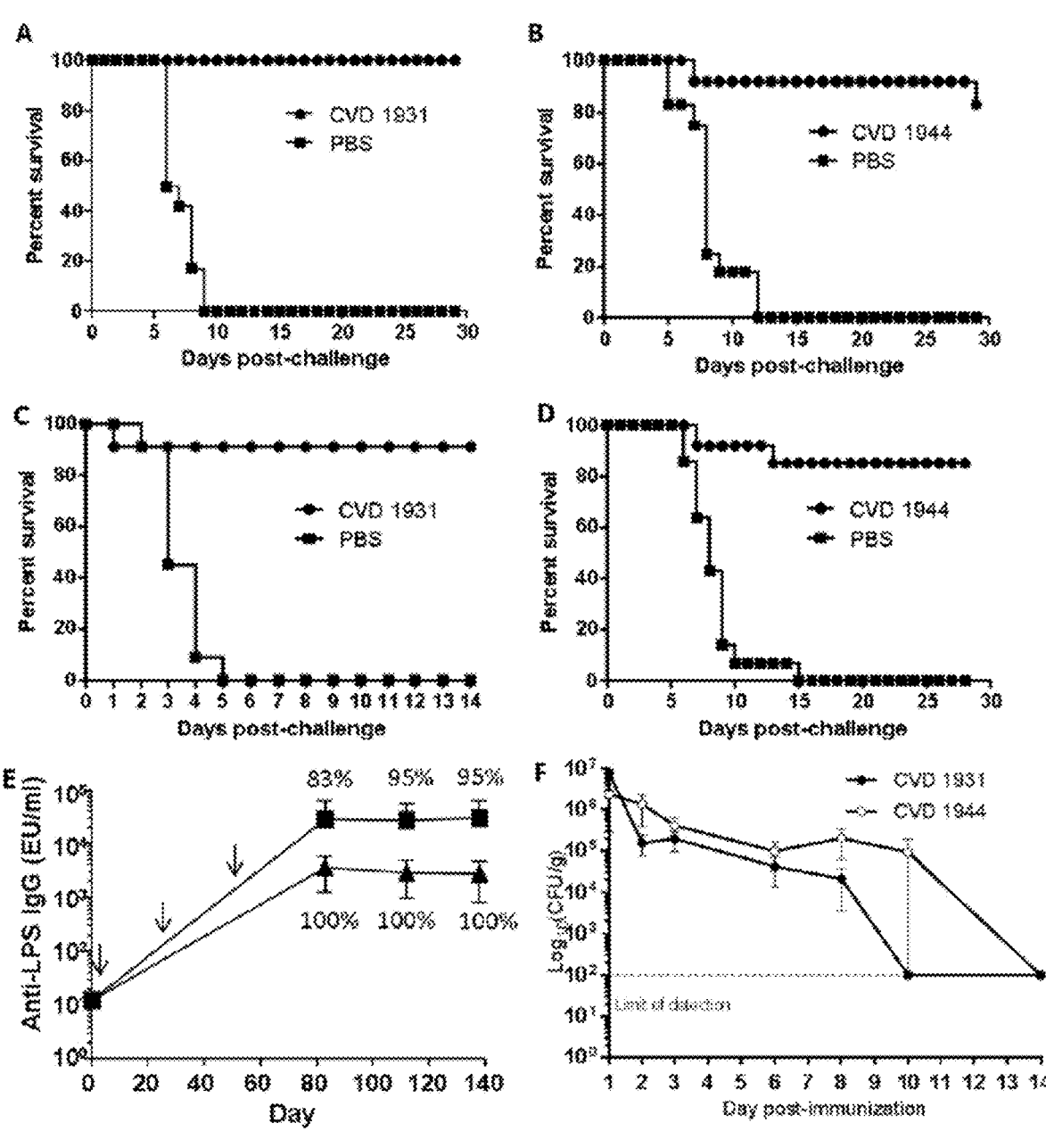
FIG. 9. A) S. Typhimurium CVD 1931-immunized mice were orally challenged with 10,000×LD$_{50}$ of S. Typhimurium D65. B) S. Enteritidis CVD 1944-immunized mice were orally challenged with 10,000×LD$_{50}$ of S. Enteritidis R11. C) S. Typhimurium CVD 1931-immunized mice were intraperitoneally challenged with 3 LD$_{50}$ of S. Stanleyville J65. D) CVD 1944-immunized mice were orally challenged with 800 LD$_{50}$ of S. Dublin R17. E) Anti-LPS IgG geometric mean titers (GMTs) and % seroconversion (4-fold rise) elicited by live oral vaccines CVD 1931 (squares) and CVD 1944 (triangles) up to 12 weeks after the last immunization. Arrow=immunizations. (Infect Immun. 2015; 83(12): 4504-12) F) Shedding of S. Typhimurium CVD 1931 and S. Enteritidis CVD 1944 in stool of mice (unpublished).
Figure 10:
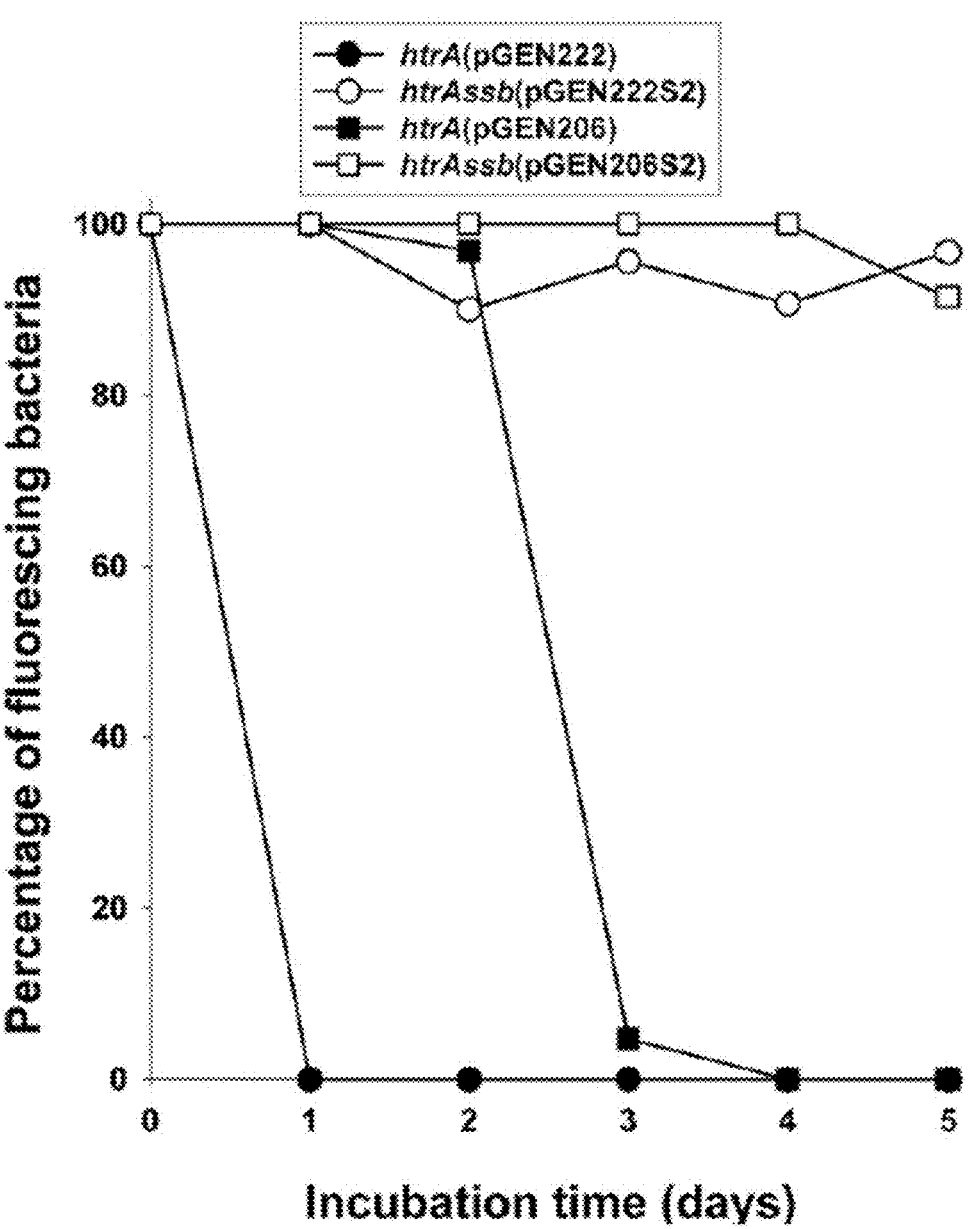
FIG. 10. Plasmids containing ssb (pGEN222S2 and pGEN206S2) are stably maintained by *S. Typhi* ssb-negative strains (htrA ssb) whereas plasmids that lack ssb are rapidly lost by *S. Typhi* (Galen J E, Wang J Y, Chinchilla M, Vindurampulle C, Vogel J E, Levy H, et al. A new generation of stable, nonantibiotic, low-copy-number plasmids improves immune responses to foreign antigens in *Salmonella enterica* serovar Typhi live vectors. Infect Immun. 2010; 78(1): 337-47).

Refined live iNTS vaccines. Encouraged by results with the prototype S. Typhimurium and S. Enteritidis live vaccines, we constructed definitive iNTS vaccine strains. The live attenuated S. Typhimurium vaccine strain CVD 1931 (S. Typhimurium D65 ΔguaBA ΔclpX) was demonstrated to be attenuated and immunogenic in BALB/c mice. (Tennant S M, Schmidlein P, Simon R, Pasetti M F, Galen J E, Levine M M. Refined live attenuated *Salmonella enterica* serovar Typhimurium and Enteritidis vaccines mediate homologous and heterologous serogroup protection in mice. Infect Immun. 2015; 83(12): 4504-12) The parental strain of this vaccine is S. Typhimurium D65, an ST313, isolated from the blood of a pediatric patient in Mali. (Tapia M D, Tennant S M, Bornstein K, Onwuchekwa U, Tamboura B, Maiga A, et al. Invasive nontyphoidal *Salmonella* infections among children in Mali, 2002-2014: Microbiological and epidemiologic features guide vaccine development. Clin Infect Dis. 2015; 61 Suppl 4: S332-8; Ramachandran G, Perkins D J, Schmidlein P J, Tulapurkar M E, Tennant S M. Invasive *Salmonella* Typhimurium ST313 with Naturally Attenuated Flagellin Elicits Reduced Inflammation and Replicates within Macrophages. PLoS Negl Trop Dis. 2015; 9(1): e3394). Oral immunization with $10^9$ CFU of CVD 1931 protected 6-to-8-week old BALB/c mice against a high oral lethal challenge dose ($10,000 \times LD_{50}$) of wild-type (WT) S. Typhimurium D65 and elicited robust anti-LPS and anti-FliC serum IgG titers (FIG. 9). (Tennant S M, Schmidlein P, Simon R, Pasetti M F, Galen J E, Levine M M. Refined live attenuated *Salmonella enterica* serovar Typhimurium and Enteritidis vaccines mediate homologous and heterologous serogroup protection in mice. Infect Immun. 2015; 83(12): 4504-12). Likewise, we constructed the S. Enteritidis vaccine CVD 1944 (S. Enteritidis R11 ΔguaBA ΔclpX) which was attenuated, immunogenic and able to protect mice against a $10,000 \times LD_{50}$ challenge dose of wild-type S. Enteritidis R11, a bloodstream isolate from Mali. Protection studies have shown that the live NTS vaccines could protect mice against lethal challenge with another serovar from the same serogroup as the vaccine strain (i.e., the S. Typhimurium vaccine could protect against challenge with S. Stanleyville [serogroup B] and the S. Enteritidis vaccine could protect against challenge with S. Dublin [serogroup D]) (Tennant S M, Schmidlein P, Simon R, Pasetti M F, Galen J E, Levine M M. Refined live attenuated *Salmonella enterica* serovar Typhimurium and Enteritidis vaccines mediate homologous and heterologous serogroup protection in mice. Infect Immun. 2015; 83(12): 4504-12). However, both vaccines were shed in stool of mice for 8-10 days (FIG. 9). We have attempted to reduce the potential for transmissibility by incorporating a mutation in the pip operon (involved in fluid secretion)[61] of one of our other S. Typhimurium vaccine candidates but the strain was still shed in stool for 4-7 days by rhesus macaques (manuscript in preparation). Hence, the need for a better method to reduce transmissibility remains a priority.

Functional antibody assays. We have developed assays to determine end-point serum bactericidal antibody (SBA) titers to assess the immunogenicity of S. Typhimurium and S. Enteritidis vaccine candidates (Boyd M A, Tennant S M, Saague V A, Simon R, Muhsen K, Ramachandran G, et al. Serum bactericidal assays to evaluate typhoidal and nontyphoidal *Salmonella* vaccines. Clin Vaccine Immunol. 2014; 21(5); 712-21). We have also developed assays to determine end-point opsonophagocytic antibody (OPA) titers elicited by S. Typhimurium and S. Enteritidis vaccines (Ramachandran G, Boyd M A, MacSwords J, Higginson E E, Simon R, Galen J E, et al. Opsonophagocytic Assay To Evaluate Immunogenicity of Nontyphoidal *Salmonella* Vaccines. Clin Vaccine Immunol. 2016; 23(6): 520-3). We have shown that our live attenuated NTS vaccines elicit high SBA and OPA titers (Ramachandran G, Boyd M A, MacSwords J, Higginson E E, Simon R, Galen J E, et al. Opsonophagocytic Assay To Evaluate Immunogenicity of Nontyphoidal *Salmonella* Vaccines. Clin Vaccine Immunol. 2016; 23(6): 520-3; Ault A, Tennant S M, Gorres J P, Eckhaus M, Sandier N G, Roque A, et al. Safety and tolerability of a live oral *Salmonella* Typhimurium vaccine candidate in SIV-infected nonhuman primates. Vaccine. 2013; 31(49): 5879-88; Ramachandran G, Tennant S M, Boyd M A, Wang J Y, Tulapurkar M E, Pasetti M F, et al. Functional Activity of Antibodies Directed towards Flagellin Proteins of Non-Typhoidal *Salmonella*. PLoS One. 2016; 11(3): e0151875). These assays will be used to measure functional activity of antibodies generated in this project.

Single-stranded DNA binding protein. Our team has experience creating live attenuated *Salmonella* vaccine vectors in which plasmids are maintained using single stranding binding protein (SSB) that is essential for DNA replication, recombination, and repair in *Salmonella*. (Chase J W, Williams K R. Single-stranded DNA binding proteins required for DNA replication. Annu Rev Biochem. 1986; 55:103-36; Lohman T M, Ferrari M E. *Escherichia coli* single-stranded DNA-binding protein: multiple DNA-binding modes and cooperativities. Annu Rev Biochem, 1994; 63: 527-70). We have shown that plasmids containing ssb are stably maintained by bacterial strains that lack ssb on their chromosome (Galen J E, Wang J Y, Chinchilla M, Vindurampulle C, Vogel J E, Levy H, et al. A new generation of stable nonantibiotic, low-copy-number plasmids improves immune responses to foreign antigens in *Salmonella enterica* serovar Typhi live vectors. Infect Immun. 2010; 78(1): 337-47). Therefore, we have established that ssb is absolutely required for replication (FIG. 9) and we have shown that we can genetically manipulate this essential gene.

Example 3. Genetic Engineering of Live Attenuated iNTS Vaccines

Aim 1. To genetically engineer our live attenuated iNTS vaccines, S. Typhimurium CVD 1931 and S. Enteritidis CVD 1944, such that ssb encoding the essential single stranded DNA-binding protein, SSB, will be transcriptionally regulated by a tightly controlled arabinose inducible promoter.

Figure 4:
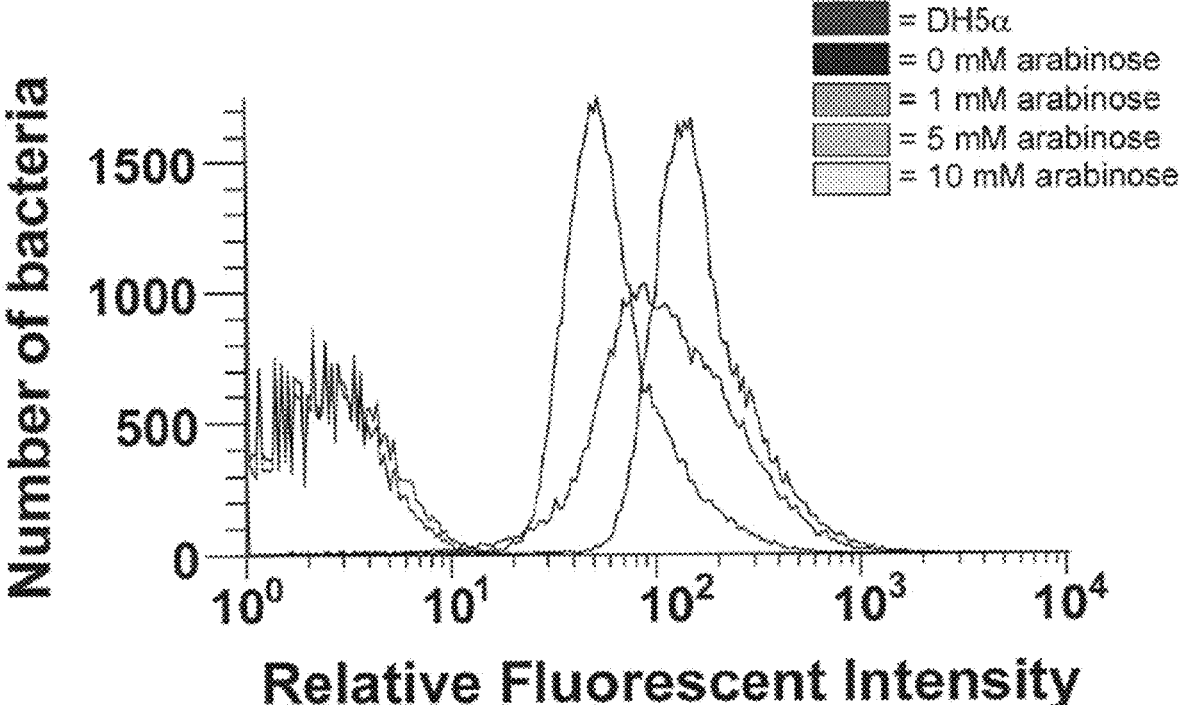
FIG. 4. araC-P$_{BAD}$-gfpuv is tightly controlled in vitro. Cultures of *E. coli* containing a high copy number pUC57 plasmid encoding araC-P$_{BAD}$-gfpuv were cultured in liquid medium containing increasing concentrations of arabinose. Cultures were then analyzed by flow cytometry and histograms plotted.

Genetic engineering of NTS such that ssb is controlled by an arabinose-inducible promoter. A synthetic TT-araC-$P_{BAD}$ transcription cassette (TT=transcription terminator) will be constructed and chromosomally integrated into S. Typhimurium CVD 1931 and S. Enteritidis CVD 1944 upstream of ssb, replacing only the ssb promoter ($P_{ssb}$) (FIG. 3A). To demonstrate tight transcriptional control of a gene downstream of the TT-araC-$P_{BAD}$, we engineered a synthetic TT-araC-$P_{BAD}$-gfpuv, inserted it into the high copy number pUC57 plasmid, and introduced this reporter plasmid into E. coli; expression of the GFPuv green fluorescence protein is therefore under the control of the concentration of arabinose in the growth medium. When plated onto solid medium containing increasing concentrations of arabinose, fluorescence is observed with increasing concentrations of arabinose (FIG. 3B). Cultures of E. coli containing this high copy number pUC57 plasmid encoding araC-$P_{BAD}$-gfpuv were then cultured in liquid medium containing increasing concentrations of arabinose. Samples from the resulting cultures were then analyzed by flow cytometry and histograms plotted (FIG. 4). Again, fluorescence was observed to increase with increasing concentrations of arabinose; the drop in fluorescence with 10 mM arabinose may be due to high levels of GFPuv expression leading to the formation of inclusion bodies which reduce fluorescence. Most importantly, fluorescence was NOT observed in the absence of arabinose, demonstrating tight transcriptional control of a downstream gene (in this case gfpuv) by the araC-$P_{BAD}$ promoter.

Having demonstrated that arabinose can be used to control transcription of a given gene, we will therefore fuse DNA that is homologous to DNA upstream of ssb to a kanamycin resistance gene flanked by FRT sites, followed by an araC-$P_{BAD}$ cassette, and inserted it upstream of the ssb gene to precisely replace the wildtype $P_{ssb}$ promoter. Integration into the Salmonella chromosome will be achieved by lambda Red recombination which we routinely use to create mutants and/or integrate genes into the chromosome.[105] The kanamycin resistance gene will subsequently be removed by using an-FRT-specific recombination enzyme to produce a completely antibiotic-susceptible recombinant vaccine strain. To determine the effect that this recombination has on the parental WT strains alone, we will also integrate the TT-araC-$P_{BAD}$ transcription cassette into S. Typhimurium D65 and S. Enteritidis R11 to create D65 $P_{BAD}$-ssb and R11 $P_{BAD}$-ssb. To mitigate the potential for overattenuating the vaccine strains, we will also integrate the TT-araC-$P_{BAD}$ transcription cassette into S. Typhimurium D65 ΔguaBA and S. Enteritidis R11 ΔguaBA to create D65 ΔguaBA $P_{BAD}$-ssb and R11 ΔguaBA $P_{BAD}$-ssb.

Optimization of recombinant NTS strains. We will also delete the arabinose catalytic enzymes ribulokinase (araB), isomerase (araA), and epimerase (araD). Deletion of araBAD is expected to prevent intracellular catabolism of imported arabinose, prolonging retention of intracellular arabinose and preventing cessation of replication too abruptly. We will delete the araBAD locus from S. Typhimurium strains D65, D65 $P_{BAD}$-ssb, D65 ΔguaBA, D65 ΔguaBA $P_{BAD}$-ssb, CVD 1931 and CVD 1931 $P_{BAD}$-ssb as well as S. Enteritidis strains R11, R11 $P_{BAD}$-ssb, R11 ΔguaBA, R11 ΔguaBA $P_{BAD}$-ssb, CVD 1944 and CVD 1944 $P_{BAD}$-ssb.

We will confirm the identity of all recombinant strains by PCR and DNA sequencing of all re-engineered chromosomal sites. We will sequence 500 bp upstream and downstream of the insertion/deletion to ensure that no unintended genetic changes occurred during homologous recombination. We will also confirm identity of these LANT strains by agglutination with grouping and typing sera, and will confirm by PCR that they possess the original guaBA and clpX attenuating deletions of the original vaccine constructs.

Aim 2. To evaluate our iNTS LANT vaccines in vitro.

Growth kinetics in bacteriological medium. First, we will perform growth curves in rich bacteriological medium and minimal medium, with and without arabinose. We anticipate that the iNTS LANT strains will grow similarly to their isogenic parental strains in media containing arabinose but that replication will quickly cease in media lacking arabinose.

Determine growth kinetics in cultured cells. We will determine replication in cultured cells (e.g., U937, THP-1 and J773 macrophages) to confirm arrest of replication intracellularly in the absence of arabinose. We will infect mammalian cells with 10:1 (bacteria:host cell) of our iNTS LANT strains and then determine the percentage of the inoculum that survive intracellularly at various time-points post-infection (e.g., 3 h, 8 h and 24 h) as we have previously determined for iNTS wild-type strains (Ramachandran G, Perkins D J, Schmidlein P J, Tulapurkar M E, Tennant S M. Invasive Salmonella Typhimurium ST313 with Naturally Attenuated Flagellin Elicits Reduced Inflammation and Replicates within Macrophages. PLoS Negl Trop Dis. 2015; 9(1): e3394). We will compare survival of our LANT strains with survival of the isogenic parental strains. We expect that intracellular replication of the iNTS LANT strains will rapidly cease due to the absence of arabinose within cultured cells.

Aim 3. To determine the in vivo persistence, immunogenicity, and protective efficacy of our iNTS vaccines in mice.

50% lethal dose. We will perform a 50% lethal dose experiment to determine the level of attenuation of the recombinant strains. The degree of attenuation of the recombinant strains will be compared to the isogenic wildtype NTS strain (S. Typhimurium D65 or S. Enteritidis R11), using the BALB/c mouse peroal (p.o) challenge model. We have chosen this model as 1) this is an established model for S. Typhimurium and S. Enteritidis, 2) we have a lot of experience using this particular model to evaluate our NTS strains including live attenuated NTS vaccines and 3) the peroral route represents the route by which humans are infected with NTS. (Tennant S M, Schmidlein P, Simon R, Pasetti M F, Galen J E, Levine M M. Refined live attenuated Salmonella enterica serovar Typhimurium and Enteritidis vaccines mediate homologous and heterologous serogroup protection in mice. Infect Immun. 2015; 83(12): 4504-12; Ramachandran G, Panda A, Higginson E E, Ateh E, Lipsky M M, Sen S, et al. Virulence of invasive Salmonella Typhimurium ST313 in animal models of infection. PLoS Negl Trap Dis. 2017; 11(8): e0005697; Tennant S M, Wang J Y, Galen J E, Simon R, Pasetti M F, Gat 0, et al. Engineering and preclinical evaluation of attenuated nontyphoidal Salmonella strains serving as live oral vaccines and as reagent strains. Infect Immun. 2011; 79(10): 4175-85; Higginson E E, Ramachandran G, Panda A, Shipley S T, Kriel E H, DeTolla U, et al. Improved Tolerability of a *Salmonella enterica* Serovar Typhimurium Live-Attenuated Vaccine Strain Achieved by Balancing Inflammatory Potential with Immunogenicity. Infect Immun. 2018; 86(12); Strugnell R A, Scott T A, Wang N, Yang C, Peres N, Bedoui S, et al. *Salmonella* vaccines: lessons from the mouse model or bad teaching? Curr Opin Microbiol. 2014; 17: 99-105; Higginson E E, Ramachandran G, Hazen T H, Kania D A, Rasko D A, Pasetti M F, et al. Improving Our Understanding of *Salmonella enterica* Serovar ParaTyphi B through the Engineering and Testing of a Live Attenuated Vaccine Strain. mSphere. 2018; 3(6); Fuche F J, Jones J A, Ramachandran G, Higginson E E, Simon R, Tennant S M. Deletions in guaBA and htrA but not clpX or rfaL constitute a live-attenuated vaccine strain of *Salmonella* Newport to protect against serogroup C2-C3 *Salmonella* in mice. Hum Vaccin Immunother. 2018:1-9).

We will infect groups (n=5) of six-to-8-week old BALB/c mice with a single dose of a 10-fold dilution (up to 6 doses; e.g., $10^4$, $10^5$, $10^6$, $10^7$, $10^8$, $10^9$) of our recombinant iNTS strains and then monitor mice for signs of morbidity for up to 30 days. Results will recorded as the lethal dose causing death in 50% of a group of animals ($LD_{50}$), calculated by linear regression analysis. In utilizing this mouse model, we broadly follow the guidelines recommended in the US Code of Federal Regulations for Food and Drugs, Title 21, Part 620.13 (c-d), 1986 for challenge of mice with S. Typhi.

Examine in vivo replication kinetics. We will evaluate in vivo replication of parental versus LANT strains in several ways.

1) Shedding. We will inoculate six-to-eight-week old BALB/c mice perorally and assess fecal shedding daily on days 1-7 and then on days 9, 11, 14 and 21. We have chosen these time-points based on previous data (see preliminary data, FIG. 9F). We will infect 10 mice per group perorally and then obtain fecal pellets on the designated days post-infection. We will place 2-3 stool pellets in PBS, vortex well and then spread plate on *Salmonella-Shigella* agar which is selective for *Salmonella*. We will determine the CFU/g of stool.

Figure 11:
FIG. 11. S. Typhimurium carrying pCM17 and visualized for luminescence. S. Typhimurium alone showed no luminescence.

2) In vivo bioluminescence imaging. We will monitor in vivo replication kinetics by using in vivo bioluminescence imaging. This technique has previously been used to evaluate infection kinetics of S. Typhimurium (Burns-Guydish S M, Olomu I N, Zhao H, Wong R J, Stevenson D K, Contag C H. Monitoring age-related susceptibility of young mice to oral *Salmonella enterica* serovar Typhimurium infection using an in vivo murine model. Pediatr Res. 2005; 58(1): 153-8). We are currently using this technique to examine in vivo infection kinetics of a candidate S. Typhimurium vaccine in infant mice. We will transform our NTS strains with plasmid pCM17 which encodes the luxCDABE operon (FIG. 11). (Morin C E, Kaper J B. Use of stabilized luciferase-expressing plasmids to examine in vivo-induced promoters in the *Vibrio cholerae* vaccine strain CVD 103-HgR. FEMS Immunol Med Microbiol. 2009; 57(1): 69-79). We will infect six-to-eight-week old BALB/c mice perorally and then evaluate in vivo bioluminescence using the Xenogen IVIS Spectrum Optical in vivo Imaging System which is available in the University of Maryland School of Medicine Center for Translational Research In Imaging (CTRIM) core facility. We will infect 3 mice per group and monitor mice daily for 7 days (or adjusted depending on the shedding data).

3) Bacterial load in deep organs. To confirm whether the bacteria that we observe in the in vivo bioluminescence imaging experiment are viable, we will determine bacterial load in various organs. We will infect six-to-eight-week old BALB/c mice perorally and then determine the bacterial load in various tissues (particularly the spleen and liver) at timepoints suggested by the shedding and imaging experiments (early, middle and late infection). We will euthanize mice and then harvest the spleen and liver, place in PBS, homogenize using a tissue homogenizer, and then spread plate on solid bacteriological medium. We will determine the CFU/g tissue.

Evaluate immunogenicity and protection. We will immunize BALB/c mice perorally with $10^9$ CFU of our NTS vaccine strains, three times, one month between each immunization. We routinely use this immunization schedule to evaluate immunogenicity of our NTS vaccines. We will evaluate anti-COPS and anti-FliC serum IgG and fecal IgA responses by ELISA. One month after the last immunization, we will challenge mice perorally with a low (100× $LD_{50}$) and high (10,000×$LD_{50}$) dose of wild-type S. Typhimurium D65 or S. Enteritidis R11 and determine vaccine efficacy. We will assess cell mediated immunity by measuring IFN-γ- and IL2-secreting cells stimulated ex-vivo with purified antigens and bacterial lysates using ELISpot assays. (Heine S J, Diaz-McNair J, Martinez-Becerra F J, Choudhari S P, Clements J D, Picking W L, et al. Evaluation of immunogenicity and protective efficacy of orally delivered *Shigella* type III secretion system proteins IpaD and Vaccine. 2013; 31(28); 2919-29; Ramirez K/Ditamo Y, Galen J E, Baillie L W, Pasetti M F. Mucosal priming of newborn mice with S. Typhi Ty21a expressing anthrax protective antigen (P A) followed by parenteral P A-boost induces B and T cell-mediated immunity that protects against infection bypassing maternal antibodies. Vaccine. 2010; 28(37): 6065-75. We will also measure cytokines released by splenocytes stimulated in vitro with SseB and FliC using an MSD® Mouse Th1/Th2 Multiarray® tissue culture kit (Meso Scale Discovery), as previously described (Heine S J Diaz-McNair J, Andar A U, Drachenberg C B, van de Verg L, Walker R, et al. Intradermal delivery of *Shigella* IpaB and IpaD type III secretion proteins: kinetics of cell recruitment and antigen uptake, mucosal and systemic immunity, and protection across serotypes. J Immunol. 2014; 192(4); 1630-40).

Desired characteristics of the candidate iNTS LANT vaccines:

1. Shedding in stool for 3 days or less,
2. At least four-fold seroconversion in anti-LPS serum IgG titers in >70% of animals, and
3. Greater than or equal to 70% vaccine efficacy However, the main risk to the project is the over-attenuation of LANT strains. To mitigate this risk, we will genetically engineer our preferred vaccine strains (ΔguaBA ΔclpX) and will also engineer strains which harbor a ΔguaBA mutation only. This will allow us to identify at least one strain that demonstrates that critical balance between attenuation and immunogenicity. Indeed, we may observe that the balance may be different for S. Typhimurium versus S. Enteritidis.

By the end of the project period, we will have developed non-transmissible iNTS live vaccine candidates. Beyond this funding, the following tasks would be required to advance a bivalent live attenuated iNTS vaccine comprised of a mixture of S. Typhimurium and S. Enteritidis LANT strains:

1) Prepare a Master Cell Bank (MCB) and a Working Cell Bank (WCB) of our live attenuated iNTS vaccines under current good manufacturing practices (GMP) and to characterize the MCB.

2) Generate all non-clinical laboratory and animal model data with our live attenuated iNTS vaccines necessary to submit an Investigational New Drug (IND) Application to the Center for Biologics Evaluation and Research (CBER) of the U.S. Food and Drug Administration (FDA).

3) Carry out pre-GMP process development and scale-up with our live attenuated iNTS vaccines to identify the transferrable processes that will allow a Contract Manufacturing Organization (CMO) to manufacture a GMP pilot lot of vaccine for a Phase I (and future Phase II) clinical trials.

4) Large-scale GMP production of a pilot lot of our live attenuated iNTS vaccines yielding ~2000 vials of lyophilized vaccine, with ~2-8×10$^9$ colony forming units (CFU) per vial.

5) Prepare and file an IND to the FDA to undertake clinical trials with our live attenuated iNTS vaccines, commencing with a Phase I study in US adults under physical containment.

6) Perform a sequential, Phase I, dose-escalation (10$^7$, 10$^8$, & 10$^9$ CFU) study in healthy US adults under physical containment to preliminarily assess the safety, excretion pattern, lack of transmissibility (to contact controls who receive placebo) and immunogenicity of our live attenuated iNTS vaccines administered with NaHCO$_3$ buffer. At each dosage level there will be 8 vaccinees and 2 placebo (NaHCO$_3$ buffer alone) contact controls; total 30 subjects. Successful completion of the Phase I trial in US adults under containment paves the way for Phase II trials in community subjects without the need for containment. To progress to Phase II, we must document safety and a lack of transmissibility.

Figure 12:
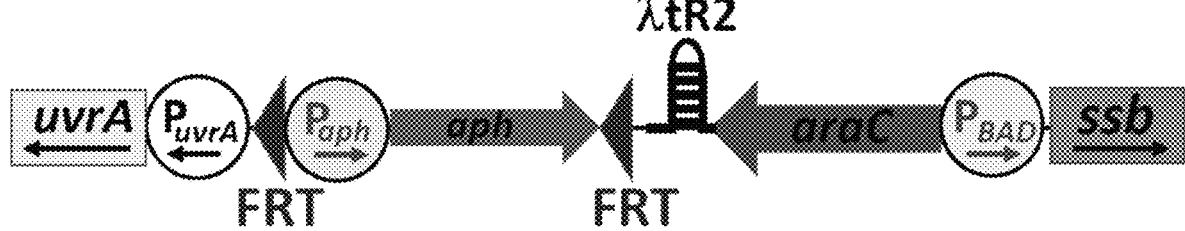
FIG. 12. Schematic diagram of the chromosomal crossover cassette engineered to replace the chromosomal wild type P$_{ssb}$ promoter with a synthetic araC-P$_{BAD}$ promoter cassette, encoding the AraC repressor. Genes are color coded to match the corresponding sequences listed in SEQ ID NO:1. Triangles labeled FRT represent the FRT recombination sites recognized by the FLP recombinase to remove the aph cassette encoding resistance to kanamycin. The stem-loop labeled λtR2 represents a rho-independent transcriptional terminator reported to terminate ~75% of transcription across this terminator[2]. Arrows under designated promoters indicate the direction of transcription.

Example 4. Development of *Salmonella enterica* Serovar Typhimurium D65 LANT Strain To test the concept of arabinose-regulated control of the growth of a pathogenic invasive non-typhoidal *Salmonella* (iNTS) strain, we first chose the wild type clinical isolate D65 for proof-of-concept studies. Using the lambda Red site-specific recombination system we replaced the wild type P$_{ssb}$ promoter with a synthetic araC-P$_{BAD}$ promoter cassette, encoding the AraC repressor. A crossover cassette was engineered (SEQ ID NO:1; FIG. 12) such that the wild type P$_{ssb}$ promoter was first replaced with araC-P$_{BAD}$ promoter cassette carrying an aph gene (flanked by FRT recombination sites and encoding resistance to kanamycin) in order to select for the crossover event in the presence of kanamycin; this aph antibiotic resistance cassette was subsequently removed as previously described[1] using FLP recombinase, leaving a single copy of the FRT site in the chromosome.

AraC is a transcriptional repressor that binds to the P$_{BAD}$ promoter in the absence of arabinose to terminate transcription. Therefore, replacing the wild type P$_{ssb}$ promoter with the araC-P$_{BAD}$ promoter cassette renders transcription of ssb (encoding the essential single stranded binding protein SSB) under the tight control of arabinose in the growth medium. We reasoned that attenuated vaccine strains controlled in this manner could be grown up in liquid medium containing arabinose, and then purified for oral vaccination. After oral administration, the vaccine strain would exhaust intracellular supplies of arabinose, enabling AraC to bind to the P$_{BAD}$ promoter and shut down synthesis of SSB. The vaccine strain would therefore undergo replication for a few generations in the gastrointestinal tract before growth ceased. The resulting bacteria would be metabolically active but unable to grow any further. Therefore, no viable organisms would be shed from the gastrointestinal tract after excretion.

Using this strategy, we constructed a *Salmonella enterica* serovar Typhimurium (S. Typhimurium) D65 LANT strain designated here as D65Δssb::araC-P$_{BAD}$. We also constructed an isogenic strain of D65 in which the araBAD operon was first deleted prior to introduction of the araC-P$_{BAD}$ promoter cassette. The AraB, AraA, and AraD proteins are responsible for metabolism of arabinose as a carbon source. We hypothesized that the resulting LANT strain D65ΔaraBAD Δssb::araC-P$_{BAD}$ would not be able to metabolize any intracellular reserves of arabinose and would therefore grow for a slightly longer period of time in the absence of arabinose versus D65Δssb::araC-P$_{BAD}$. The expected genetic identities of these isogenic LANT strains were confirmed by DNA sequencing of targeted regions to rule out any unintended deletion or disruption of flanking chromosomal genes. Based on homology of flanking ssb regions between *Salmonella enterica* serovar Typhimurium and *S. enterica* serovar Enteritidis, we will be able to use the same crossover cassette described here for future replacement of S. Enteritidis P$_{ssb}$ with araC-P$_{BAD}$. See SEQ ID NO:5.

Example 5. Assay for Arabinose Inducible Growth

Figure 13:
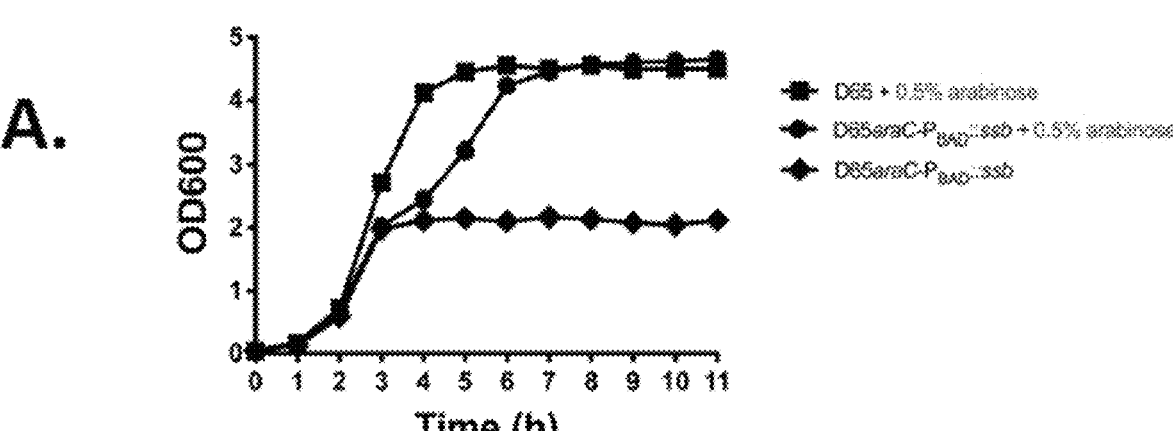
FIG. 13. Growth curves for wildtype and LANT strains grown at 37° C., 220 RPM in the presence or absence of 0.5% arabinose. Solid shapes represent growth curves for wild type D65 strains (A); open shapes represent growth curves for wild type D65ΔaraBAD strains (B). Growth is determined by optical density measured at 600 nm (OD600) for measurements taken each hour (h).
Figure 13:
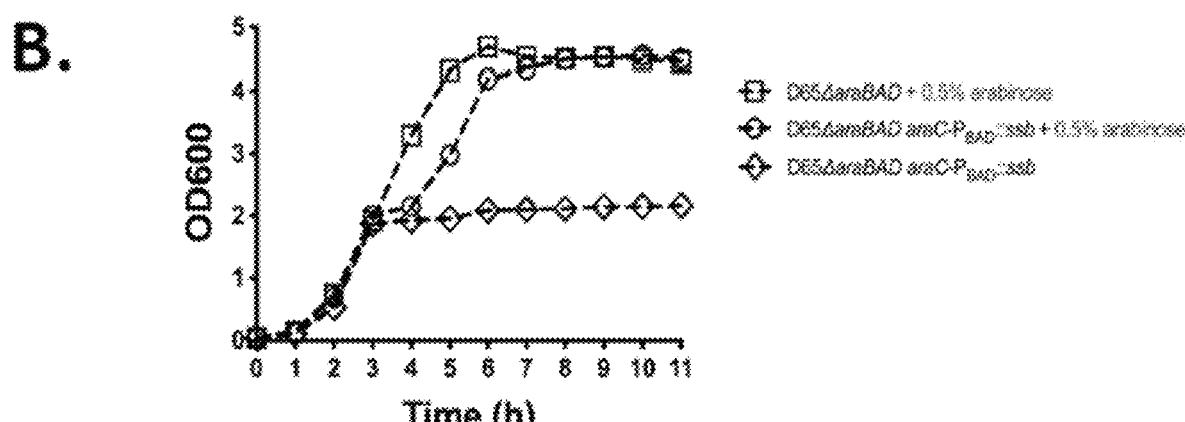
Figure 14:
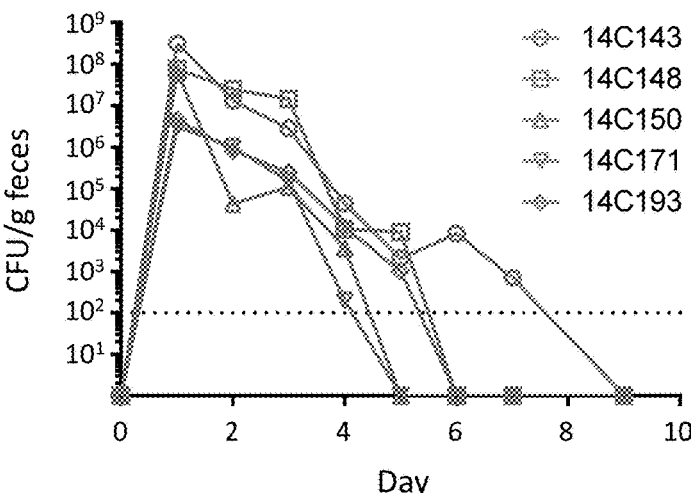
FIG. 14. Shedding of live attenuated *Salmonella* vaccines.
Figure 17:
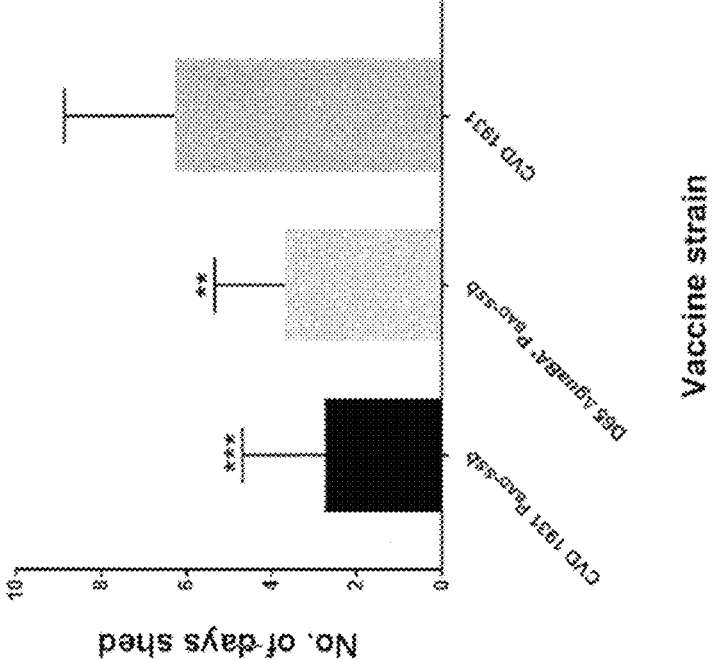
FIG. 17. Shedding of CVD 1931 $P_{BAD}$-ssb and D65 guaBA*$P_{BAD}$-ssb.
Figure 17:
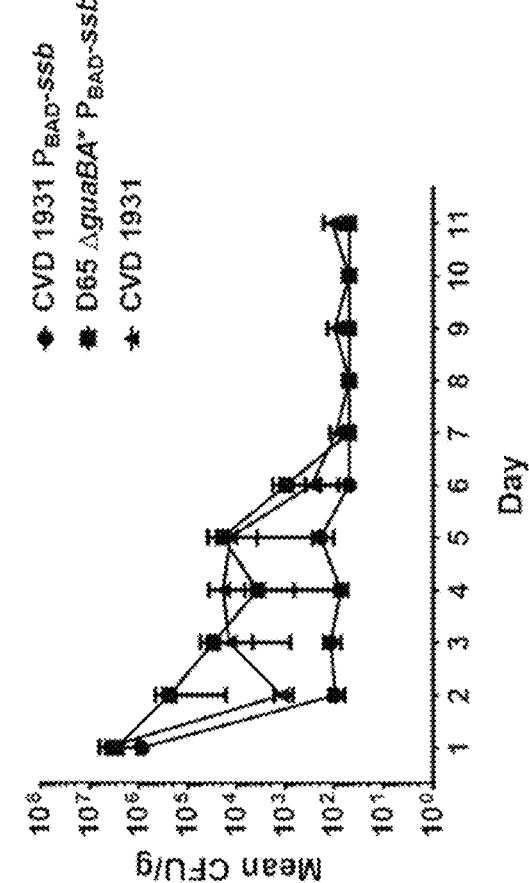
Figures 18, 19:
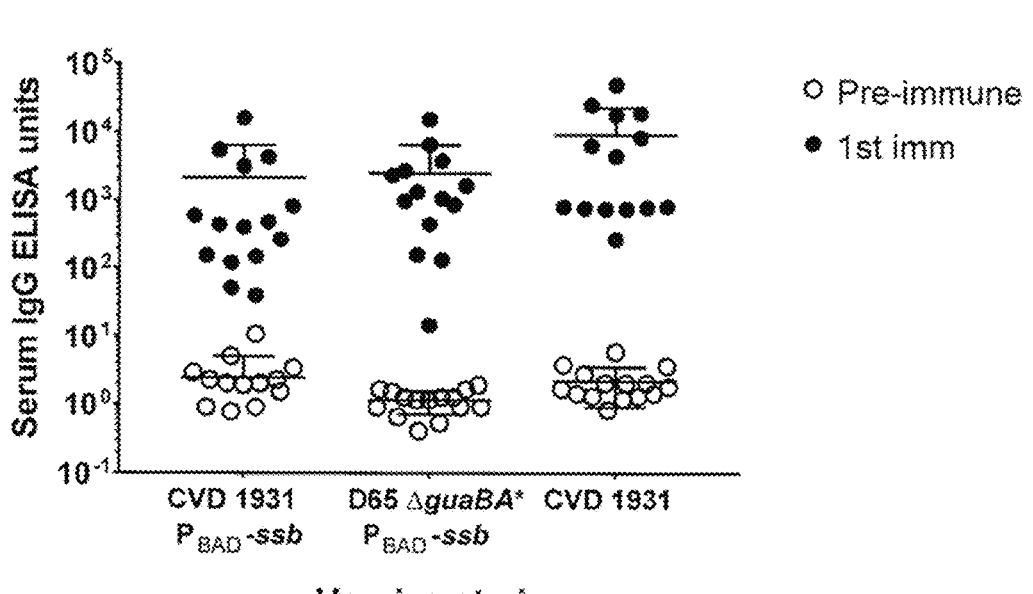
FIG. 18. Percent of mouse shedders.
FIG. 19. Anti-LPS serum IgG responses elicited by CVD 1931 $P_{BAD}$-ssb are comparable to CVD 1931 in BALB/c mice.
Figure 20:
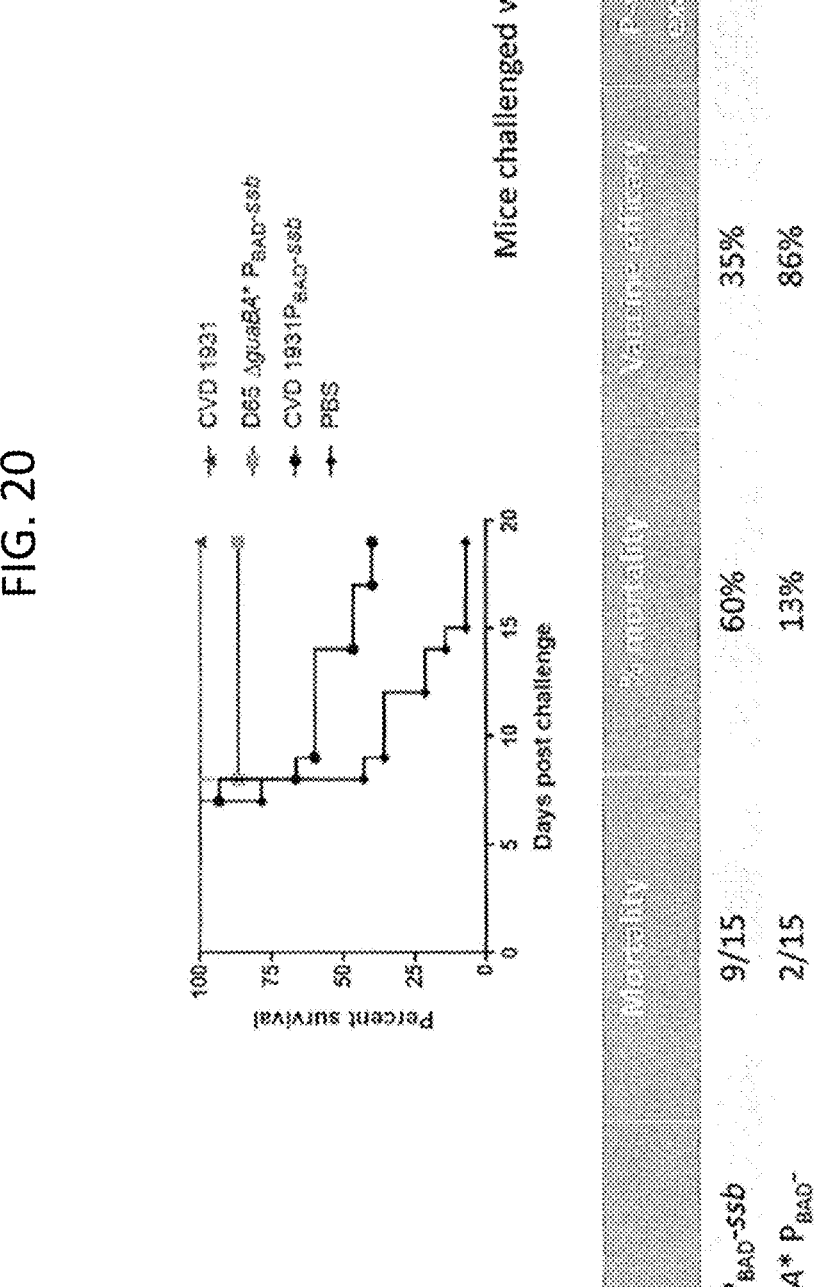
FIG. 20. Vaccine efficacy.
Figure 20:
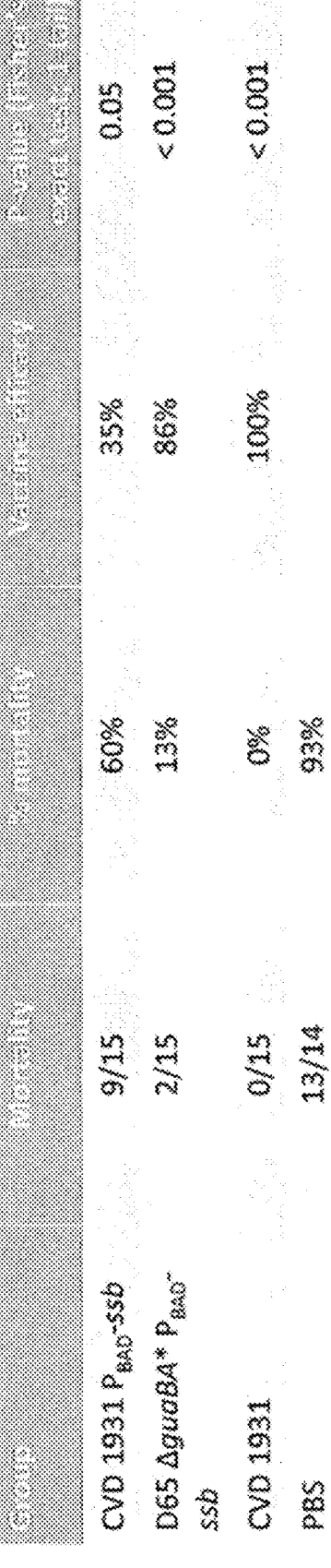

To test the effect of arabinose on the growth of D65Δssb:: araC-P$_{BAD}$ and D65ΔaraBAD Δssb::araC-P$_{BAD}$, frozen isolates of four strains were examined: 1] wild type D65, 2] D65Δssb::araC-P$_{BAD}$, 3] D65ΔaraBAD, and 4] D65ΔaraBAD Δssb::araC-P$_{BAD}$. All strains were first streaked for isolation on solid medium containing 0.5% arabinose and incubated overnight at 37° C. Isolated colonies of uniform size were then picked and subcultured in liquid medium containing 0.5% arabinose; cultures were then incubated overnight at 37° C. in an orbital shaker at 220 RPM. Cultures were then normalized by optical density (OD600) to 0.05, subcultured into 50 ml liquid medium in the presence or absence of 0.5% arabinose, and grown at 37° C., 220 RPM. Samples of each culture (1 ml) were removed every hour for 11 hours and OD600 determined. Plots for each LANT strain are shown in FIG. 13. All cultures grew normally until around 3 hours, at which point the LANT strains begin to diverge. Wildtype D65 and D65ΔaraBAD strains continue to increase exponentially in the presence of 0.5% arabinose, while the LANT strains display a biphasic growth curve between 3 and 4 hours in the presence of arabinose that eventually reaches the same OD600 as the wildtype strains between 7 and 11 hours. However, in the absence of arabinose, the LANT strains do not increase in density after 3 hours; OD600 measurements do not increase further for either D65Δssb::araC-P BAD and D65ΔaraBAD Δssb::araC-P$_{BAD}$ in the absence of arabinose.

Example 6. Growth of Strains in the Absence of Arabinose

To determine if LANT strains remained viable in the absence of arabinose, the growth of D65Δssb::araC-P$_{BAD}$ and D65ΔaraBAD Δssb::araC-P$_{BAD}$ was re-examined. These isogenic LANT strains were first streaked for isolation on solid medium containing 0.5% arabinose and incubated overnight at 37° C. Isolated colonies of uniform size were then picked and subcultured in liquid medium in the presence or absence of 0.5% arabinose and again subcultured overnight at 37° C. Viable counts for each culture were then determined. Results are seen in the table below.

| STRAIN | 0.5% ara | OD$_{600}$ (CFU/ml) |
|---|---|---|
| D65Δssb::araC-P$_{BAD}$ | – | 5.5 × 10$^3$ |
|  | + | 6.0 × 10$^8$ |

-continued

| STRAIN | 0.5% ara | OD$_{600}$ (CFU/ml) |
|---|---|---|
| D65ΔaraBAD Δssb::araC-P$_{BAD}$ | – | 2.0 × 10$^3$ |
|  | + | 4.0 × 10$^8$ |

Although LANT strains grown in the absence of arabinose remain viable, viable counts are 5 log 10 lower than the identical strain grown in the presence of 0.5% arabinose. In addition, deletion of the araBAD operon does not seem to affect the persistence of this LANT strain in the absence of arabinose. These data suggest that the LANT strains remain metabolically active in the absence of arabinose but do not appear to replicate or lyse. When rescued with arabinose, viable colonies can be recovered.

We claim:

1. A genetically modified *Salmonella enterica* microorganism having reduced fecal-oral transmission, wherein the microorganism has been genetically modified to express a single stranded binding protein (SSB) regulated by a promoter that is responsive to arabinose, wherein the *Salmonella enterica* microorganism has a reduced growth capacity in the absence of arabinose, wherein the promoter is a $P_{BAD}$ promoter, wherein the microorganism has been further modified to reduce expression of endogenous AraB, AraA, and/or AraD, wherein an endogenous araBAD operon is deleted in the microorganism.

2. The genetically modified microorganism of claim 1, wherein the growth capacity is reduced by at least 50% in the absence of arabinose.

3. The genetically modified microorganism of claim 1, wherein the microorganism has been modified to express AraC.

4. The genetically modified microorganism of claim 1, wherein the PBAD promoter replaces the wild-type Pssb promoter.

5. The genetically modified microorganism of claim 1, wherein the endogenous ssb gene is inactivated or deleted.

6. The genetically modified microorganism of claim 1, wherein the *Salmonella enterica* is a typhoidal *Salmonella* strain.

7. The genetically modified microorganism of claim 6, wherein the *Salmonella enterica* is S. Typhi, S. Paratyphi A, and/or S. Paratyphi B.

8. The genetically modified microorganism of claim 1, wherein the *Salmonella enterica* is a non-typhoidal *Salmonella* (NTS) strain.

9. The genetically modified microorganism of claim 8, wherein the non-typhoidal *Salmonella* is selected from S. Typhimurium and S. Enteritidis.

10. The genetically modified microorganism of claim 1, wherein the microorganism comprises a mutation at a locus selected from the group consisting of guaBA, aroC, aroD, clpP, clpX, htrA, pipA, one or more capsular biosynthesis machinery genes, and combinations thereof.

11. A pharmaceutical composition comprising the genetically modified microorganism of claim 1 and a pharmaceutically acceptable carrier.

12. A method of inducing an immune response in a subject, comprising administering to the subject an immunologically-effective amount of the pharmaceutical composition of claim 11.

13. The method of claim 11, wherein the pharmaceutical composition is orally administered.

14. The method of claim 11, wherein the pharmaceutical composition is intranasally administered.

15. The method of any of claim 12, wherein the genetic modification reduces fecal-oral transmission of the genetically modified microorganism.

16. The method of any of claim 12, comprising administering a combination of genetically modified microorganisms.

17. The method of claim 16, wherein the combination comprises a plurality of non-typhoidal *Salmonella* (NTS) strains.

18. The method of claim 17, wherein the combination comprises S. Typhimurium, S. Enteritidis S. Dublin, and S. Cholerasuis.

*    *    *    *    *

SEQUENCE LISTING

<160> NUMBER OF SEQ ID NOS: 15

<210> SEQ ID NO 1
<211> LENGTH: 631
<212> TYPE: DNA
<213> ORGANISM: Salmonella enterica

<400> SEQUENCE: 1

```
gagtgacctg gaacctgcat cgcagctatt aaaatgctac gtggaaatgg tacactcacg      60
cgtttacact atttatgaaa cgtattcagg agactcaatt atggccagca gaggcgtaaa     120
caaggtgatt ctcgttggta atctgggcca ggacccggaa gtacgctata tgccgagtgg     180
cggcgctgtc gccaacttaa cgctggctac ttctgaatcc tggcgcgata agcagaccgg     240
cgaaatgaaa gagcagactg aatggcaccg ggtggtgatg ttcggcaaac tggcggaagt     300
ggccggcgaa tatctgcgta aaggttctca ggtgtatatc gaaggtcaat tgcgtacccg     360
caagtggacc gatcagagtg gccaggaacg ctatacgact gaaattaacg ttccgcagat     420
cggcggcgtg atgcagatgc tgggtggtcg ccagggcggc ggcgcaccgg caggcggtca     480
gcagcagggg ggttggggtc agccgcaaca acctcagcag ccgcagggcg gcaaccagtt     540
cagcggcggc gcgcagtcgc gtccacagca atccgcgcca gcgccgtcta acgaaccgcc     600
aatggatttt gacgacgaca ttccgttctg a                                    631
```

<210> SEQ ID NO 2
<211> LENGTH: 176
<212> TYPE: PRT
<213> ORGANISM: Salmonella enterica

<400> SEQUENCE: 2

```
Met Ala Ser Arg Gly Val Asn Lys Val Ile Leu Val Gly Asn Leu Gly
1               5                   10                  15

Gln Asp Pro Glu Val Arg Tyr Met Pro Ser Gly Gly Ala Val Ala Asn
            20                  25                  30

Leu Thr Leu Ala Thr Ser Glu Ser Trp Arg Asp Lys Gln Thr Gly Glu
        35                  40                  45

Met Lys Glu Gln Thr Glu Trp His Arg Val Val Met Phe Gly Lys Leu
    50                  55                  60

Ala Glu Val Ala Gly Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Glu
                85                  90                  95
```

```
Arg Tyr Thr Thr Glu Ile Asn Val Pro Gln Ile Gly Gly Val Met Gln
        100                 105                 110

Met Leu Gly Gly Arg Gln Gly Gly Gly Ala Pro Ala Gly Gly Gln Gln
    115                 120                 125

Gln Gly Gly Trp Gly Gln Pro Gln Gln Pro Gln Gln Pro Gln Gly Gly
    130                 135                 140

Asn Gln Phe Ser Gly Gly Ala Gln Ser Arg Pro Gln Gln Ser Ala Pro
145                 150                 155                 160

Ala Pro Ser Asn Glu Pro Pro Met Asp Phe Asp Asp Asp Ile Pro Phe
                165                 170                 175
```

<210> SEQ ID NO 3
<211> LENGTH: 1174
<212> TYPE: DNA
<213> ORGANISM: Artificial sequence
<220> FEATURE:
<223> OTHER INFORMATION: araC-pbad

<400> SEQUENCE: 3

```
ctattattca catccggcgc ggaactcgct aggacttgcc ccggtgcatt ttttaaatac      60
gcgcgaaaaa tagagctgat cgtcaaatcc aacattgcgc ccaacggtcg ctatcggcat     120
acgcgtagtg ctaagcagaa gtttcgcctg gctgatacgc tgatcttcgc gccagctcaa     180
tacgctaatg cctaactgct ggcggaacag atgtgataaa cgggacggcg acaggcagac     240
atgctgggcg acgctggcga tatcaaaatg gctgtccgcc agatggtcgc tgatatactg     300
gcaggcatca cgcacacggc tatccatcgg cggatgcaac gactcattaa ttaccgccat     360
gcgacggagc aacaactgct ccagcagatt gatcgccagc agctcagaat agcgaccttc     420
cccttgcccg cgctgatga tctgcccgaa cagttcgctg aaatgcggct ggcgcgcctc     480
gtccgggcgg aaaaatcctg tctgggcaaa gattgtcggc caggtcagcc actcctgcca     540
gtaggcgcga ggacggaaat aaacccactg atgataccac tcgctggcgt ccggatgacg     600
tccatagtga tgaatctcgc ccggcggaaa caataatata tcgccaggac gacagacaaa     660
ctgctcgcca ttattattaa tgacgccctc tccgcggatg gtcaggttaa gaatatatcc     720
cttcatgccc aacggacgat cgataaaaaa atccagatat ccattcgctt caatcggcgt     780
cagcccggcg accagatggg cattaaatga atatcccggc aacagcggat cattttgcgt     840
ttcagccatg atttctctac cccccgatgt tcagagaaga aacaaattgt ccatatcgac     900
caggacgaca gagcttccgt ctccgcaaga ctttgcgctt gatgaaagca cgtatcaacc     960
ccgcttgtga aaagcgcttt gtaacaaaag cgtacagttc aggcgataaa attaagtaac    1020
agaagtgtct ataactatgg ctggaatgtc cacattgaat atttgcacag cgtcacactt    1080
tgcaaagcat tagcattttt gtccataaga ttagcggatc ctgcctgacg gttttttgccg    1140 cgactctcta ctgtttctcc atacctgttt ttct                                 1174
```

<210> SEQ ID NO 4
<211> LENGTH: 279
<212> TYPE: PRT
<213> ORGANISM: Salmonella enterica

<400> SEQUENCE: 4

```
Met Ala Glu Thr Gln Asn Asp Pro Leu Leu Pro Gly Tyr Ser Phe Asn
1               5                   10                  15

Ala His Leu Val Ala Gly Leu Thr Pro Ile Glu Ala Asn Gly Tyr Leu
            20                  25                  30
```

```
Asp Phe Phe Ile Asp Arg Pro Leu Gly Met Lys Gly Tyr Ile Leu Asn
            35              40              45

Leu Thr Ile Arg Gly Glu Gly Val Ile Asn Asn Asn Gly Glu Gln Phe
        50              55              60

Val Cys Arg Pro Gly Asp Ile Leu Leu Phe Pro Pro Gly Glu Ile His
65              70              75              80

His Tyr Gly Arg His Pro Asp Ala Ser Glu Trp Tyr His Gln Trp Val
                85              90              95

Tyr Phe Arg Pro Arg Ala Tyr Trp Gln Glu Trp Leu Thr Trp Pro Thr
            100             105             110

Ile Phe Ala Gln Thr Gly Phe Phe Arg Pro Asp Glu Ala Arg Gln Pro
        115             120             125

His Phe Ser Glu Leu Phe Gly Gln Ile Ile Ser Ala Gly Gln Gly Glu
        130             135             140

Gly Arg Tyr Ser Glu Leu Leu Ala Ile Asn Leu Leu Glu Gln Leu Leu
145             150             155             160

Leu Arg Arg Met Ala Val Ile Asn Glu Ser Leu His Pro Pro Met Asp
                165             170             175

Ser Arg Val Arg Asp Ala Cys Gln Tyr Ile Ser Asp His Leu Ala Asp
            180             185             190

Ser His Phe Asp Ile Ala Ser Val Ala Gln His Val Cys Leu Ser Pro
        195             200             205

Ser Arg Leu Ser His Leu Phe Arg Gln Gln Leu Gly Ile Ser Val Leu
        210             215             220

Ser Trp Arg Glu Asp Gln Arg Ile Ser Gln Ala Lys Leu Leu Leu Ser
225             230             235             240

Arg Met Pro Ile Ala Thr Val Gly Arg Asn Val Gly Phe Asp Asp Gln
            245             250             255

Leu Tyr Phe Ser Arg Val Phe Lys Lys Cys Thr Gly Ala Ser Pro Ser
            260             265             270

Glu Phe Arg Ala Gly Cys Glu
            275
```

```
<210> SEQ ID NO 5
<211> LENGTH: 3528
<212> TYPE: DNA
<213> ORGANISM: Artificial sequence
<220> FEATURE:
<223> OTHER INFORMATION: synthetic cassette

<400> SEQUENCE: 5
gaattccccg ggcacgtcat gatccggaca acgcggctcg cccacgcggg caaacagcag      60
gcgcaggtag tcgtggatct cggtaatagt acccaccgta gagcgcgggt tgtgcgatgt     120
cgatttctgt tcaatgctga tcgcgggcga tagcccctca atatggtcga catccggttt     180
ttccatgagc gacaaaaact gccgcgcgta agcggagagc gattcaacgt aacgacgctg     240
cccttcggca tacagagtgt cgaaagccag tgaggatttg cctgaacccg aaagcccggt     300
cacgacaatc agtttgtcgc gggggatgac gaggttaata ttttttgagat tatgggtgcg     360 ggcgccccga acttcgatct tatccattca cctttcccgg tagagactcg gatgcctggt     420
ttgtttgaag acaaacggc agaaacggct aattatgaca caatttaacc tgtttgaata     480
tacagtattg cctagtggat ccgtcgacct gcagttcgaa gttcctattc tctagaaagt     540
ataggaactt cagagcgctt ttgaagctca cgctgccgca agcactcagg gcgcaagggc     600
tgctaaagga agcggaacac gtagaaagcc agtccgcaga aacggtgctg accccggatg     660
```

-continued

```
aatgtcagct actgggctat ctggacaagg gaaaacgcaa gcgcaaagag aaagcaggta      720
gcttgcagtg ggcttacatg gcgatagcta gactgggcgg ttttatggac agcaagcgaa      780
ccggaattgc cagctggggc gccctctggt aaggttggga agccctgcaa agtaaactgg      840
atggctttct tgccgccaag gatctgatgg cgcaggggat caagatctga tcaagagaca      900
ggatgaggat cgtttcgcat gattgaacaa gatggattgc acgcaggttc tccggccgct      960
tgggtggaga ggctattcgg ctatgactgg gcacaacaga caatcggctg ctctgatgcc     1020
gccgtgttcc ggctgtcagc gcaggggcgc ccggttcttt ttgtcaagac cgacctgtcc     1080
ggtgccctga atgaactgca ggacgaggca gcgcggctat cgtggctggc cacgacgggc     1140
gttccttgcg cagctgtgct cgacgttgtc actgaagcgg aagggactg gctgctattg     1200 ggcgaagtgc cggggcagga tctcctgtca tctcaccttg ctcctgccga aaagtatcc     1260 atcatggctg atgcaatgcg gcggctgcat acgcttgatc cggctacctg cccattcgac     1320
caccaagcga aacatcgcat cgagcgagca cgtactcgga tggaagccgg tcttgtcgat     1380
caggatgatc tggacgaaga gcatcagggg ctcgcgccag ccgaactgtt cgccaggctc     1440
aaggcgcgca tgcccgacgg cgaggatctc gtcgtgaccc atggcgatgc ctgcttgccg     1500
aatatcatgg tggaaaatgg ccgcttttct ggattcatcg actgtggccg gctgggtgtg     1560
gcggaccgct atcaggacat agcgttggct acccgtgata ttgctgaaga gcttggcggc     1620
gaatgggctg accgcttcct cgtgctttac ggtatcgccg ctcccgattc gcagcgcatc     1680
gccttctatc gccttcttga cgagttcttc taataagggg atcttgaagt tcctattccg     1740
aagttcctat tctctagaaa gtataggaac ttcgaagcag ctccagcgct aggaaataaa     1800
aaggcctgcg attaccagca ggcctgttat tagctcagta ctattattca catccggcgc     1860
ggaactcgct aggacttgcc ccggtgcatt ttttaaatac gcgcgaaaaa tagagctgat     1920
cgtcaaatcc aacattgcgc ccaacggtcg ctatcggcat acgcgtagtg ctaagcagaa     1980
gtttcgcctg gctgatacgc tgatcttcgc gccagctcaa tacgctaatg cctaactgct     2040
ggcggaacag atgtgataaa cgggacggcg acaggcagac atgctgggcg acgctggcga     2100
tatcaaaatg gctgtccgcc agatggtcgc tgatatactg gcaggcatca cgcacacggc     2160
tatccatcgg cggatgcaac gactcattaa ttaccgccat gcgacggagc aacaactgct     2220
ccagcagatt gatcgccagc agctcagaat agcgaccttc cccttgcccg cgctgatga     2280 tctgcccgaa cagttcgctg aaatgcggct ggcgcgcctc gtccgggcgg aaaaatcctg     2340
tctgggcaaa gattgtcggc caggtcagcc actcctgcca gtaggcgcga ggacggaaat     2400
aaacccactg atgataccac tcgctggcgt ccggatgacg tccatagtga tgaatctcgc     2460
ccggcggaaa caataatata tcgccaggac gacagacaaa ctgctcgcca ttattattaa     2520
tgacgccctc tccgcggatg gtcaggttaa gaatatatcc cttcatgccc aacggacgat     2580
cgataaaaaa atccagatat ccattcgctt caatcggcgt cagcccggcg accagatggg     2640
cattaaatga atatcccggc aacagcggat cattttgcgt ttcagccatg atttctctac     2700
cccccgatgt tcagagaaga aacaaattgt ccatatcgac caggacgaca gagcttccgt     2760
ctccgcaaga ctttgcgctt gatgaaagca cgtatcaacc ccgcttgtga aaagcgcttt     2820
gtaacaaaag cgtacagttc aggcgataaa attaagtaac agaagtgtct ataactatgg     2880
ctggaatgtc cacattgaat atttgcacag cgtcacactt tgcaaagcat tagcattttt     2940
gtccataaga ttagcggatc ctgcctgacg gttttttgccg cgactctcta ctgtttctcc     3000
```

```
atacctgttt ttctcaattg atgaaacgta ttcaggagac tcaattatgg ccagcagagg    3060
cgtaaacaag gtgattctcg ttggtaatct gggccaggac ccggaagtac gctatatgcc    3120
gagtggcggc gctgtcgcca acttaacgct ggctacttct gaatcctggc gcgataagca    3180
gaccggcgaa atgaaagagc agactgaatg gcaccgggtg gtgatgttcg gcaaactggc    3240
ggaagtggcc ggcgaatatc tgcgtaaagg ttctcaggtg tatatcgaag gtcagttgcg    3300
tacccgcaag tggaccgatc agagtggcca ggaacgctat acgactgaaa ttaacgttcc    3360
gcagatcggc ggcgtgatgc agatgctggg tggtcgccag ggcggcggcg caccggcagg    3420
cggtcagcag caggggggtt ggggtcagcc gcaacaacct cagcagccgc agggcggcaa    3480
ccagttcagc ggcggcgcgc agtcgcgtcc acagcaatgc atgaattc                 3528
```

```
<210> SEQ ID NO 6
<211> LENGTH: 1273
<212> TYPE: PRT
<213> ORGANISM: Sars-CoV-2

<400> SEQUENCE: 6

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285
```

-continued

```
Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
                340                 345                 350

Trp Asn Arg Lys Arg Ile Ser Asn Cys Val Ala Asp Tyr Ser Val Leu
                355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
    435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
                515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
    675                 680                 685

Ser Gln Ser Ile Ile Ala Tyr Thr Met Ser Leu Gly Ala Glu Asn Ser
    690                 695                 700
```

-continued

```
Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
                725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
        755             760             765

Gly Ile Ala Val Glu Gln Asp Lys Asn Thr Gln Glu Val Phe Ala Gln
    770             775             780

Val Lys Gln Ile Tyr Lys Thr Pro Pro Ile Lys Asp Phe Gly Gly Phe
785             790             795             800

Asn Phe Ser Gln Ile Leu Pro Asp Pro Ser Lys Pro Ser Lys Arg Ser
            805             810             815

Phe Ile Glu Asp Leu Leu Phe Asn Lys Val Thr Leu Ala Asp Ala Gly
            820             825             830

Phe Ile Lys Gln Tyr Gly Asp Cys Leu Gly Asp Ile Ala Ala Arg Asp
        835             840             845

Leu Ile Cys Ala Gln Lys Phe Asn Gly Leu Thr Val Leu Pro Pro Leu
    850             855             860

Leu Thr Asp Glu Met Ile Ala Gln Tyr Thr Ser Ala Leu Leu Ala Gly
865             870             875             880

Thr Ile Thr Ser Gly Trp Thr Phe Gly Ala Gly Ala Ala Leu Gln Ile
            885             890             895

Pro Phe Ala Met Gln Met Ala Tyr Arg Phe Asn Gly Ile Gly Val Thr
            900             905             910

Gln Asn Val Leu Tyr Glu Asn Gln Lys Leu Ile Ala Asn Gln Phe Asn
        915             920             925

Ser Ala Ile Gly Lys Ile Gln Asp Ser Leu Ser Ser Thr Ala Ser Ala
    930             935             940

Leu Gly Lys Leu Gln Asp Val Val Asn Gln Asn Ala Gln Ala Leu Asn
945             950             955             960

Thr Leu Val Lys Gln Leu Ser Ser Asn Phe Gly Ala Ile Ser Ser Val
            965             970             975

Leu Asn Asp Ile Leu Ser Arg Leu Asp Lys Val Glu Ala Glu Val Gln
            980             985             990

Ile Asp Arg Leu Ile Thr Gly Arg  Leu Gln Ser Leu Gln  Thr Tyr Val
        995             1000             1005

Thr Gln  Gln Leu Ile Arg Ala  Ala Glu Ile Arg Ala  Ser Ala Asn
    1010             1015             1020

Leu Ala  Ala Thr Lys Met Ser  Glu Cys Val Leu Gly  Gln Ser Lys
    1025             1030             1035

Arg Val  Asp Phe Cys Gly Lys  Gly Tyr His Leu Met  Ser Phe Pro
    1040             1045             1050

Gln Ser  Ala Pro His Gly Val  Val Phe Leu His Val  Thr Tyr Val
    1055             1060             1065

Pro Ala  Gln Glu Lys Asn Phe  Thr Thr Ala Pro Ala  Ile Cys His
    1070             1075             1080

Asp Gly  Lys Ala His Phe Pro  Arg Glu Gly Val Phe  Val Ser Asn
    1085             1090             1095

Gly Thr  His Trp Phe Val Thr  Gln Arg Asn Phe Tyr  Glu Pro Gln
    1100             1105             1110

Ile Ile  Thr Thr Asp Asn Thr  Phe Val Ser Gly Asn  Cys Asp Val
```

```
        1115              1120              1125

Val Ile Gly Ile Val Asn Asn  Thr Val Tyr Asp Pro  Leu Gln Pro
    1130              1135              1140

Glu Leu Asp Ser Phe Lys Glu  Glu Leu Asp Lys Tyr  Phe Lys Asn
    1145              1150              1155

His Thr Ser Pro Asp Val Asp  Leu Gly Asp Ile Ser  Gly Ile Asn
    1160              1165              1170

Ala Ser Val Val Asn Ile Gln  Lys Glu Ile Asp Arg  Leu Asn Glu
    1175              1180              1185

Val Ala Lys Asn Leu Asn Glu  Ser Leu Ile Asp Leu  Gln Glu Leu
    1190              1195              1200

Gly Lys Tyr Glu Gln Tyr Ile  Lys Trp Pro Trp Tyr  Ile Trp Leu
    1205              1210              1215

Gly Phe Ile Ala Gly Leu Ile  Ala Ile Val Met Val  Thr Ile Met
    1220              1225              1230

Leu Cys Cys Met Thr Ser Cys  Cys Ser Cys Leu Lys  Gly Cys Cys
    1235              1240              1245

Ser Cys Gly Ser Cys Cys Lys  Phe Asp Glu Asp Asp  Ser Glu Pro
    1250              1255              1260

Val Leu Lys Gly Val Lys Leu  His Tyr Thr
    1265              1270
```

```
<210> SEQ ID NO 7
<211> LENGTH: 3822
<212> TYPE: DNA
<213> ORGANISM: Sars-CoV-2

<400> SEQUENCE: 7
atgtttgttt ttcttgtttt attgccacta gtctctagtc agtgtgttaa tcttacaacc      60
agaactcaat taccccctgc atacactaat tctttcacac gtggtgttta ttaccctgac     120
aaagttttca gatcctcagt tttacattca actcaggact tgttcttacc tttcttttcc     180
aatgttactt ggttccatgc tatacatgtc tctgggacca atggtactaa gaggtttgat     240
aaccctgtcc taccatttaa tgatggtgtt tattttgctt ccactgagaa gtctaacata     300
ataagaggct ggattttttgg tactacttta gattcgaaga cccagtccct acttattgtt     360
aataacgcta ctaatgttgt tattaaagtc tgtgaatttc aattttgtaa tgatccattt     420
ttgggtgttt attaccacaa aaacaacaaa agttggatgg aaagtgagtt cagagtttat     480
tctagtgcga ataattgcac ttttgaatat gtctctcagc cttttcttat ggaccttgaa     540
ggaaaacagg gtaatttcaa aaatcttagg gaatttgtgt ttaagaatat tgatggttat     600
tttaaaatat attctaagca cacgcctatt aatttagtgc gtgatctccc tcagggtttt     660
tcggctttag aaccattggt agatttgcca ataggtatta acatcactag gtttcaaact     720
ttacttgctt tacatagaag ttatttgact cctggtgatt cttcttcagg ttggacagct     780
ggtgctgcag cttattatgt gggttatctt caacctagga ctttttctatt aaaatataat     840 gaaaatggaa ccattacaga tgctgtagac tgtgcacttg accctctctc agaaacaaag     900
tgtacgttga atcctccac tgtagaaaaa ggaatctatc aaacttctaa ctttagagtc     960
caaccaacag aatctattgt tagatttcct aatattacaa acttgtgccc ttttggtgaa    1020
gtttttaacg ccaccagatt tgcatctgtt tatgcttgga acaggaagag aatcagcaac    1080
tgtgttgctg attattctgt cctatataat tccgcatcat tttccacttt taagtgttat    1140
ggagtgtctc ctactaaatt aaatgatctc tgctttacta atgtctatgc agattcattt    1200
```

```
gtaattagag gtgatgaagt cagacaaatc gctccagggc aaactggaaa gattgctgat      1260
tataattata aattaccaga tgattttaca ggctgcgtta tagcttggaa ttctaacaat      1320
cttgattcta aggttggtgg taattataat tacctgtata gattgtttag gaagtctaat      1380
ctcaaacctt ttgagagaga tatttcaact gaaatctatc aggccggtag cacaccttgt      1440
aatggtgttg aaggttttaa ttgttacttt cctttacaat catatggttt ccaacccact      1500
aatggtgttg gttaccaacc atacagagta gtagtacttt cttttgaact tctacatgca      1560
ccagcaactg tttgtggacc taaaaagtct actaatttgg ttaaaaacaa atgtgtcaat      1620
ttcaacttca atggtttaac aggcacaggt gttcttactg agtctaacaa aaagtttctg      1680
cctttccaac aatttggcag agacattgct gacactactg atgctgtccg tgatccacag      1740
acacttgaga ttcttgacat tacaccatgt tcttttggtg gtgtcagtgt tataacacca      1800
ggaacaaata cttctaacca ggttgctgtt ctttatcagg atgttaactg cacagaagtc      1860
cctgttgcta ttcatgcaga tcaacttact cctacttggc gtgtttattc tacaggttct      1920
aatgtttttc aaacacgtgc aggctgttta atagggctg aacatgtcaa caactcatat      1980
gagtgtgaca tacccattgg tgcaggtata tgcgctagtt atcagactca gactaattct      2040
cctcggcggg cacgtagtgt agctagtcaa tccatcattg cctacactat gtcacttggt      2100
gcagaaaatt cagttgctta ctctaataac tctattgcca tacccacaaa ttttactatt      2160
agtgttacca cagaaattct accagtgtct atgaccaaga catcagtaga ttgtacaatg      2220
tacatttgtg gtgattcaac tgaatgcagc aatcttttgt tgcaatatgg cagtttttgt      2280
acacaattaa accgtgcttt aactggaata gctgttgaac aagacaaaaa cacccaagaa      2340 gttttttgcac aagtcaaaca aatttacaaa acaccaccaa ttaaagattt tggtggtttt      2400
aatttttcac aaatattacc agatccatca aaaccaagca agaggtcatt tattgaagat      2460
ctacttttca acaaagtgac acttgcagat gctggcttca tcaaacaata tggtgattgc      2520
cttggtgata ttgctgctag agacctcatt tgtgcacaaa agtttaacgg ccttactgtt      2580
ttgccacctt tgctcacaga tgaaatgatt gctcaataca cttctgcact gttagcgggt      2640
acaatcactt ctggttggac ctttggtgca ggtgctgcat tacaaatacc atttgctatg      2700
caaatggctt ataggtttaa tggtattgga gttacacaga atgttctcta tgagaaccaa      2760
aaattgattg ccaaccaatt taatagtgct attggcaaaa ttcaagactc actttcttcc      2820
acagcaagtg cacttggaaa acttcaagat gtggtcaacc aaaatgcaca agctttaaac      2880
acgcttgtta aacaacttag ctccaatttt ggtgcaattt caagtgtttt aaatgatatc      2940
ctttcacgtc ttgacaaagt tgaggctgaa gtgcaaattg ataggttgat cacaggcaga      3000
cttcaaagtt tgcagacata tgtgactcaa caattaatta gagctgcaga atcagagct      3060 tctgctaatc ttgctgctac taaaatgtca gagtgtgtac ttggacaatc aaaaagagtt      3120
gatttttgtg gaaagggcta tcatcttatg tccttccctc agtcagcacc tcatggtgta      3180
gtcttcttgc atgtgactta tgtccctgca caagaaaaga acttcacaac tgctcctgcc      3240
atttgtcatg atggaaaagc acactttcct cgtgaaggtg tctttgtttc aaatggcaca      3300
cactggtttg taacacaaag gaattttat gaaccacaaa tcattactac agacaacaca      3360
tttgtgtctg gtaactgtga tgttgtaata ggaattgtca acaacacagt ttatgatcct      3420
ttgcaacctg aattagactc attcaaggag gagttagata aatattttaa gaatcataca      3480
tcaccagatg ttgatttagg tgacatctct ggcattaatg cttcagttgt aaacattcaa      3540
```

```
aaagaaattg accgcctcaa tgaggttgcc aagaatttaa atgaatctct catcgatctc      3600
caagaacttg aaagtatga gcagtatata aaatggccat ggtacatttg gctaggtttt      3660
atagctggct tgattgccat agtaatggtg acaattatgc tttgctgtat gaccagttgc      3720
tgtagttgtc tcaagggctg ttgttcttgt ggatcctgct gcaaatttga tgaagacgac      3780
tctgagccag tgctcaaagg agtcaaatta cattacacat aa                       3822
```

<210> SEQ ID NO 8
<211> LENGTH: 1071
<212> TYPE: DNA
<213> ORGANISM: Acinetobacter baumannii

<400> SEQUENCE: 8

```
atgaaattga gtcgtattgc acttgctact atgcttgttg ctgctccatt agctgctgct        60
aatgctggcg taacagttac tccattattg cttggttaca ctttccaaga cagccaacac       120
aacaatggcg gtaaagatgg taacttaact aacggtcctg agttacaaga cgatttattc       180
gttggcgcag ctcttggtat cgagttaact ccatggttag gtttcgaagc tgaatataac       240
caagttaaag gcgacgtaga cggcgcttct gctggtgctg aatataaaca aaaacaaatc       300
aacggtaact tctatgttac ttctgattta attactaaaa actacgacag caaaatcaag       360
ccgtacgtat tattaggtgc tggtcactat aaatacgact ttgatggcgt aaaccgtggt       420
acacgtggta actcagaaga aggtactta ggtaacgctg tgttggtgc tttctggcgc        480 ttaaacgacg ctttatctct tcgtactgaa gctcgtgcta cttataatgc tgatgaagag       540
ttctggaact atacagctct tgctggctta aacgtagttc ttggtggtca cttgaagcct       600
gctgttcctg tagtagaagt tgctccagtt gaaccaactc cagttgctcc acaaccacaa       660
gagttaactg aagaccttaa catggaactt cgtgtgttct ttgatactaa caatcaaac       720 atcaaagacc aatacaagcc agaaattgct aaagttgctg aaaaattatc tgaataccct       780
aacgctactg cacgtatcga aggtcacaca gataacactg tccacgtaa gttgaacgaa       840 cgtttatctt tagctcgtgc taactctgtt aaatcagctc ttgtaaacga atacaacgtt       900
gatgcttctc gtttgtctac tcaaggtttc gcttgggatc aaccgattgc tgacaacaaa       960
actaaagaag gtcgtgctat gaaccgtcgt gtattcgcga caatcactgg tagccgtact      1020
gtagtagttc aacctggtca agaagcggca gctcctgcag cagctcaata a              1071
```

<210> SEQ ID NO 9
<211> LENGTH: 356
<212> TYPE: PRT
<213> ORGANISM: Acinetobacter baumannii

<400> SEQUENCE: 9

```
Met Lys Leu Ser Arg Ile Ala Leu Ala Thr Met Leu Val Ala Ala Pro
1               5                   10                  15

Leu Ala Ala Ala Asn Ala Gly Val Thr Val Thr Pro Leu Leu Leu Gly
            20                  25                  30

Tyr Thr Phe Gln Asp Ser Gln His Asn Asn Gly Gly Lys Asp Gly Asn
        35                  40                  45

Leu Thr Asn Gly Pro Glu Leu Gln Asp Asp Leu Phe Val Gly Ala Ala
    50                  55                  60

Leu Gly Ile Glu Leu Thr Pro Trp Leu Gly Phe Glu Ala Glu Tyr Asn
65                  70                  75                  80

Gln Val Lys Gly Asp Val Asp Gly Ala Ser Ala Gly Ala Glu Tyr Lys
                85                  90                  95
```

-continued

```
Gln Lys Gln Ile Asn Gly Asn Phe Tyr Val Thr Ser Asp Leu Ile Thr
            100                 105                 110

Lys Asn Tyr Asp Ser Lys Ile Lys Pro Tyr Val Leu Leu Gly Ala Gly
            115                 120                 125

His Tyr Lys Tyr Asp Phe Asp Gly Val Asn Arg Gly Thr Arg Gly Asn
            130                 135                 140

Ser Glu Glu Gly Thr Leu Gly Asn Ala Gly Val Gly Ala Phe Trp Arg
145                 150                 155                 160

Leu Asn Asp Ala Leu Ser Leu Arg Thr Glu Ala Arg Ala Thr Tyr Asn
                165                 170                 175

Ala Asp Glu Glu Phe Trp Asn Tyr Thr Ala Leu Ala Gly Leu Asn Val
            180                 185                 190

Val Leu Gly Gly His Leu Lys Pro Ala Val Pro Val Val Glu Val Ala
            195                 200                 205

Pro Val Glu Pro Thr Pro Val Ala Pro Gln Pro Gln Glu Leu Thr Glu
            210                 215                 220

Asp Leu Asn Met Glu Leu Arg Val Phe Phe Asp Thr Asn Lys Ser Asn
225                 230                 235                 240

Ile Lys Asp Gln Tyr Lys Pro Glu Ile Ala Lys Val Ala Glu Lys Leu
                245                 250                 255

Ser Glu Tyr Pro Asn Ala Thr Ala Arg Ile Glu Gly His Thr Asp Asn
                260                 265                 270

Thr Gly Pro Arg Lys Leu Asn Glu Arg Leu Ser Leu Ala Arg Ala Asn
            275                 280                 285

Ser Val Lys Ser Ala Leu Val Asn Glu Tyr Asn Val Asp Ala Ser Arg
            290                 295                 300

Leu Ser Thr Gln Gly Phe Ala Trp Asp Gln Pro Ile Ala Asp Asn Lys
305                 310                 315                 320

Thr Lys Glu Gly Arg Ala Met Asn Arg Arg Val Phe Ala Thr Ile Thr
                325                 330                 335

Gly Ser Arg Thr Val Val Val Gln Pro Gly Gln Glu Ala Ala Ala Pro
                340                 345                 350

Ala Ala Ala Gln
            355
```

```
<210> SEQ ID NO 10
<211> LENGTH: 1071
<212> TYPE: DNA
<213> ORGANISM: Klebsiella pneumoniae

<400> SEQUENCE: 10
atgaaaaaga cagctatcgc gattgcagtg gcactggctg gcttcgctac cgtagcgcag      60
gccgctccga aagataacac ctggtatgca ggtggtaaac tgggttggtc ccagtatcac     120
gacaccggtt tctacggtaa cggtttccag aacaacaacg gtccgacccg taacgatcag     180
cttggtgctg gtgcgttcgg tggttaccag gttaacccgt acctcggttt cgaaatgggt     240
tatgactggc tgggccgtat ggcatataaa ggcagcgttg acaacggtgc tttcaaagct     300
cagggcgttc agctgaccgc taaactgggt tacccgatca ctgacgatct ggacatctac     360
acccgtctgg gcggcatggt tggcgcgct gactccaaag caactacgc ttctaccggc     420 gtttcccgta cgaacacga cactggcgtt tccccagtat ttgctggcgg cgtagagtgg     480
gctgttactc gtgacatcgc tacccgtctg aataccagt gggttaacaa catcggcgac     540
gcgggcactg tgggtacccg tcctgataac ggcatgctga gcctgggcgt ttcctaccgc     600
```

-continued

```
ttcggtcagg aagatgctgc accggttgtt gctccggctc cggctccggc tccggaagtg      660
gctaccaagc acttcaccct gaagtctgac gttctgttca acttcaacaa agctaccctg      720
aaaccggaag gtcagcaggc tctggatcag ctgtacactc agctgagcaa catggatccg      780
aaagacggtt ccgctgttgt tctgggctac accgaccgca tcggttccga agcttacaac      840
cagcagctgt ctgagaaacg tgctcagtcc gttgttgact acctggttgc taaaggcatc      900
ccggctggca aaatctccgc tcgcggcatg ggtgaatcca ccccggttac tggcaacacc      960
tgtgacaacg tgaaagctcg cgctgccctg atcgattgcc tggctccgga tcgtcgtgta     1020
gagatcgaag ttaaaggcta caaagaagtt gtaactcagc cggcggctta a             1071
```

```
<210> SEQ ID NO 11
<211> LENGTH: 356
<212> TYPE: PRT
<213> ORGANISM: Klebsiella pneumoniae

<400> SEQUENCE: 11

Met Lys Lys Thr Ala Ile Ala Ile Ala Val Ala Leu Ala Gly Phe Ala
1               5                   10                  15

Thr Val Ala Gln Ala Ala Pro Lys Asp Asn Thr Trp Tyr Ala Gly Gly
            20                  25                  30

Lys Leu Gly Trp Ser Gln Tyr His Asp Thr Gly Phe Tyr Gly Asn Gly
        35                  40                  45

Phe Gln Asn Asn Asn Gly Pro Thr Arg Asn Asp Gln Leu Gly Ala Gly
    50                  55                  60

Ala Phe Gly Gly Tyr Gln Val Asn Pro Tyr Leu Gly Phe Glu Met Gly
65                  70                  75                  80

Tyr Asp Trp Leu Gly Arg Met Ala Tyr Lys Gly Ser Val Asp Asn Gly
                85                  90                  95

Ala Phe Lys Ala Gln Gly Val Gln Leu Thr Ala Lys Leu Gly Tyr Pro
            100                 105                 110

Ile Thr Asp Asp Leu Asp Ile Tyr Thr Arg Leu Gly Gly Met Val Trp
            115                 120                 125

Arg Ala Asp Ser Lys Gly Asn Tyr Ala Ser Thr Gly Val Ser Arg Ser
        130                 135                 140

Glu His Asp Thr Gly Val Ser Pro Val Phe Ala Gly Gly Val Glu Trp
145                 150                 155                 160

Ala Val Thr Arg Asp Ile Ala Thr Arg Leu Glu Tyr Gln Trp Val Asn
                165                 170                 175

Asn Ile Gly Asp Ala Gly Thr Val Gly Thr Arg Pro Asp Asn Gly Met
            180                 185                 190

Leu Ser Leu Gly Val Ser Tyr Arg Phe Gly Gln Glu Asp Ala Ala Pro
        195                 200                 205

Val Val Ala Pro Ala Pro Ala Pro Glu Val Ala Thr Lys His
    210                 215                 220

Phe Thr Leu Lys Ser Asp Val Leu Phe Asn Phe Asn Lys Ala Thr Leu
225                 230                 235                 240

Lys Pro Glu Gly Gln Gln Ala Leu Asp Gln Leu Tyr Thr Gln Leu Ser
            245                 250                 255

Asn Met Asp Pro Lys Asp Gly Ser Ala Val Val Leu Gly Tyr Thr Asp
            260                 265                 270

Arg Ile Gly Ser Glu Ala Tyr Asn Gln Gln Leu Ser Glu Lys Arg Ala
        275                 280                 285
```

```
Gln Ser Val Val Asp Tyr Leu Val Ala Lys Gly Ile Pro Ala Gly Lys
    290             295             300

Ile Ser Ala Arg Gly Met Gly Glu Ser Thr Pro Val Thr Gly Asn Thr
305             310             315             320

Cys Asp Asn Val Lys Ala Arg Ala Ala Leu Ile Asp Cys Leu Ala Pro
            325             330             335

Asp Arg Arg Val Glu Ile Glu Val Lys Gly Tyr Lys Glu Val Val Thr
            340             345             350

Gln Pro Ala Ala
        355

<210> SEQ ID NO 12
<211> LENGTH: 591
<212> TYPE: DNA
<213> ORGANISM: Acinetobacter baumannii

<400> SEQUENCE: 12
gtgttcaaaa aagctttggt tattgcatta atggggatgt cttctttac ttttgctggt      60 aactggcaag tgaaatttgg tggtagtgtt attgctccat ctgaagatac accaacacct     120
ttaggcgtgg taaaagcaga tcatgaatat gcatttacac catcagtaga atactttttt     180
ggtcagtctc cattttcggc agaattatta ttagcaacgc ctattaatca tgatgtattg     240
ctagatggta aaaatgcagc acgtataaaa caattaccac caataattac tgcaaaatat     300
cattttaaaa actctacacg tttcacaccg tatattggta ttggtgctac agcatttatt     360
ccttgggatg aagaaggggc agcggtaaag gttaaagaag attttggttt ggcaggtcaa     420
gttggtttta atttccaacc tgctgatgct aaaaactggg gtgtatttgt agatgtacgt     480
tatgctgata ttagtccgga agtaacaatt gatccatcaa ttgctaacta caagtttgat     540
ctagatatta atccttttgt ttatactttg ggttatagct ataaatttta a             591

<210> SEQ ID NO 13
<211> LENGTH: 196
<212> TYPE: PRT
<213> ORGANISM: Acinetobacter baumannii

<400> SEQUENCE: 13

Met Phe Lys Lys Ala Leu Val Ile Ala Leu Met Gly Met Ser Ser Phe
1               5               10              15

Thr Phe Ala Gly Asn Trp Gln Val Lys Phe Gly Gly Ser Val Ile Ala
            20              25              30

Pro Ser Glu Asp Thr Pro Thr Pro Leu Gly Val Val Lys Ala Asp His
        35              40              45

Glu Tyr Ala Phe Thr Pro Ser Val Glu Tyr Phe Phe Gly Gln Ser Pro
    50              55              60

Phe Ser Ala Glu Leu Leu Leu Ala Thr Pro Ile Asn His Asp Val Leu
65              70              75              80

Leu Asp Gly Lys Asn Ala Ala Arg Ile Lys Gln Leu Pro Pro Ile Ile
                85              90              95

Thr Ala Lys Tyr His Phe Lys Asn Ser Thr Arg Phe Thr Pro Tyr Ile
            100             105             110

Gly Ile Gly Ala Thr Ala Phe Ile Pro Trp Asp Glu Glu Gly Ala Ala
            115             120             125

Val Lys Val Lys Glu Asp Phe Gly Leu Ala Gly Gln Val Gly Phe Asn
    130             135             140

Phe Gln Pro Ala Asp Ala Lys Asn Trp Gly Val Phe Val Asp Val Arg
```

```
145             150             155             160

Tyr Ala Asp Ile Ser Pro Glu Val Thr Ile Asp Pro Ser Ile Ala Asn
                165             170             175

Tyr Lys Phe Asp Leu Asp Ile Asn Pro Phe Val Tyr Thr Leu Gly Tyr
            180             185             190

Ser Tyr Lys Phe
        195

<210> SEQ ID NO 14
<211> LENGTH: 639
<212> TYPE: DNA
<213> ORGANISM: Klebsiella pneumoniae

<400> SEQUENCE: 14
atgaagaagt tagcagcggc ggcattgatt cttggcacgc tttctaccgg cagcgtctgg        60
gcgcatgagg cgggggagtt tttcattcgt gccgggaccg ccaccgtccg accgacggag       120
ggctctgaca atgtgttagg cagccttggc agtttcaacg tcagtaacaa tacccagctg       180
ggtttaacct ttacctatat ggcgaccgat aacattggcg tggagttgct tgccgcgacg       240
ccgttccgcc ataaggtcgg caccgggcca accgggacta tcgccaccgt ccatcagctg       300
ccgcccaccc tgatggcgca gtggtacttt ggcgatgcgc aaagcaaggt cgcccgtac        360 gtggggggccg gtatcaacta caccaccttc tttaatgaag actttaacga taccggcaag       420
gcggccgggc tttccgatct gagcctgaag gactcctggg gcgcggcggg gcaggtcggc       480
ctcgattatc tgattaaccg cgactggctg ctgaatatgt cggtgtggta catggatatc       540
gataccgatg tgaaattcaa agccggcggc gtggaccaga aagtcagcac ccgtctggat       600
ccgtgggtgt ttatgttctc cgcaggctat cggttctaa                             639

<210> SEQ ID NO 15
<211> LENGTH: 212
<212> TYPE: PRT
<213> ORGANISM: Klebsiella pneumoniae

<400> SEQUENCE: 15

Met Lys Lys Leu Ala Ala Ala Ala Leu Ile Leu Gly Thr Leu Ser Thr
1               5               10              15

Gly Ser Val Trp Ala His Glu Ala Gly Glu Phe Phe Ile Arg Ala Gly
            20              25              30

Thr Ala Thr Val Arg Pro Thr Glu Gly Ser Asp Asn Val Leu Gly Ser
        35              40              45

Leu Gly Ser Phe Asn Val Ser Asn Asn Thr Gln Leu Gly Leu Thr Phe
    50              55              60

Thr Tyr Met Ala Thr Asp Asn Ile Gly Val Glu Leu Leu Ala Ala Thr
65              70              75              80

Pro Phe Arg His Lys Val Gly Thr Gly Pro Thr Gly Thr Ile Ala Thr
                85              90              95

Val His Gln Leu Pro Pro Thr Leu Met Ala Gln Trp Tyr Phe Gly Asp
            100             105             110

Ala Gln Ser Lys Val Arg Pro Tyr Val Gly Ala Gly Ile Asn Tyr Thr
        115             120             125

Thr Phe Phe Asn Glu Asp Phe Asn Asp Thr Gly Lys Ala Ala Gly Leu
    130             135             140

Ser Asp Leu Ser Leu Lys Asp Ser Trp Gly Ala Ala Gly Gln Val Gly
145             150             155             160
```

-continued

```
Leu Asp Tyr Leu Ile Asn Arg Asp Trp Leu Leu Asn Met Ser Val Trp
            165             170             175

Tyr Met Asp Ile Asp Thr Asp Val Lys Phe Lys Ala Gly Gly Val Asp
            180             185             190

Gln Lys Val Ser Thr Arg Leu Asp Pro Trp Val Phe Met Phe Ser Ala
        195             200             205

Gly Tyr Arg Phe
    210
```